US011642642B2

(12) United States Patent
Oakey et al.

(10) Patent No.: US 11,642,642 B2
(45) Date of Patent: May 9, 2023

(54) EXPLOITING OXYGEN INHIBITED PHOTOPOLYMERIZATION WITHIN EMULSION DROPLETS FOR THE FABRICATION OF MICROPARTICLES WITH CUSTOMIZABLE PROPERTIES

(71) Applicant: University of Wyoming, Laramie, WY (US)

(72) Inventors: John Oakey, Laramie, WY (US); Katie Dongmei Li-Oakey, Laramie, WY (US); Daniel Debroy, Laramie, WY (US); Carl Frick, Laramie, WY (US); Rajib Shaha, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 0 days.

(21) Appl. No.: 16/647,869

(22) PCT Filed: Oct. 17, 2018

(86) PCT No.: PCT/US2018/056237
§ 371 (c)(1),
(2) Date: Mar. 16, 2020

(87) PCT Pub. No.: WO2019/079414
PCT Pub. Date: Apr. 25, 2019

(65) Prior Publication Data
US 2020/0254417 A1    Aug. 13, 2020

Related U.S. Application Data

(60) Provisional application No. 62/586,680, filed on Nov. 15, 2017, provisional application No. 62/573,576, filed on Oct. 17, 2017.

(51) Int. Cl.
*B01J 13/14* (2006.01)
*A61K 9/16* (2006.01)
*B01J 13/00* (2006.01)

(52) U.S. Cl.
CPC ............. *B01J 13/14* (2013.01); *A61K 9/1635* (2013.01); *B01J 13/0065* (2013.01)

(58) Field of Classification Search
CPC ...... B01J 13/14; B01J 13/0065; A61K 9/1635
See application file for complete search history.

(56) References Cited

U.S. PATENT DOCUMENTS

| 5,573,934 | A | 11/1996 | Hubbell et al. |
| 5,631,079 | A | 5/1997 | Gutman et al. |
| 2002/0193546 | A1 | 12/2002 | Freeman et al. |
| 2003/0045597 | A1 | 3/2003 | Randolph et al. |
| 2007/0242111 | A1 | 10/2007 | Pamula et al. |
| 2011/0104052 | A1 | 5/2011 | Barnett et al. |
| 2011/0129941 | A1 | 6/2011 | Kumacheva et al. |
| 2017/0145169 | A1* | 5/2017 | Oakey ..................... A61L 27/16 |

FOREIGN PATENT DOCUMENTS

| CN | 101018816 A | 8/2007 |
| CN | 102171234 A | 8/2011 |
| CN | 102898134 A | 1/2013 |
| WO | WO 2019/079414 A1 | 4/2019 |

OTHER PUBLICATIONS

Abbyad et al. (2010) "Sickling of red blood cells through rapid oxygen exchange in microfluidic drops," Lab Chip. 10:2505-2512.
Ahmad et al. (Apr. 2015) "Hydrogel Microparticles as an Emerging Tool in Pharmaceutical Field: a Review," Adv. Polym. Technol. 35 (2), 121-128.
Ahmed (Mar. 2015) "Hydrogel: Preparation, characterization, and applications: A Review," Journal of Advanced Research. 6(2):105-121.
An et al. (2013) "Synthesis of biomimetic oxygen-carrying compartmentalized microparticles using flow lithography," Lab Chip. 13:4765-4774.
An et al. (Jul. 2014) "Synthesis of colloidal microgels using oxygen-controlled flow lithography," Soft Matter 10(38): 7595-7605.
Anderson et al. (2000) "Fabrication of Topologically Complex Three-Dimensional Microfluidic Systems in PDMS by Rapid Prototyping," Anal. Chem. 72 (14), 3158-3164.
Anderson et al. (May 2011) "The performance of human mesenchymal stem cells encapsulated in cell-degradable polymer-peptide hydrogels," Biomaterials. 32(14):3564-3574.
Andrzejewska (2001) "Photopolymerization kinetics of multifunctional monomers," Progress in Polymer Science. 26:605-665.

(Continued)

*Primary Examiner* — Shirley V Gembeh
(74) *Attorney, Agent, or Firm* — Leydig, Voit & Mayer, Ltd.

(57) ABSTRACT

Described are methods and devices for the generation of hydrogel particles with micrometer and submicrometer dimensions using oxygen-inhibited partial polymerization, and the particles generated therefrom. The described methods generate particles with dimensions independent of the starting polymerizable solution dimension, for example, a microdroplet. Further, microfluidic flow parameters (e.g. viscosity, flow rate) and photopolymerization process parameters (e.g. optical exposure intensity and duration) are controlled to generate particles with tunable crosslinking density-determined properties including elasticity, diffusivity, and biomolecular display for diverse applications such as drug delivery, tissue engineering cell scaffolds, and single- and multiple- cell therapeutics. Similarly, gradients of cross-linking density-determined properties can be created within single particles through the selection of optical exposure intensity and duration. In addition to conventional spherical shapes, a suite of non-spherical shapes may be generated by manipulating the dimensions of the microfluidic channels and other related physical and process parameters.

22 Claims, 35 Drawing Sheets

(56) References Cited

OTHER PUBLICATIONS

Anna et al. (2006) "Microscale Tipstreaming in a Microfluidic Flow Focusing Device," Phys. Fluids 18 (12), 121512, 13 pp.
Ansari et al. (Mar. 2016) "Muscle Tissue Engineering Using Gingival Mesenchymal Stem Cells Encapsulated in Alginate Hydrogels Containing Multiple Growth Factors," Annals of Biomedical Engineering 44(6):1908-1920.
Anseth et al. (2002) "In Situ Forming Degradable Networks and Their Application in Tissue Engineering and Drug Delivery," Journal of Controlled Release 78, 199-209.
Appleyard et al. (2011) "Bar-coded hydrogel microparticles for protein detection: synthesis, assay and scanning," Nature Protocols. 6:1761-1774.
Armstrong (1994) "The analysis of free radicals, lipid peroxides, antioxidant enzymes and compounds related to oxidative stress as applied to the clinical chemistry laboratory," Free radicals in diagnostic medicine. 366:43-58.
Australian First Examination Report, dated Aug. 23, 2021, corresponding to Australian Application Serial No. 2016346332, 2 pp.
Bamford et al. (Aug. 1949) "The autoxidation of tetralin," Proceedings of the Royal Society of London A: Mathematical, Physical and Engineering Sciences. 198(1053):252-267.
Beamish et al. (2009) "The Effects of Monoacrylated Poly(Ethylene Glycol) on the Properties of Poly(Ethylene Glycol) Diacrylate Hydrogels Used for Tissue Engineering," J. Biomed. Mater. Res. 9999A, NA-NA.
Becker et al. (2006) "The Role of Hydroquinone Monomethyl Ether in the Stabilization of Acrylic Acid," Chem. Eng. Technol. 29 (10), 1227-1231.
Benoit et al. (Oct. 2008) "Small functional groups for controlled differentiation of hydrogel-encapsulated human mesenchymal stem cells," Nature Materials. 7(10):816-823.
Benya et al. (Aug. 1982) "Dedifferentiated chondrocytes reexpress the differentiated collagen phenotype when cultured in agarose gels," Cell. 30(1):215-224.
Billiet et al. (2012) "A review of trends and limitations in hydrogel-rapid prototyping for tissue engineering," Biomaterials. 33:6020-6041.
Bong et al. (2010) "Magnetic Barcoded Hydrogel Microparticles for Multiplexed Detection," Langmuir 26 (11), 8008-8014.
Bryant et al. (2000) "Cytocompatibility of UV and visible light photoinitiating systems on cultured NIH/3T3 fibroblasts in vitro," Journal of Biomaterials Science, Polymer. 11:439-457.
Bryant et al. (2004) "Encapsulating chondrocytes in degrading PEG hydrogels with high modulus: engineering gel structural changes to facilitate cartilaginous tissue production," Biotechnology and Bioengineering. 86(7):747-755.
Buenger et al. (2012) "Hydrogels in Sensing Applications," Progress in Polymer Science 37 (12), 1678-1719.
Burdick et al. (2002) "Photoencapsulation of Osteoblasts in Injectable RGD-Modified PEG Hydrogels for Bone Tissue Engineering," Biomaterials No. 23, 4315-4323.
Burdick et al. (2004) "Fabrication of Gradient Hydrogels Using a Microfluidics/Photopolymerization Process," Langmuir 20 (13), 5153-5156.
Burkoth et al. (2000) "A review of photocrosslinked polyanhydrides: in situ forming degradable networks," Biomaterials. 21:2395-2404.
Burton et al. (1981) "Autoxidation of Biological Molecules. 1. The Antioxidant Activity of Vitamin E and Related Chain-Breaking Phenolic Antioxidants in Vitro," J. Am. Chem. Soc. No. 103, 6472-6477.
Buwalda et al. (2017) "Hydrogels for Therapeutic Delivery: Current Developments and Future Directions," Biomacromolecules 18 (2), 316-330.
Cabiscol et al. (Mar. 2000) "Oxidative stress in bacteria and protein damage by reactive oxygen species," International Microbiology. 3(1):3-8.
Chinese Office Action, dated Aug. 4, 2021, corresponding to Chinese Patent Application No. 201680075469.9, 9 pp.
Chinese Office Action, dated Feb. 24, 2021, corresponding to Chinese Patent Application No. 201680075469.9, 21 pages.
Chinese Office Action, dated Jun. 3, 2020, in Chinese Patent Application No. 201680075469.9, 31 pp.
Choh et al. (Apr. 11, 2011) "Facile synthesis and characterization of disulfide-cross-linked hyaluronic acid hydrogels for protein delivery and cell encapsulation," Biomacromolecules. 12(4):1126-1136.
Choi et al. (2012) "Multiplexed Detection of mRNA Using Porosity-Tuned Hydrogel Microparticles," Anal. Chem. 84 (21), 9370-9378.
Chong (1969) "Oxygen Consumption During Induction Period," Journal of Applied Polymer Science 13, 241-247.
Chou et al. (2009) "Characterization of photocrosslinked alginate hydrogels for nucleus pulposus cell encapsulation," J. Biomed. Mater. Res. 91A(1):187-194.
Colley et al. (2002) "Probing the Reactivity of Photoinitiators for Free Radical Polymerization: Time-Resolved Infrared Spectroscopic Study of Benzoyl Radicals," J. Am. Chem. Soc. 124 (50), 14952-14958.
Cox et al. (1986) "Oxygen diffusion in poly(dimethyl siloxane) using fluorescence quenching. I. Measurement technique and analysis," Journal of Polymer Science Part A: Polymer Chemistry. 24:621-636.
Cruise et al. (1998) "Characterization of Permeability and Network Structure of Interfacially Photopolymerized Poly(Ethylene Glycol) Diacrylate Hydrogels," Biomaterials No. 19, 1287-1294.
Dang et al. (2012) "Preparation of Monodisperse PEG Hydrogel Microparticles Using a Microfluidic Flow-Focusing Device," Journal of Industrial and Engineering Chemistry 18 (4), 1308-1313.
Datta (2007) "Characterization of Polyethylene Glycol Hydrogels for Biomedical Applications," LSU Master's Theses, 3502. 117 pp. https://digitalcommons.lsu.edu/gradschool_theses/3502.
De Geest et al. (2005) "Synthesis of Monodisperse Biodegradable Microgels in Microfluidic Devices," Langmuir 21 (23), 10275-10279.
Debroy et al. (2017) "Fabrication of Non-Spherical Hydrogel Particles for Drug Delivery," poster for NIH Western Region IDeA conference, Oct. 18, 2017.
Debroy et al. (2018) "Interfacially-mediated oxygen inhibition for precise and continuous poly (ethylene glycol) diacrylate (PEGDA) particle fabrication," Journal of Colloid and Interface Science 510, 334-344, available online Sep. 22, 2017.
Debroy et al. (2018) "Supplementary Material for Interfacially-mediated oxygen inhibition for precise and continuous poly (ethylene glycol) diacrylate (PEGDA) particle fabrication," Journal of Colloid and Interface Science, available online at https://doi.org/10.1016/j.jcis.2017.09.081, 10 pp.
Decker et al. (1985) "Kinetic Approach of Oxygen Inhibition in Ultraviolet- and Laser-Induced Polymerizations," Macromolecules 1241-1244.
DeForest et al. (2009) "Sequential Click Reactions for Synthesizing and Patterning Three-Dimensional Cell Microenvironments," Nature Materials 8 (8), 659-664.
Dendukuri et al. (2007) "Stop-flow lithography in a microfluidic device," Lab Chip 7:818-828.
Dendukuri et al. (2008) "Modeling of Oxygen-Inhibited Free Radical Photopolymerization in a PDMS Microfluidic Device," Macromolecules. 41:8547-8556.
Du et al. (1995) "ABA Type Copolymers of Lactide with Poly(Ethylene Glycol). Kinetic, Mechanistic, and Model Studies," Macromolecules 28, 2124-2132.
Du et al. (2008) "Directed assembly of cell-laden microgels for fabrication of 3D tissue constructs," Proceedings of the National Academy of Sciences. 105(28):9522-9527.
Duffy et al. (1999) "Rapid prototyping of microfluidic switches in poly (dimethyl siloxane) and their actuation by electroosmotic flow," Journal of Micromechanics and Microengineering. 9:211.
Esterbauer (1992) "The role of lipid peroxidation and antioxidants in oxidative modification of LDL," Free Radical Biology and Medicine. 13(4):341-390.
European Extended Search Report issued in EP 16860701.8, dated Jun. 3, 2019, related to the present application, 7 pp.
European Office Action issued in 16860701-8 dated Feb. 13, 2020.

(56) References Cited

OTHER PUBLICATIONS

European Office Action, dated Jun. 23, 2020, corresponding to European Patent Application No. 16860701.8, 4 pp.
Fairbanks et al. (2009) "A Versatile Synthetic Extracellular Matrix Mimic via Thiol-Norbornene Photopolymerization," Adv. Mater. 21(48):5005-5010.
Fairbanks et al. (2009) "Photoinitiated polymerization of PEG-diacrylate with lithium phenyl-2, 4, 6-trimethylbenzoylphosphinate: polymerization rate and cytocompatibility," Biomaterials. 30(35):6702-6707.
Ford et al. (2006) "A macroporous hydrogel for the coculture of neural progenitor and endothelial cells to form functional vascular networks in vivo," Proceedings of the National Academy of Sciences. 103:2512-2517.
Gobaa et al. (2011) "Artificial niche microarrays for probing single stem cell fate in high throughput," Nature Methods 8(11): 949-955.
Gou et al. (2006) "Consumption of the Molecular Oxygen in Polymerization Systems Using Photosensitized Oxidation of Dimethylanthracene," Chemical Engineering Communications 193 (5), 620-627.
Gref et al. (1994) "Biodegradable long-circulating polymeric nanospheres," Science. 263(5153):1600-1603.
Griffith (2000) "Polymeric Biomaterials," Acta mater 2000, No. 48, 263-277.
Grigoriev et al. (2006) "Chaotic mixing in microdroplets," Lab Chip. 6:1369-1372.
Guo et al. (2010) "Repair of osteochondral defects with biodegradable hydrogel composites encapsulating marrow mesenchymal stem cells in a rabbit model," Acta Biomaterialia. 6(1):39-47.
Hagel et al. (2013) "Diffusion and Interaction in PEG-DA Hydrogels," Biointerphases 8 (36), 1-9.
Hamidi et al. (2008) "Hydrogel Nanoparticles in Drug Delivery," Advanced Drug Delivery Reviews 60 (15), 1638-1649.
Hamilton et al. (2013) "Development of 3-D Hydrogel Culture Systems With On Demand Cell Separation," Biotechnology Journal. 8:485-495.
Harrane et al. (2011) "PLA-Based Biodegradable and Tunable Soft Elastomers for Biomedical Applications," Biomed. Mater. 6 (6), 065006-065012.
Hazel et al. (2013) "Changes in cytoplasmic volume are sufficient to drive spindle scaling," Science. 342:853-856.
He et al. (2004) "Concentrating Solutes and Nanoparticles Within Individual Aqueous Microdroplets," Anal. Chem. 76 (5), 1222-1227.
Helgeson et al. (2011) "Hydrogel Microparticles From Lithographic Processes: Novel Materials for Fundamental and Applied Colloid Science," Current Opinion in Colloid & Interface Science 16 (2), 106-117.
Höfer et al. (2008) "Oxygen Scavengers and Sensitizers for Reduced Oxygen Inhibition in Radical Photopolymerization," J. Polym. Sci. A Polym. Chem. 46 (20), 6916-6927.
Hoffman (2012) "Hydrogels for Biomedical Applications," Advanced Drug Delivery Reviews 64, 18-23.
Holtze et al. (2008) "Biocompatible Surfactants for Water-in-Fluorocarbon Emulsions," Lab Chip 8 (10), 1632-1639.
Hoyle et al. (2010) "Thiol-Ene Click Chemistry," Angew. Chem. Int. 49(9):1540-1573.
Hristova et al. (2005) "Addition of Benzoyl Radicals to Butyl Acrylate: Absolute Rate Constants by Time-Resolved EPR," Macromolecules 38 (18), 7714-7720.
Hwang et al. (2009) "Stop-Flow Lithography for the Production of Shape-Evolving Degradable Microgel Particles," Journal of the American Chemical Society. 131:4499-4504.
Hwang et al. (2010) "Benchtop fabrication of PDMS microstructures by an unconventional photolithographic method," Biofabrication. 2:045001-045001.
Imlay (1988) "DNA damage and oxygen radical toxicity," Science. 240(4857):1302-1309.
International Preliminary Report on Patentability issued in No. PCT/US2016/058897, dated May 1, 2018, 8 pp.
International Preliminary Report on Patentability issued in No. PCT/US2018/056237, dated Apr. 30, 2020, 9 pp.
International Search Report and Written Opinion corresponding to International Patent Application No. PCT/US2018/056237, dated Dec. 21, 2018, 11 pp.
International Search Report corresponding to International Patent Application No. PCT/US2016/058897, dated Jan. 17, 2017.
Jariwala et al. (2011) "Modeling effects of oxygen inhibition in mask-based stereolithography," Rapid Prototyping Journal. 17:168-175.
Jeong et al. (2012) "Controlled Generation of Submicron Emulsion Droplets via Highly Stable Tip-Streaming Mode in Microfluidic Devices," Lab Chip 12 (8), 1446-1453.
Jiang et al. (Jun. 2015) "Microfluidic generation of uniform water droplets using gas as the continuous phase," Journal of Colloid and Interface Science 448:275-279.
Jiang et al. (2017) "A microfluidic-based cell encapsulation platform to achieve high long-term cell viability in photopolymerized PEGNB hydrogel microspheres," J. Mater. Chem. B. 5:173-180.
Joao (2016) "Inverted Colloidal Crystal Scaffolds: New Substitutes for Bone Tissue Engineering," Doctoral dissertation, Universidade NOVA de Lisboa (Portugal) [online], retrieved on Nov. 27, 2018 from https://run.unl.pt/handle/10362/19891. Dec. 2016, p. 25, 8 pp.
Jockusch et al. (1998) "Phosphinoyl Radicals: Structure and Reactivity. a Laser Flash Photolysis and Time-Resolved ESR Investigation," J. Am. Chem. Soc. 120 (45), 11773-11777.
Jockusch et al. (1999) "Radical Addition Rate Constants to Acrylates and Oxygen: A-Hydroxy and A-Amino Radicals Produced by Photolysis of Photoinitiators," J. Am. Chem. Soc. 121 (16), 3921-3925.
Jockusch et al. (2001) "Photochemistry and Photophysics of A-Hydroxy Ketones," Macromolecules 34 (6), 1619-1626.
Kar et al. (Jan. 2016) "Poly(ethylene glycol) hydrogels with cell cleavable groups for autonomous cell delivery," Biomaterials. 77:186-197.
Karihaloo et al. (2013) "Honeybee combs: how the circular cells transform into rounded hexagons," J R Soc Interface. 10(86):20130299. 4 pp.
Kenney et al. (1998) "Mutation Typing Using Electrophoresis and Gel-Immobilized Acrydite," BioTechniques 25 (3), 516-521.
Kharkar et al. (Jul. 2015) "Design of Thiol- and Light-Sensitive Degradable Hydrogels Using Michael-Type Addition Reactions," Polym. Chem. 6 (31), 5565-5574.
Kim et al. (2007) "Controlled Production of Emulsion Drops Using an Electric Field in a Flow-Focusing Microfluidic Device," Appl. Phys. Lett. 91 (13), 133106-3.
Kim et al. (2013) "Mathematical Analysis of Oxygen Transfer Through Polydimethylsiloxane Membrane Between Double Layers of Cell Culture Channel and Gas Chamber in Microfluidic Oxygenator," Microfluid Nanofluid 15 (3), 285-296.
Kim et al. (2014) "Droplet Microfluidics for Producing Functional Microparticles," Langmuir 30 (6), 1473-1488, published online Nov. 8, 2013.
Kizilel et al. (2006) "Mathematical Model for Surface-Initiated Photopolymerization of Poly(Ethylene Glycol) Diacrylate," Macromol. Theory Simul. 15 (9), 686-700.
Klein et al. (May 2015) "Droplet barcoding for single-cell transcriptomics applied to embryonic stem cells," Cell. 161(5):1187-1201.
Kloxin et al. (2009) "Photodegradable hydrogels for dynamic tuning of physical and chemical properties," Science. 324(5923):59-63.
Kloxin et al. (2010) "Mechanical properties of cellularly responsive hydrogels and their experimental determination," Adv. Mater. 22(31):3484-3494.
Kloxin et al. (2010) "Synthesis of photodegradable hydrogels as dynamically tunable cell culture platforms," Nature Protocols. 5:1867-1887.
Krutkramelis et al. (Oct. 26-30, 2014) "Microfludic hydrogen particle production and flow-assistanced assembly for constructing composite scaffold materials", 18th Int'l Conference on Miniaturized Systems for Chemistry and Life Sciences, San Antonio, Texas US, 3 pp.

(56) References Cited

OTHER PUBLICATIONS

Krutkramelis et al. (Feb. 24, 2016) "Monodisperse polyethylene glycol diacrylate hydrogel microsphere formation by oxygen-controlled photopolymerization in a microfluidic device," Lab Chip. 16:1457-1465.
Kubie (1927) "The solubility of O2, CO2, and N2 in mineral oil and the transfer of carbon dioxide from oil to air," Journal of Biological Chemistry. 72(2):545-548.
Kuck et al. (2008) "Photopolymerization as an innovative detection technique for low-density microarrays," Biotech. 45:179-186.
Kumacheva et al. (2003) "Two-Dimensional Colloid Crystals Obtained by Coupling of Flow and Confinement," Phys. Rev. Lett. 91:128301-128304.
Lacy et al. (1991) "Maintenance of normoglycemia in diabetic mice by subcutaneous xenografts of encapsulated islets," Science. 254(5039):1782-1784.
Ladygin et al. (1984) "Kinetics of the Reactions of Peroxy-Radicals Formed by the Electronirradiation of Normal and Cyclic Hydrocarbons in the Presence of Oxygen," High Energy Chemistry. 18(4):241-244.
Lam et al. (Mar. 2016) "Evaluation of cell-laden polyelectrolyte hydrogels incorporating poly(L-Lysine) for applications in cartilage tissue engineering," Biomaterials. 83:332-346.
Lanasa et al. (2011) "Presence of pores and hydrogel composition influence tensile properties of scaffolds fabricated from well-defined sphere templates," Journal of Biomedical Materials Research Part B: Applied Biomaterials. 96B:294-302.
Landfester et al. (2010) "Hydrogels in Miniemulsions," in: Pich et al. (eds) Chemical Design of Responsive Microgels, Adv Polym Sci. 234:39-63.
Le Goff et al. (Nov. 2015) "Hydrogel Microparticles for Biosensing," European Polymer Journal 72 (C), 386-412.
Lebourg et al. (2007) "Biodegradable polycaprolactone scaffold with controlled porosity obtained by modified particle-leaching technique," J Mater Sci: Mater Med. 19:2047-2053.
Lee et al. (2009) "Poly(Ethylene Glycol) Hydrogel Microparticles Containing Enzyme-Fluorophore Conjugates for the Detection of Organophosphorus Compounds," Sensors and Actuators B: Chemical 137 (1), 209-214.
Lee et al. (2010) "Development of Macroporous Poly(Ethylene Glycol) Hydrogel Arrays Within Microfluidic Channels," Biomacromolecules 11 (12), 3316-3324.
Lemke et al. (2009) "Microfluidic Device for Single-Molecule Experiments with Enhanced Photostability," J. Am. Chem. Soc. 131(38):13610-13612.
Lewis et al. (2010) "Fabrication of Uniform DNA-Conjugated Hydrogel Microparticles via Replica Molding for Facile Nucleic Acid Hybridization Assays," Anal. Chem. 82 (13), 5851-5858.
Lewis et al. (2010) "Microfluidic Fabrication of Hydrogel Microparticles Containing Functionalized Viral Nanotemplates," Langmuir. 26:13436-13441.
Li et al. (Apr. 2014) "Micropatterned cell-cell interactions enable functional encapsulation of primary hepatocytes in hydrogel microtissues," Tissue Engineering. 20A(15-16):2200-2212.
Ligon et al. (2014) "Strategies to Reduce Oxygen Inhibition in Photoinduced Polymerization," Chem. Rev. 114:557-589, published online Oct. 1, 2013.
Lin et al. (2011) "PEG hydrogels formed by thiol-ene photo-click chemistry and their effect on the formation and recovery of insulin-secreting cell spheroids," Biomaterials. 32(36):9685-9695.
Lin et al. (Jul. 24, 2009) "Controlling Affinity Binding with Peptide-Functionalized Poly(ethylene glycol) Hydrogels," Adv. Funct. Mater. 19(14):2325-2331.
Lindner et al. (1995) "Implantation of encapsulated catecholamine and GDNF-producing cells in rats with unilateral dopamine depletions and parkinsonian symptoms," Experimental Neurology. 132(1):62-76.
Liu et al. (May 2016) "Methods for Generating Hydrogel Particles for Protein Delivery," Annals of Biomedical Engineering 44 (6), 1946-1958.
Lu et al. (2006) "A digital micro-mirror device-based system for the microfabrication of complex, spatially patterned tissue engineering scaffolds," J. Biomed. Mater. Res. 77A(2):396-405.
Luchini et al. (2008) "Smart Hydrogel Particles: Biomarker Harvesting: One-Step Affinity Purification, Size Exclusion, and Protection Against Degradation," Nano Lett. 8 (1), 350-361.
Lustig et al. (1988) "Solute Diffusion in Swollen Membranes. IX. Scaling Laws for Solute Diffusion in Gels," Journal of Applied Polymer Science 735-747.
Ma et al. (Sep. 2014) "On the flow topology inside droplets moving in rectangular microchannels," Lab Chip. 14:3611-3620.
Macosko et al. (May 2015) "Highly Parallel Genome-wide Expression Profiling of Individual Cells Using Nanoliter Droplets," Cell. 161(5):1202-1214.
Mahadik et al. (2013) "Microfluidic Generation of Gradient Hydrogels to Modulate Hematopoietic Stem Cell Culture Environment," Adv. Healthcare Mater. 3 (3), 449-458.
Mahoney et al. (2006) "Three-dimensional growth and function of neural tissue in degradable polyethylene glycol hydrogels," Biomaterials. 27(10):2265-2274.
Majima et al. (1991) "Phenyl-2,4,6-trimethylbenzoylphosphinates as water-soluble photoinitiators. Generation and reactivity of O $\dot{P}$(C6H5)(O-) radical anions," Macromolecular Chemistry and Physics. 192(10):2307-2315.
Mann et al. (2001) "Smooth muscle cell growth in photopolymerized hydrogels with cell adhesive and proteolytically degradable domains: synthetic ECM analogs for tissue engineering," Biomaterials. 22:3045-3051.
Mayo (1968) "Free radical autoxidations of hydrocarbons," Accounts of Chemical Research. 1(7):193-201.
McDonald et al. (2002) "Poly(Dimethylsiloxane) as a Material for Fabricating Microfluidic Devices," Acc. Chem. Res. 35 (7), 491-499.
Melville et al. (1954) "Biological Properties of Biotin D- and L-Sulfoxides," J. Biol. Chem. No. 208, 503-512.
Merkel et al. (2000) "Gas Sorption, Diffusion, and Permeation in Poly(Dimethylsiloxane)," Journal of Polymer Science Part B Polymer Physics 38, 415-434.
Metters et al. (2000) "A Statistical Kinetic Model for the Bulk Degradation of PLA-b-PEG-b-PLA Hydrogel Networks," J. Phys. Chem. B. 104:7043-7049.
Mexal et al. (1975) "Oxygen Availability in Polyethylene Glycol Solutions and Its Implications in Plant-Water Relations," Plant Physiology No. 55, 20-24.
Miller et al. (2003) "N-Vinylamides and Reduction of Oxygen Inhibition in Photopolymerization of Simple Acrylate Formulations," In Photoinitiated Polymerization; ACS Symposium Series; 847, pp. 2-14.
Monette et al. (Jan. 2016) "Chitosan thermogels for local expansion and delivery of tumor-specific T lymphocytes towards enhanced cancer immunotherapies," Biomaterials. 75:237-249.
Mooney et al. (2011) "Control of Neural Cell Composition in Poly(Ethylene Glycol) Hydrogel Culture with Soluble Factors," Tissue Engineering. 17A:2805-2815.
Mũnoz et al. (Apr. 2014) "Gelatin hydrogels formed by orthogonal thiol-norbornene photochemistry for cell encapsulation," Biomater. Sci. 2:1063-1072.
Murua et al. (2008) "Cell microencapsulation technology: towards clinical application," Journal of Controlled Release. 132(2):76-83.
Nair et al. (2012) "UV-Induced Radical Photo-Polymerization: A Smart Tool for Preparing Polymer Electrolyte Membranes for Energy Storage Devices," Membranes. 2:687-704.
Nguyen et al. (2002) "Photopolymerizable hydrogels for tissue engineering applications," Biomaterials. 23:4307-4314.
Nicodemus et al. (2008) "Cell encapsulation in biodegradable hydrogels for tissue engineering applications," Tissue Engineering. 14B:149-165.
Niinomi (2008) "Metallic Biomaterials" J Artif Organs, 11 (3), 105-110.
O'Brien (2006) "Modeling the Effect of Oxygen on Photopolymerization Kinetics," Macromol. Theory Simul. 15(2):176-182.
O'Brien et al. (2004) "The Impact of Oxygen on Photopolymerization Kinetics," RadTech el5 2004 Technical Proceedings, 9 pp.

(56) References Cited

OTHER PUBLICATIONS

O'Brien et al. (2006) "Oxygen inhibition in thiol-acrylate photopolymerizations," J. Polym. Sci. Polym. Chem. 44(6):2007-2014.
O'Brien et al. (2006) "Impact of Oxygen on Photopolymerization Kinetics and Polymer Structure," Macromolecules. 39:2501-2506.
Oh et al. (2008) "The Development of Microgels/Nanogels for Drug Delivery Applications," Progress in Polymer Science 33 (4), 448-477.
Olabisi et al. (2010) "Hydrogel Microsphere Encapsulation of a Cell-Based Gene Therapy System Increases Cell Survival of Injected Cells, Transgene Expression, and Bone Volume in a Model of Heterotopic Ossification," Tissue Engineering. 16A:3727-3736.
Oliveira et al. (2011) "Polymer-based microparticles in tissue engineering and regenerative medicine," Biotechnol Progress. 27:897-912.
Panda et al. (2008) "Stop-flow lithography to generate cell-laden microgel particles," Lab Chip. 8(7):1056-1061.
Patel et al. (2011) "Hydrogel Biomaterials," Ch. 14, In; Biomedical Engineering—Frontiers and Challenges. pp. 275-296.
Peppas (2000) "Hydrogels in pharmaceutical formulations," European Journal of Pharmaceutics and Biopharmaceutics. 50:27-46.
Peppas et al. (1989) "A Simple Equation for the Description of Solute Release. III. Coupling of Diffusion and Relaxation," International Journal of Pharmaceutics No. 57, 169-172.
Peppas et al. (2006) "Hydrogels in Biology and Medicine: From Molecular Principles to Bionanotechnology," Adv. Mater. 18 (11), 1345-1360.
Perez et al. (2011) "A collagen peptide-based physical hydrogel for cell encapsulation," Macromol. Biosci. 11(10):1426-1431.
Pregibon et al. (2007) "Multifunctional encoded particles for highthroughput biomolecule analysis," Science. 315:1393-1396.
Priola et al. (1993) "Properties of polymeric films obtained from U.V. cured poly(ethylene glycol) diacrylates," Polymer. 34(17):3653-3657.
Ramanan et al. (2006) "Development of a Temperature-Sensitive Composite Hydrogel for Drug Delivery Applications," Biotechnol Progress 22 (1), 118-125.
Reece et al. (Aug. 2016) "Microfluidic techniques for high throughput single cell analysis," Current Opinion in Biotechnology. 40:90-96.
Rehman et al. (1999) "Immobilization of Acrylamide-Modified Oligonucleotides by Co-Polymerization," Nucleic Acids Res 27 (2), 649-655.
Rice et al. (2004) "Encapsulating chondrocytes in copolymer gels: Bimodal degradation kinetics influence cell phenotype and extracellular matrix development," J. Biomed. Mater. Res. 70A:560-568.
Riess et al. (1982) "Solubility and Transport Phenonena in Perfluorochemicals Relevant to Blood Substitution and Other Biomedical Applications," Pure and Applied Chemistry. 54(12):2383-2406.
Roberts et al. (2013) "Comparison of photopolymerizable thiol-ene PEG and acrylate-based PEG hydrogels for cartilage development," Biomaterials. 34(38):9969-9979.
Ross et al. (1979) "Rate Constants for Reactions of Inorganic Radicals in Aqueous Solution," US Department of Commerce, National Bureau of Standards. pp. 1-55.
Saenz et al. (1999) "Ceramic Biomaterials: an Introductory Overview," Journal of Materials Education 21: 297-306.
Sakhalkar (2005) "Enhanced Adhesion of Ligand-Conjugated Biodegradable Particles to Colitic Venules," The FASEB Journal 1-19.
Sang et al. (2013) "A Microfluidic Technique for Generating Monodisperse Submicron-Sized Drops," RSC Advances 3 (7), 2330-2336.
Saunders et al. (1999) "Microgel Particles as Model Colloids: Theory, Properties and Applications," Advances in Colloid and Interface Science No. 80, 1-25.
Sawhney et al. (1993) "Bioerodible hydrogels based on photopolymerized poly (ethylene glycol)-co-poly (alpha-hydroxy acid) diacrylate macromers," Macromolecules. 26:581-587.

Scaiano et al. (2012) "Photochemical Norrish Type I Reaction as a Tool for Metal Nanoparticle Synthesis: Importance of Proton Coupled Electron Transfer," Chem. Commun. 48 (40), 4798-4808.
Scherzer et al. (2005) "Temperature Dependence of the Oxygen Solubility in Acrylates and Its Effect on the Induction Period in UV Photopolymerization," Macromol. Chem. Phys. 206 (2), 240-245.
Seliktar (2012) "Designing cell-compatible hydrogels for biomedical applications," Science. 336(6085):1124-1128.
Shih et al. (2012) "Cross-Linking and Degradation of Step-Growth Hydrogels Formed by Thiol-Ene Photoclick Chemistry," Biomacromolecules. 13(7):2003-2012.
Shiku et al. (2006) "Oxygen permeability of surface-modified poly (dimethylsiloxane) characterized by scanning electrochemical microscopy," Chem. Lett. 35(2):234-235.
Shim et al. (Mar. 2015) "Dynamic designing of microstructures by chemical gradient-mediated growth," Nature Communications 6, 6584. https://doi.org/10.1038/ncomms7584, 7 pp.
Shin et al. (Jun. 2014) "Photodegradable Hydrogels for Capture, Detection, and Release of Live Cells," Angew. Chemi. Int. 53(31): 8221-8224.
Sia et al. (2003) "Microfluidic devices fabricated in poly(dimethylsiloxane) for biological studies," Electrophoresis 24: 3563-3576.
Siltanen et al. (Apr. 2016) "Microfluidic fabrication of bioactive microgels for rapid formation and enhanced differentiation of stem cell spheroids," Acta Biomaterialia. 34:125-132.
Sivadas et al. (2011) "Inhalable, bioresponsive microparticles for targeted drug delivery in the lungs," Journal of Pharmacy and Pharmacology. 63:369-375.
Smaller et al. (1968) "Electron Paramagnetic Resonance Studies of Transient Free Radicals Produced by Pulse Radiolysis," Argonne National Lab, The Journal of Chemical Physics 48, 5174-5181.
Stadtman (2003) "Free radical-mediated oxidation of free amino acids and amino acid residues in proteins," Amino acids. 25(3-4):207-218.
Subramaniam et al. (Jan. 2016) "Hydroxyapatite-calcium sulfate-hyaluronic acid composite encapsulated with collagenase as bone substitute for alveolar bone regeneration," Biomaterials. 74:99-108.
Suh et al. (2011) "Using Stop-Flow Lithography to Produce Opaque Microparticles: Synthesis and Modeling," Langmuir. 27(2):13813-13819.
Tan et al. (2004) "Design of Microfluidic Channel Geometries for the Control of Droplet Volume, Chemical Concentration, and Sorting," Lab Chip 4 (4), 292-298.
Tan et al. (2005) "Microfluidic Separation of Satellite Droplets as the Basis of a Monodispersed Micron and Submicron Emulsification System," Lab Chip 5 (10), 1178-1183.
Tang et al. (2011) "A PDMS viscometer for assaying endoglucanase activity," Analyst. 136:1222-1226.
Teh et al. (2008) "Droplet Microfluidics," Lab Chip 8 (2), 198-220.
Thorsen et al. (2001) "Dynamic Pattern Formation in a Vesicle-Generating Microfluidic Device," Phys. Rev. Lett. 86:4163-4166.
Tsang et al. (2004) "Three-dimensional tissue fabrication," Advanced Drug Delivery Reviews. 56:1635-1647.
Turturro et al. (2013) "Kinetic Investigation of Poly(Ethylene Glycol) Hydrogel Formation via Perfusion-Based Frontal Photopolymerization: Influence of Free-Radical Polymerization Conditions on Frontal Velocity and Swelling Gradients," Macromolecular Reaction Engineering 7 (2), 107-115.
Vanapalli et al. (2008) "Fluidic Assembly and Packing of Microspheres in Confined Channels," Langmuir. 24:3661-3670.
Vegas et al. (Jan. 2016) "Long-term glycemic control using polymer-encapsulated human stem cell-derived beta cells in immune-competent mice," Nat Med. 22(3):306-311.
Vermue (1994) "Tetralin and oxygen transfer in the liquid-impelled loop reactor," Bioprocess Engineering. 11(6):224-228.
Weber et al. (2007) "The effects of cell-matrix interactions on encapsulated beta-cell function within hydrogels functionalized with matrix-derived adhesive peptides," Biomaterials. 28(19):3004-3011.
Weber et al. (2008) "Cell-Matrix Interactions Improve β-Cell Survival and Insulin Secretion in Three-Dimensional Culture," Tissue Engineering. 14A(12): 1959-1968.

(56) References Cited

OTHER PUBLICATIONS

West et al. (1999) "Polymeric Biomaterials with Degradation Sites for Proteases Involved in Cell Migration," Macromolecules 32 (1), 241-244.
Whittemore (1995) "A detailed analysis of hydrogen peroxide-induced cell death in primary neuronal culture," Neuroscience. 67(4):921-932.
Wiseman et al. (1996) "Damage to DNA by reactive oxygen and nitrogen species: role in inflammatory disease and progression to cancer," Biochemical Journal. 313(1):17-29.
Xia et al. (1998) "Soft Lithography," Annual Review of Materials Science. 28:153-184.
Xia et al. (Jun. 2016) "Oxygen-Purged Microfluidic Device to Enhance Cell Viability in Photopolymerized PEG Hydrogel Microparticles," Biomacromolecules. 17(7):2459-2465.
Xia et al. (Jul. 2017) "Cytocompatible Cell Encapsulation via Hydrogel Photopolymerization in Microfluidic Emulsion Droplets," Biomicrofluidics 11 (4), 044102-044111.
Yadavalli et al. (2004) "Microfabricated protein-containing poly(ethylene glycol) hydrogel arrays for biosensing," Sensors and Actuators B: Chemical. 97(2):290-297.
Yang et al. (2005) "The effect of incorporating RGD adhesive peptide in polyethylene glycol diacrylate hydrogel on osteogenesis of bone marrow stromal cells," Biomaterials. 26(30):5991-5998.
Yang et al. (Jul. 2016) "Spatially Patterned Matrix Elasticity Directs Stem Cell Fate," Proc Natl Acad Sci USA 113 (31), E4439-E4445.
Yu et al. (2001) "Photopolymerization behavior of di(meth)acrylate oligomers," Journal of Materials Science. 36:3599-3605.
Zhou et al. (Mar. 2015) "Core-Shell Microparticle Synthesis in Droplet Microfluidics Using a Single Step Polymerization," MEMS: 472-475.
Zhu (2010) "Bioactive modification of poly(ethylene glycol) hydrogels for tissue engineering," Biomaterials. 31:4639-4656.
Zhu et al. (2017) "Passive and Active Droplet Generation with Microfluidics: a Review," Lab Chip 17 (1), 34-75.

* cited by examiner

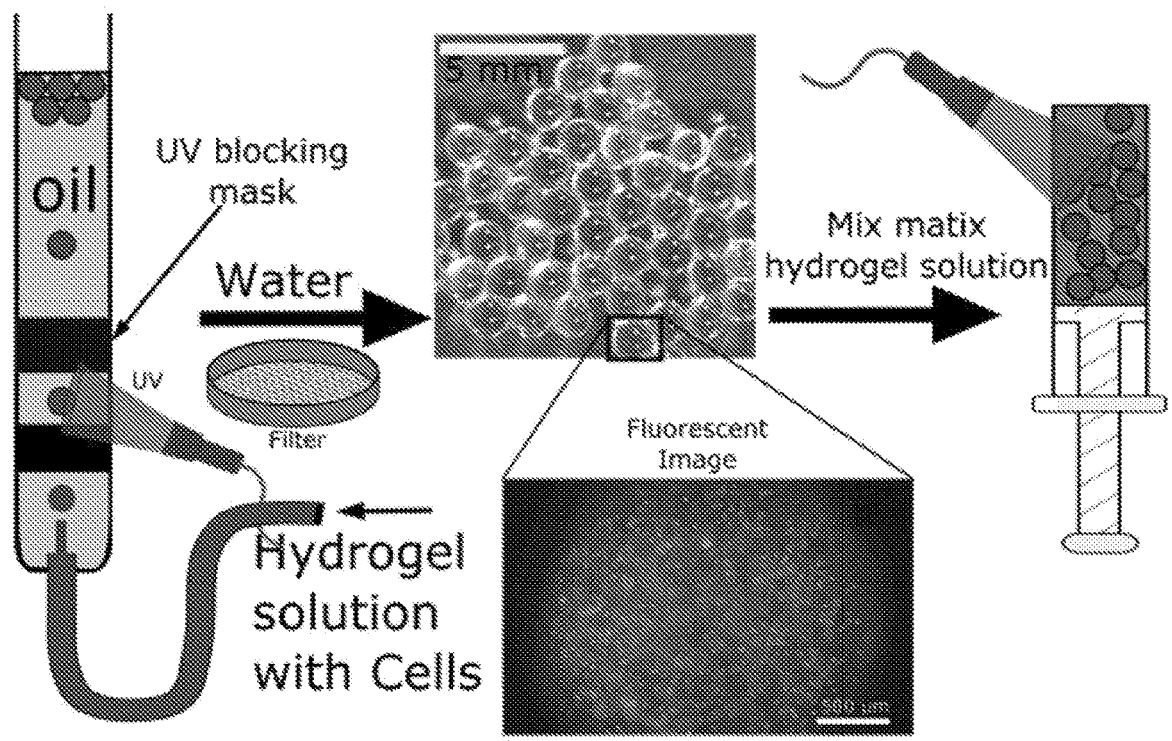
FIG. 24A  FIG. 24B
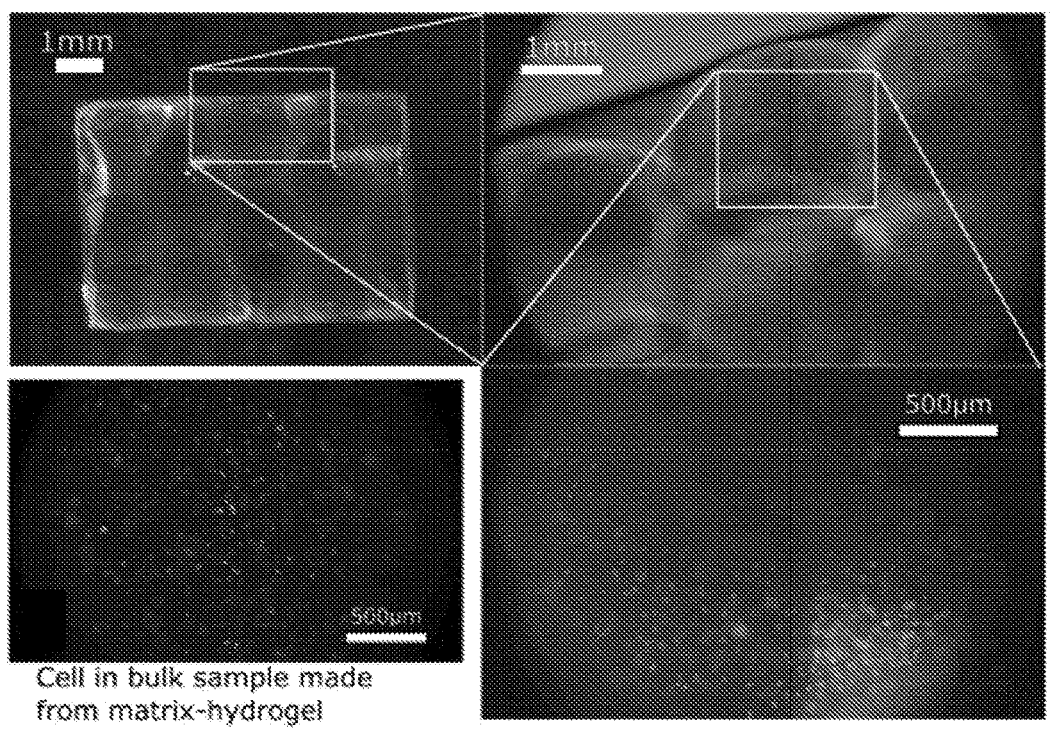
FIG. 24C  FIG. 24D
FIG. 24F  FIG. 24E

EXPLOITING OXYGEN INHIBITED PHOTOPOLYMERIZATION WITHIN EMULSION DROPLETS FOR THE FABRICATION OF MICROPARTICLES WITH CUSTOMIZABLE PROPERTIES

CROSS-REFERENCE TO RELATED APPLICATIONS

This application is a U.S. National Stage Application filed under 35 U.S.C. § 371 of International Application No. PCT/US2018/056237, filed Oct. 17, 2018, which application claims the benefit of U.S. Provisional Application Ser. No. 62/573,576 filed Oct. 17, 2017 and 62/586,680 filed Nov. 15, 2017, each of which is hereby incorporated by reference in its entirety, to the extent not inconsistent herewith.

STATEMENT REGARDING FEDERALLY SPONSORED RESEARCH OR DEVELOPMENT

This invention was made with government support under 1254608 awarded by the National Science Foundation (NSF) and under P20 GM103432 awarded by the National Institutes of Health (NIH). The government has certain rights in the invention."

BACKGROUND OF INVENTION

PEG-based hydrogels have become widely used as drug delivery and tissue scaffolding materials. Common among PEG hydrogel-forming polymers are photopolymerizable acrylates in the form of polyethylene glycol diacrylate (PEGDA). Microfluidics and microfabrication technologies have recently enabled the miniaturization of PEGDA structures, thus enabling many possible applications for nano- and micro- structured hydrogels. The presence of oxygen, however, inhibits the photopolymerization of PEGDA, which in turn frustrates hydrogel formation in environments of persistently high oxygen concentration. By developing an integrated model incorporating photoinitiation, reaction kinetics and oxygen diffusion, it is possible to utilize diffused oxygen to partially polymerize microdroplets, allowing for controlled generation of microparticles smaller than the microdroplet undergoing polymerization.

Photopolymerization also plays an important role in numerous industrial and research applications, including biomaterials for cell encapsulation and delivery. A common design of hydrogel materials for cell encapsulation is the use of diacrylated macromers. The presence of oxygen is known to inhibit the photopolymerization of PEGDA, but does not require mitigation on the macroscale reactions, and most notably, it limits polymerization carried out in air permeable polydimethylsiloxane (PDMS) microfluidic devices. As an example, we present innovative microfluidic devices using PDMS along with silicate or glass surfaces (which prevent the diffusion of oxygen) to further control the partial polymerization of PEGDA microdroplets.

Inverse colloidal crystals (ICCs) are the product of a lost wax fabrication method in which colloidal particles are assembled into ordered matrices in the presence of a liquid continuous phase. Following solidification of the continuous phase, particles are subsequently extracted, leaving behind a structured pore network. ICCs have been developed for a variety of scientific and technological applications, yet their utility remains limited by harsh processing conditions required to solubilize particles for pore framework formation. In this example, we present a new approach to ICC construction based upon photodegradable polyethylene glycol diacrylate particle synthesis. Because the degradation of particulate phase requires only optical illumination, particle assemblies can be eroded within tightly confining microchannels, creating microfluidic-integrated ICCs. Using this approach, photodegradable particle assemblies are used to pattern porous polyethylene glycol hydrogel network structure and interconnectivity. The non-invasive, gentle erosion of photodegradable PEG or PEGDA particles allows secondary objects to be embedded within the pores of the ICC. While the presence of oxygen may be harmful to biological particles present in the formation of the microparticles, precise control of the oxygen solubility and diffusivity may be used to generate an oxygen gradient in the microdroplet during polymerization, allowing for lower concentrations of oxygen in the polymerized microparticle. This approach is also facile, gentle and cytocompatible, indicating that it holds great potential for structuring functional biomaterials.

SUMMARY OF THE INVENTION

Described herein are methods and devices for the generation of hydrogel particles with micrometer and submicrometer dimensions using oxygen-inhibited partial polymerization, and the particles generated therefrom. The described methods are versatile, and may generate particles with dimensions independent of the starting polymerizable solution dimension, for example, a microdroplet. Further, microfluidic flow parameters (e.g. viscosity, flow rate) and photopolymerization process parameters (e.g. optical exposure intensity and duration) may be controlled to generate particles with tunable crosslinking density-determined properties including elasticity, diffusivity, and biomolecular display for diverse applications such as drug delivery, tissue engineering cell scaffolds, and single- and multiple- cell therapeutics. Similarly, gradients of crosslinking density-determined properties can be created within single particles through the selection of optical exposure intensity and duration. In addition to conventional spherical shapes, a suite of non-spherical shapes may be generated by manipulating the dimensions of the microfluidic channels and other related physical and process parameters.

The described methods and devices may control polymerization by manipulating various polymerization parameters such as initiator concentration, monomer or macromer concentration, oxygen concentration, oxygen diffusivity and oxygen solubility. All parameters may be controlled in both the microdroplet and the surrounding non-aqueous phase. In the case of photopolymerization using ultraviolet (UV) light, the intensity of the light and exposure time may also be varied for controlled polymerization, allowing for unique and variable microparticle properties including degree of cross-linking, size, surface elasticity and biocompatibility.

In an aspect, provided is a method of generating a plurality of microparticles comprising: a) providing a continuous phase comprising a non-aqueous liquid and a dispersed phase comprising an aqueous solution having a monomer or a macromer and a photoinitiator; b) forming a composition comprising microdroplets of the aqueous phase and the non-aqueous phase, wherein oxygen is diffused through the non-aqueous phase into the microdroplets; and c) partially polymerizing the aqueous phase thereby generating a microparticle within the aqueous phase having a smaller primary cross-sectional dimension than the microdroplet. In an embodiment, for example, the monomer or macromer comprises PEGDA and/or the photoinitiator is Irgacure 2959, LAP or a combination thereof. The aqueous phase may comprise 1% to 75%, 10% to 75%, or optionally, 10% to 50% monomer or macromer by weight. In embodiments, the aqueous phase comprises less than 10%, 0.1% to 10%, or optionally, 0.1% to 5% photoinitiator by weight.

The primary of the microparticle may be independent of the diameter of the microdroplet. The diffusion of oxygen into the microdroplet may generate an oxygen concentration gradient in the aqueous phase. After partial polymerization, the oxygen concentration gradient may result in a crosslinking gradient in the plurality of microparticles. Continuous crosslinking chain integration may be formed along the crosslinking gradient. The step of partially polymerizing the aqueous phase may be oxygen inhibited. The aqueous phase may comprise 1% to 99%, 1% to 50%, 10% to 50%, 20% to 75% or optionally, 20% to 50% monomer or macromer by weight. The aqueous phase may comprise 0.01% to 99%, 0.01% to 25%, 0.01% to 10%, or optionally, 0.01% to 5% photoinitiator by weight.

The non-aqueous phase may comprise a fluorocarbon oil or a hydrocarbon oil. The aqueous phase may have an oxygen concentration selected from the range of 0.1 mol/m$^3$ to 2 mol/m$^3$, 0.1 mol/m$^3$ to 1 mol/m$^3$, 0.5 mol/m$^3$ to 1 mol/m$^3$, 0.5 mol/m$^3$ to 2 mol/m$^3$, or optionally, 0.1 mol/m$^3$ to 0.5 mol/m$^3$. The non-aqueous phase may have an oxygen concentration selected from the range of 2 mol/m$^3$ to 5 mol/m$^3$, 2 mol/m$^3$ to 10 mol/m$^3$, 2 mol/m$^3$ to 3 mol/m$^3$, 1 mol/m$^3$ to 5 mol/m$^3$, or optionally, 1 mol/m$^3$ to 3 mol/m$^3$.

The aqueous phase may have an oxygen diffusivity selected from the range of 0.0001 mm$^2$/s to 0.01 mm$^2$/s, 0.001 mm$^2$/s to 0.01 mm$^2$/s, 0.001 mm$^2$/s to 0.1 mm$^2$/s, or optionally, 0.0001 mm$^2$/s to 0.001 mm$^2$/s. The non-aqueous phase may have an oxygen diffusivity selected from the range of 0.0001 mm$^2$/s to 0.05 mm$^2$/s, 0.0001 mm$^2$/s to 0.1 mm$^2$/s, 0.001 mm$^2$/s to 0.01 mm$^2$/s, or optionally, 0.001 mm$^2$/s to 0.05 mm$^2$/s.

The step of partially polymerizing the aqueous phase may be carried out by exposure to UV light. The exposure of UV light may be carried out for 1 ms to 1500 ms, 10 ms to 1000 ms, 1 ms to 1000 ms, or optionally 50 ms to 550 ms. The exposure to UV light may be carried out for less than 750 ms, 550 ms, 400 ms, or optionally, less than 250 ms.

The UV light may be provided at an intensity selected from the range of 0.01 mW/cm$^2$ to 3 mW/cm$^2$, 0.01 mW/cm$^2$ to 2 mW/cm$^2$, 0.1 mW/cm$^2$ to 3 mW/cm$^2$, or optionally, 0.1 mW/cm$^2$ to 2 mW/cm$^2$.

The aqueous phase and the non-aqueous phase may be formed in a microfluidic device. The described methods may further comprise flowing the microdroplets through one or more channels of the microfluidic device. The one or more channels may have a cross-sectional area less than or equal to 10000 µm$^2$, 5000 µm$^2$, 4000 µm$^2$, 2500 µm$^2$, or optionally, 1000 µm$^2$. Flowing the microdroplets through the one or more channels may generate non-uniform microdroplets, for example, non-spherical microdroplets.

The microfluidic device may comprise PDMS, glass or any combination thereof. The PDMS may have an oxygen concentration selected from the range of 4 mol/m$^3$ to 6 mol/m$^3$, 3 mol/m$^3$ to 5 mol/m$^3$, 4.5 mol/m$^3$ to 5.5 mol/m$^3$, or optionally, 4.5 mol/m$^3$ to 5 mol/m$^3$. The PDMS may have an oxygen diffusivity selected from the range of 0.01 mm$^2$/s to 0.05 mm$^2$/s, 0.001 mm$^2$/s to 0.1 mm$^2$/s, 0.01 mm$^2$/s to 0.1 mm$^2$/s, or optionally, 0.001 mm$^2$/s to 0.05 mm$^2$/s.

The microfluidic particle may have a primary cross-sectional dimension of less than or equal to 30 µm, 20 µm, 10 µm, or optionally, 5 µm. The microdroplets may have an average primary cross-sectional dimension of less than or equal to 200 µm, 100 µm, 75 µm, or optionally, 50 µm. The microdroplets may be substantially spherical. The microdroplets may be oblong, a disk, a biconcave disk, a torus, a rod, a wire, a bullet, a caterpillar or a horseshoe.

The microparticle may be bioactive. A surface of the microparticle may be treated with a biological material, for example, biotin. A surface of the microparticle may have increased bioactivity. The aqueous phase may further comprise a biological material.

In an aspect, provided is microparticle generated by the methods described herein.

In an aspect, provided is a microparticle comprising PEGDA having a primary cross-sectional dimension of less than or equal to 20 microns. In embodiments, for example, the microparticle is non-spherical and has a shape selected from the group comprising: oblong, a disk, a biconcave disk, a torus, a rod, a wire, a bullet, a caterpillar and a horseshoe.

In an aspect, provided is a method of preparing a composite hydrogel with comprising the steps of: a) providing a continuous phase comprising a non-aqueous liquid and a dispersed phase comprising an aqueous solution having a photodegradable monomer or a photodegradable macromer and a photoinitiator; b) forming a composition comprising microdroplets of the aqueous phase and the non-aqueous phase, wherein oxygen is diffused through the non-aqueous phase into the microdroplets; c) partially polymerizing the aqueous phase thereby generating a photodegradable microparticle within each of the microdroplets, each of the photodegradable microparticles having a smaller primary cross-sectional dimension than the microdroplet; d) removing excess aqueous phase from the photodegradable microparticles; e) at least partially encapsulating the photodegradable microparticles within a non-photodegradable polymer; and f) photodegrading the photodegradable microparticles to produce a composite porous hydrogel. The described methods may further comprise contacting the composite porous hydrogel with a biological material. The composite hydrogel may have pore shapes in any of the non-spherical microparticle shapes described herein.

The described method may further comprise a step of generating an oxygen concentration gradient in the aqueous phase. After partial polymerization, the oxygen concentration gradient may result in a crosslinking gradient along a physical dimension of the inverse hydrogel. Continuous crosslinking chain integration may be formed along the crosslinking gradient In an aspect, provided is a method for preparing an inverse colloidal crystal containing biological material comprising the steps of: a) providing a continuous phase comprising a non-aqueous liquid and a dispersed phase comprising an aqueous solution comprising a photodegradable monomer or a photodegradable macromer, the biological material and an initiator; b) forming a composition comprising microdroplets of the aqueous phase and the non-aqueous phase, wherein oxygen is diffused through the non-aqueous phase into the microdroplets; c) purging the composition comprising the microdroplets and the non-aqueous liquid with an oxygen-free gas; d) partially polymerizing the aqueous phase thereby generating a photodegradable microparticle within each of the microdroplets, each of the photodegradable microparticles having a smaller primary cross-sectional dimension than the microdroplet; e) removing excess aqueous phase from the photodegradable microparticles; f) at least partially encapsulating the photodegradable microparticles within a non-photodegradable polymer; and g) photodegrading the photodegradable microparticles to produce an inverse colloidal crystal having a plurality of pores containing a biological material. The inverse colloidal crystal may have pore shapes in any of the non-spherical microparticle shapes described herein The described method may further comprise a step of generating an oxygen concentration gradient in the aqueous phase. After partial polymerization, the oxygen concentration gradient may result in a crosslinking gradient along a physical dimension of the inverse colloidal crystal. Continuous crosslinking chain integration may be formed along the crosslinking gradient. Greater than or equal to 80%, 90%, or optionally 95% of the biological material may viable after performing the method.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 6A. For constant acrylate concentration, unpolymerized shell thickness varies considerably when changing PEGDA molecular weight from 700 to 575. FIG. 6B. Removing the inhibitor (MEHQ) from PEGDA 575 does not affect particle photopolymerization. FIG. 6C. Adding PEGMA while varying PEGDA concentration in order to maintain constant acrylate concentration yielded no change in unpolymerized shell thickness. FIG. 6D. Unreactive PEG400 changed particle size by modifying solution viscosity. ([LAP]=17 mM).

FIGS. 9A-9B. The model requires an empirically fitted diffusivity value to obtain a good prediction when varying PEGDA concentration and molecular weight, signaling the importance of molecular transport in the photopolymerized system. FIGS. 9C-9D. Model predictions closely match empirical data when changing initiator concentration, while kinetic differences between the two initiators were not as significant as previously reported.

FIG. 20A. Particles with gradient crosslinking density at surface leads to good interfacial bonding compared to particles with uniform and complete surface-crosslinking; FIG. 20B. composite with good interface shows stiffness similar to bulk hydrogel and significantly higher strength compared to composite with poor interface. FIG. 20B shows compression testing result of bulk and composite hydrogel samples made from PEG30 hydrogel.

FIG. 21A. Bulk hydrogel sample by bonding two parts at a 45° flat internal surface. The internal surface was fully polymerized if polymerized against glass or partially polymerized if polymerized against PDMS. FIG. 21B. Stress vs. Strain plots for bulk samples are shown beside samples made from two parts bonded at 45° surface. The bonded samples had bulk material similar elastic modulus but low failure strength and the PEG30 sample bonded at surface polymerized against glass was extremely weak.

FIG. 24A. Schematic of cell encapsulation in the particles from oil-column method; FIG. 24B. Fluorescent image shows very high cell viability (~90%) in the particles made by oil-column method. The green and red dots indicate live and dead cells respectively; FIG. 24C. Composite hydrogels made from cell-laden particles; FIG. 24D. Fluorescent image shows live and dead cells inside the particles surrounded by matrix material; FIG. 24E. Zoomed in fluorescent image of particles inside shows high cell viability is retained through the matrix polymerization step to fabricate composite hydrogel; FIG. 24F. As comparison to the composite, bulk matrix hydrogels shows very low cell viability.

(FIG. 34A) Quantified florescent Intensity, and (FIG. 34B) images of availability of functional sites on hydrogel particle surface. Top row and bottom row are images of the same particles under different light filters, with each column having the same exposure time (0.223 s, 0.294 s and 0.441 s, respectively).

FIGS. 37B and 37D represent zoomed in selection for oxygen concentration profile and extent of monomer conversion respectively, marked in FIGS. 37A and 37C as dotted squares. Model is highly sensitive to variations in oxygen diffusivity, resulting from changes in solution viscosity. Black dotted line in D represents the cut off extent of reaction under which no gelation is observed (Model parameters: $k_d$=0.005 s$^{-1}$, [M]=1 M, [PI]=17.0 mM LAP).

FIG. 39A Schematic illustration of hydrogel microparticle fabrication via oxygen-inhibited photopolymerization. FIG. 39B Micrographs illustrating the process described in FIG. 39A, with NA-Rh fluorescence imaging showing the presence of a radial crosslinking density gradient in the hydrogel network. Droplet content: 30 wt % PEGDA 700, 0.5 wt % LAP, 0.5 wt % Acryl-PEG-Biotin, exposed for 700 ms, 350 pW/cm².

DETAILED DESCRIPTION OF THE INVENTION

Figure 1:
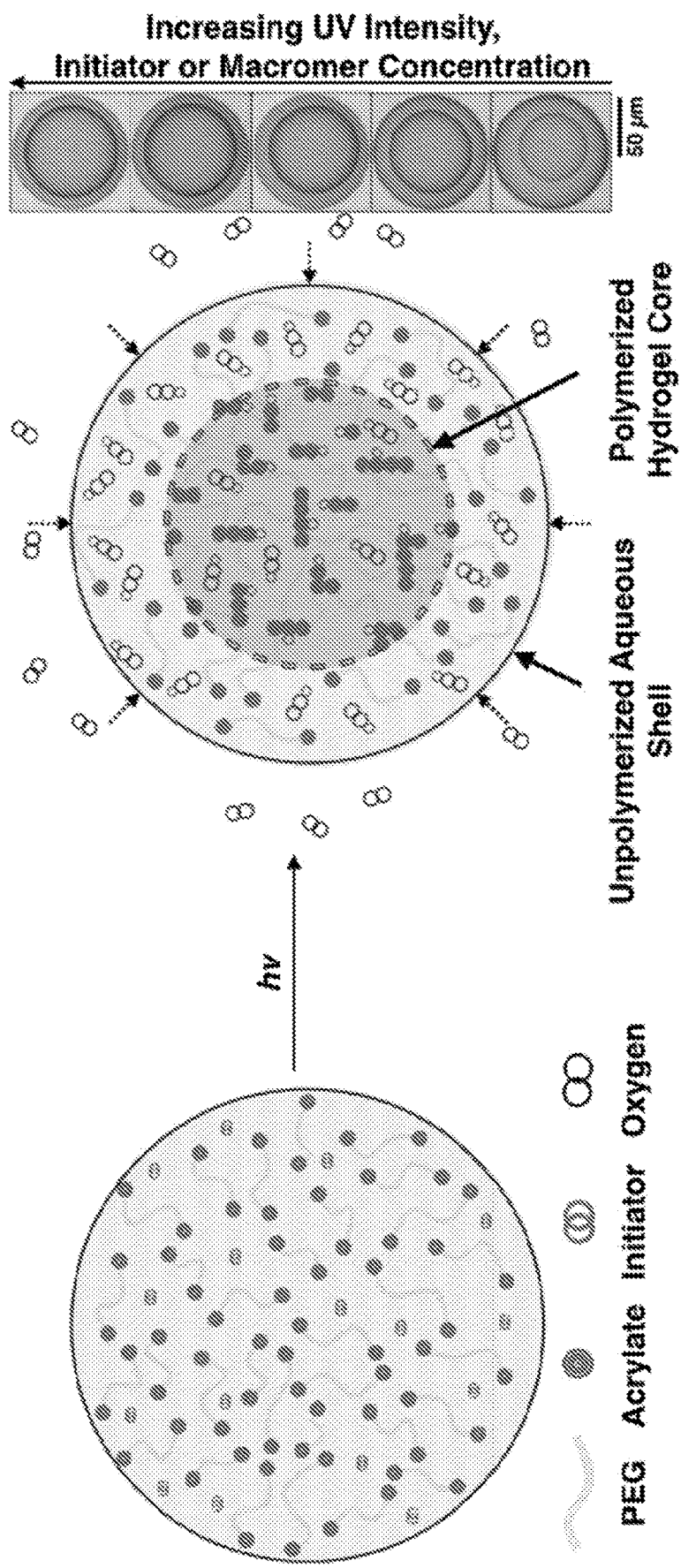
FIG. 1. provides an overview or graphical abstract of oxygen-inhibited photopolymerization.

In general, the terms and phrases used herein have their art-recognized meaning, which can be found by reference to standard texts, journal references and contexts known to those skilled in the art. The following definitions are provided to clarify their specific use in the context of the invention.

As used herein, the term "polymer" refers to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments greater or equal to 30 repeating units) and a high molecular weight (e.g. greater than or equal to 20,000 Da, in some embodiments greater than or equal to 50,000 Da or greater than or equal to 100,000 Da). Polymers are commonly the polymerization product of one or more monomer or macromer precursors. The term polymer includes homopolymers, or polymers consisting essentially of a single repeating monomer subunit. The term polymer also includes copolymers which are formed when two or more different types of monomers are linked in the same polymer. Useful polymers include organic polymers or inorganic polymers that may be in amorphous, semi-amorphous, crystalline or semi-crystalline states.

"Monomer" and/or "Macromer" each refer to a reagent which can undergo polymerization under appropriate conditions. A monomer or macromer reagent comprises at least one monomer or macromer molecule, where a monomer or macromer molecule is a molecule which can undergo polymerization, thereby contributing constitutional units to the structure of a polymer or oligomer. In an embodiment, a monomer or macromer reagent may be represented by an average or dominant chemical structure and comprise monomer molecules having that chemical structure but may also contain components with other chemical structures. For example, a monomer or macromer reagent may comprise impurities having chemical structures other than the average or dominant structure of the reagent. Macromer may refer to a reagent which is polymeric, e.g., has a number of repeating units but may further undergo polymerization to form a polymer of macromer repeating units. In embodiments, for example, macromer refers to reagents having a high molecular weight (e.g. greater than or equal to 200 Da, in some embodiments greater than or equal to 1000 Da or greater than or equal to 10,000 Da).

"Non-photodegradable polymer" refers to a polymer is that is not photodegradable under selected exposure conditions, e.g., selected wavelength range, intensity, power or a combination thereof. In an embodiment, for example, a non-photodegradable polymer refers to a polymer that does not degrade under the conditions present to degrade photodegradable polymers as described herein.

"Microparticles" refers to particles including polymers, having relatively small dimensions including diameter, radius, height, width, depth, etc. In embodiments, for example, microparticles refer to particles having a lateral dimension (e.g. diameter) of less than or equal to equal to 1 mm. In some embodiments, microparticles refers to particles having an average or mean diameter of less than or equal to 100 µm, less than or equal to 50 µm, or less than or equal to 20 µm. In some embodiments, microparticles are microspheres. In some embodiments, microparticles refer to particles having lateral dimensions selected from the range of 10 nm to 1000 µm, preferably for some embodiments, 10 nm to 100 µm.

"Microdroplets" refer to microparticles in the liquid phase. As described herein, microdroplet dimensions may be larger than the corresponding generated microparticle, as only a portion of the microdroplet is polymerized. For example, in some embodiments, microdroplets refer to droplets having a mean or average diameter of less than or equal to 500 µm, less than or equal to 100 µm, or less than or equal to 50 µm. In embodiments, microdroplets refer to liquids in a suspension, for example an emulsion. In an embodiment, microdroplets refer to aqueous liquids suspended in a non-aqueous liquid. In some embodiments, microdroplets refer to particles having lateral dimensions selected from the range of 10 nm to 1000 µm, preferably for some embodiments, 10 nm to 100 µm.

"Hydrogel" refers to an at least partially hydrophilic substance having characterized by high water absorbency. In embodiments, hydrogel comprises an at least partially hydrophilic polymer, superabsorbent polymer or biomacromolecule, for example in a network configuration. Hydrogels may be characterized as a water swollen but insoluble substance. In embodiments, for example, hydrogels may absorb water greater than or equal to 10 times the hydrogel weight, greater than or equal to 50 times the hydrogel weight or, optionally, greater than or equal to 100 times the hydrogel weight.

"Primary cross-sectional dimension" refers to the largest cross-sectional dimension of a particle as described herein. For example, for a sphere the primary cross-sectional dimension is a diameter, while for a cylinder or a wire the primary cross-sectional dimension is the diameter of the cross-sectional circle or ellipse at the widest point along the axial length. Similarly, primary cross-sectional dimension may refer to the effective diameter of the cross-section of the described shape or particle.

Example 1—Precise Control of PEGDA Hydrogel Particle Size by Oxygen Inhibited Photopolymerization within Microfluidic Droplets Abstract Hydrogels based on poly(ethylene glycol) (PEGDA) have been engineered for a variety of biomedical applications including drug delivery, cell delivery, and tissue engineering. The miniaturization of these materials to nanoscale and microscale particles has been a subject of intense activity, and promises to extend their range of applicability. In general, however, these efforts have been frustrated by the inhibition of chain growth polymerization by oxygen, an effect that is exacerbated as target length scales are reduced. Here, we report a method that exploits the undesirable oxygen-inhibited photopolymerization to produce size-controlled PEGDA hydrogel particles. The role of initial solution composition on resultant particle size is reported, and is found to contribute through its influence on the polymerization rate, as well as the diffusivity of oxygen. By controlling photopolymerization kinetics facilely via UV light intensity and/or exposure time, PEGDA particles were produced with dimensions independent of the parent spherical droplets formed by conventional microfluidic emulsification.

Introduction

Biomaterials, such as polymers,[1] ceramics,[2] and metals[3] are widely used in biomedical diagnostic, therapeutic, and prosthetic applications. Among these, hydrogels, defined as water-swollen, cross-linked hydrophilic polymer gels, have shown great potential for biological and medical applications.[4] Synthetic hydrogels have become a focus of particular interest in the last twenty years due to their well-defined structure that can be modified to add functionality and programmed degradability.[5] In particular, hydrogels of poly(ethylene glycol) diacrylate (PEGDA) have been investigated for tissue engineering[6,7] and drug delive[8-11] applications because of their biocompatibility, non-immunogenicity, resistance to protein adsorption, and adjustable mechanical properties and chemical composition.[12,13] Functional hydrogels can be tailored to possess well-defined permeability and stiffness,[14] to be sensitive to temperature,[15] and to degrade hydrolytically,[16,17] photolytically,[18,19] or enzymatically.[20] Among the advantages of PEGDA, its ability to be photopolymerized is most notable, as it lends spatial and temporal control over hydrogel properties,[21] adding to its versatility and convenience.[22]

Hydrogels are typically formulated as bulk structures, such as films and monolithic molds, but emerging applications demand miniaturization for delivery and transport in microscopic environments.[23] In comparison to traditional polymeric nanocarriers such as micelles, liposomes, and polymerosomes, hydrogel particles in the micron and submicron size range offer many advantages, such as controlled loading, versatility in material composition and type of biological cargo, and physical stability.[24] These particles have been previously synthesized by bulk emulsion and dispersion polymerization, which result in a highly polydisperse particle size distribution.[25] More recently, droplet microfluidic particle templating has gained popularity due to its accurate control over particle size and dispersity.[28] Droplet-based microfluidic systems utilize two flowing immiscible phases, usually in combination with a stabilizing surfactant, to form discrete droplets at a channel junction via interfacial instabilities.[27] The size of formed droplets depends upon viscous forces, surface and interfacial chemistry, and channel geometry. However, while droplets in the 10-60 μm range have been reliably produced,[28] droplet production for <10 μm or even submicron is still challenging due to the high shear energy required to overcome the interfacial forces in aqueous solutions.

Microfluidic methods such as tipstreaming in a flow focusing device,[29,30] electrospraying,[31] satellite droplet collection,[32] and droplet shrinking[33,34] have been used to obtain submicron droplets. However, these methods all possess shortcomings that constrain their utility. Tipstreaming, for instance, requires a high viscosity ratio between the immiscible phases and high surfactant concentrations. As a result, it is very sensitive to pressure fluctuations, and fails when using aqueous solutions with high macromer concentrations due to viscoelastic memory effects. Electrospraying requires high energy input and very high flow rate ratios, and is dependent upon the conductivity of the liquids used. Moreover, none of these methods have been coupled with in situ photopolymerization to continually produce hydrogel particles, resulting in decreased monodispersity as a consequence of random droplet coalescence during the collection process.

Photopolymerization of PEGDA droplets in microfluidic devices has experienced limited adoption due to challenges arising primarily from oxygen inhibition effects. The inhibition of PEGDA photopolymerization occurs as a result of the rapid reaction of oxygen with photoinitiator and propagating monomer radicals to form peroxides, resulting in no or incomplete polymerization where oxygen is present in surplus.[35-38] All acrylates are inherently vulnerable to oxygen inhibition, and thus, dissolved oxygen must be almost completely consumed before the polymerization reaction can occur. In the case of PEGDA, the consumption of oxygen results in an induction period before which no PEG macromer is converted to cross-linked hydrogel.[39] At oxygen rich interfaces, a competition occurs between the photopolymerization reaction and oxygen diffusion due to the replenishment of oxygen. This is particularly relevant to the photopolymerization of thin films.° and within gas permeable polydimethylsiloxane (PDMS) microfluidic devices.[41,42] Attempts to counteract the effects of oxygen inhibition include oxygen scavengers, reducing agents, potent photoinitiators, and purging with an inert gaS.[43,44] It is possible to photopolymerize emulsion droplets flowing within PDMS microfluidic channels by implementing one or more of these methods, but they either increase the complexity of the microfluidic device design or require adding reactive chemical species into the system, which is generally undesirable for biomaterials applications.

Figure 2A:
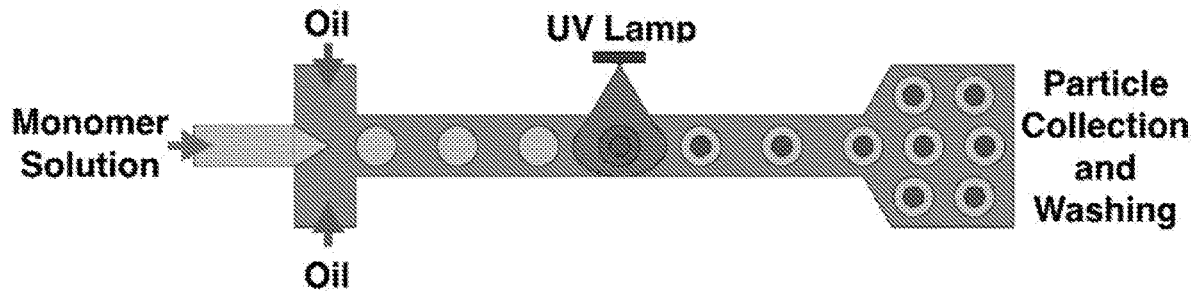
FIG. 2A. Schematic of droplet formation and continuous photopolymerization of oxygen-inhibited PEGDA.
Figure 2B:
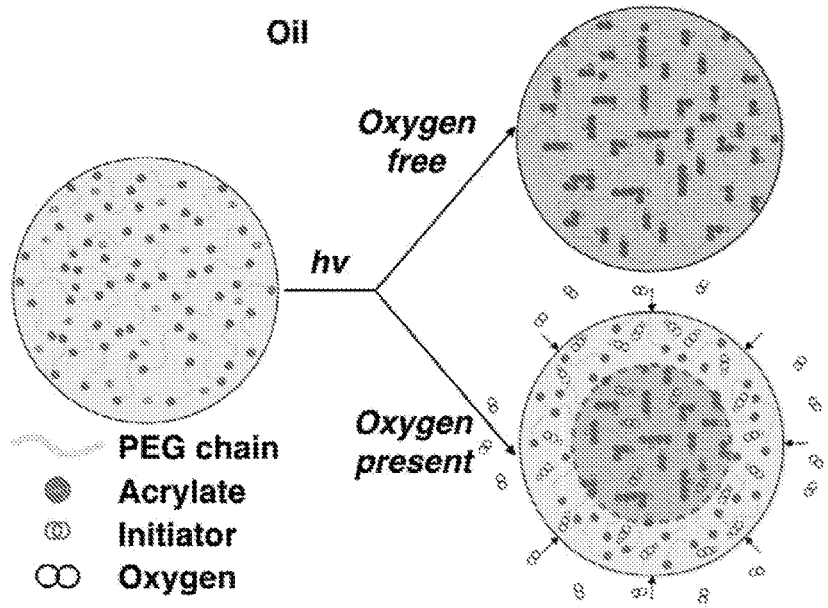
FIG. 2B. Photopolymerization proceeds within the droplet in an oxygen-dependent manner, starting at the droplet center and ceasing where the steady state oxygen concentration rises above the inhibition threshold.
Figure 2C:
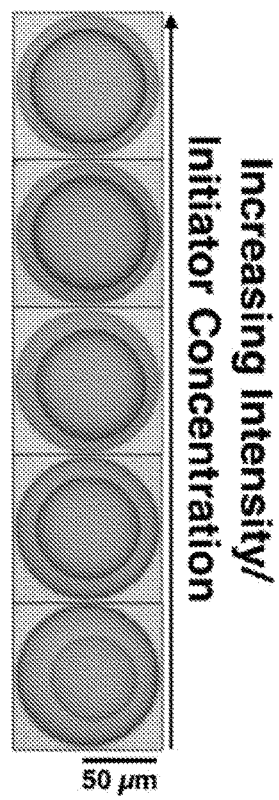
FIG. 2C. Imaged droplets after photopolymerization reveal a sharp contrast at the hydrogel particle boundary.

While oxygen inhibition is generally regarded as undesirable, stop flow lithography[45] and gradient-mediated photopatterning techniques[46] have exploited the presence of oxygen in microfluidic devices to obtain uniquely shaped particles. In droplet microfluidics, the oxygen inhibition effect can be observed at the interface between aqueous droplets and the surrounding oil. As reported by the co-author's group, this effect is pronounced when using oils with high oxygen solubility and diffusivity, as they provide a constant flux of oxygen to the droplets. Upon UV exposure, spherical hydrogel particles are polymerized at the droplet center and are surrounded by an unpolymerized shell, the thickness of which has been shown to be independent of the total droplet diameter.[47] This behavior, arising from equal rates of oxygen reaction and diffusion, presents a unique platform to obtain hydrogel particles with smaller diameters than that of the droplet. FIG. 2 schematically describes droplet photopolymerization in a microfluidic channel with oxygen present and illustrates how a single process parameter can be manipulated to vary particle size within uniformly sized droplets. In this paper, we have quantified the effect of different photopolymerization parameters, including the UV dose and macromer solution composition, on the unpolymerized shell thickness. This platform also allows the study of droplet photopolymerization kinetics by coupling empirical results with a reaction-diffusion model to quantify the sensitivity of each variable upon the photopolymerization of hydrogel particles within microfluidic emulsion droplets.

Kinetic models for the photopolymerization of multifunctional acrylates have been previously developed to accurately describe the effect of oxygen inhibition on polymer coatings, membranes,[48,49] and thin films.[50] These models have been adapted to microfluidic contexts to describe and predict the size of a particle produced via stop flow lithography in microfluidic devices under different exposure conditions[45] and to explain the presence of an unpolymerized shell around a hydrogel particle when photopolymerizing droplets in ambient conditions.[47] By understanding the influence of each parameter in the hydrogel photopolymerization process, we can exploit oxygen inhibition to produce particles that are <10 μm or submicron from larger, easily produced droplet templates.

As described herein, we perform a systematic characterization of the effects of hydrogel-forming parameters on oxygen-inhibited PEGDA photopolymerization within emulsion droplets. The presented reaction-diffusion model accurately captures stoichiometric and photochemical effects on polymerization rate, and incorporates a previously unappreciated relationship between solution viscosity and oxygen diffusivity. Having produced a reaction-diffusion model that completely describes the full range of empirical results presented here, we have developed a quantitatively comprehensive and predictive understanding of PEGDA photopolymerization within flowing emulsions. This result has broad implications for the continuous production of biocompatible hydrogel particles and the high-throughput encapsulation of biomolecules.

Experimental (Materials and Methods)

Hydrogel forming solutions: Solutions containing poly (ethylene glycol) diacrylate (PEGDA 700 and PEGDA 575, Aldrich Chemistry) in deionized water were prepared and used as the dispersed phase. Poly(ethylene glycol) monoacrylate (PEGMA 400, PolySciences Inc.) and poly(ethylene glycol) (PEG 400, Aldrich) were added to alter acrylate concentration and solution viscosity. Monomethyl ether hydroquinone (MEHQ) was removed from PEGDA 575 with a prepacked adsorption column (Aldrich Chemistry).

Two initiators were tested separately: 2-hydroxy-4'-(2-hydroxyethoxy)-2-methylpropiophenone (Irgacure 2959, Aldrich Chemistry) and lithium phenyl-2,4,6-trimethylbenzoylphosphinate (LAP), which was synthesized as previously described.[51] Irgacure 2959 has been a widely used photoinitiator due to its moderate water solubility and biocompatibility, while LAP is quickly becoming a popular option due to its enhanced absorption at higher wavelengths and higher cytocompatibility.[22] Initiator was incorporated from 0.1-0.5% (LAP) and 2-4% (Irgacure 2959), as indicated.

Microfluidic device design and operation: A single layer, flow focusing microfluidic channel configuration was used to form droplets within a continuous phase, Novec 7500 with 2% Picosurf surfactant (Dolomite Microfluidics). Fluorocarbon oils have been used in droplet microfluidics because their low viscosity, high density, and high volatility facilitate droplet production and recovery relative to mineral oil.[52] Droplets were produced in a 50 μm deep channel, pinching droplets in a 40 μm wide and 250 μm long nozzle, and flowed downstream to a 110 μm deep and 200 μm wide straight channel, in which their velocity was reduced to allow longer UV exposure times. Droplet diameter was set at ~100 μm by setting the dispersed phase flow rate to 5 μl/hr, while the continuous phase flow rate was set to 40 μl/hr and 30 μl/hr in the droplet formation section and the downstream section, respectively. Two-layer microfluidic devices were fabricated using common soft lithography techniques.[53] Briefly, a silicon wafer (Silicon Inc. USA) was first patterned with SU-8 3050 negative photoresist (MicroChem, MA, USA) at a thickness of 50 μm. Features were polymerized by collimated UV light exposure (Omnicure S2000, USA) through a photomask (CAD/Art Services, OR), and hard baked for 1 minute at 65° C. and 3 minutes at 95° C. A second planar flow network was patterned with SU-8 3050 at thickness of 60 μm (for a total of 110 μm) by the same method, and after a second hard baking for 1 minute at 65° C. and 4 minutes at 95° C., the uncured photoresist was removed using a developer (propylene glycol monomethyl ether acetate, Sigma-Aldrich, USA).

Polydimethylsiloxane (PDMS, Sylgard 184, Dow Corning, MI) was poured upon the silicon wafer and cured in a 70° C. oven for 4 hours. The elastomer replica was removed, trimmed, and punched with a sharpened 20 G dispensing needle (Brico Medical Supplies, Inc., USA) to fashion inlet and outlet holes. To ensure a hydrophobic surface for aqueous droplet generation, Aquapel (PPG Industries) was injected into the device and flushed with nitrogen. Omitting this step allowed aqueous droplets to adhere to the channel walls, altering flow patterns within device. PEGDA solutions and oil were loaded into disposable plastic syringes (1 ml, Becton Dickinson) and the flow of each component was independently controlled by syringe pumps (Nemesys syringe pump, Cetoni, Germany). Fluidic inlets and outlet on the PDMS microfluidic device were connected to fluid sources and collection reservoirs, respectively, via microbore Tygon tubing (0.01" ID×0.03" OD, ND-100-80, United States Plastic Corp).

Photopolymerization: An inverted microscope (IX71, Olympus) and a 20×objective (Olympus LUCPlanFLN 0.45Ph1) were used for imaging droplets. An X-Cite 120LEDmini (Excelitas Technologies) fluorescent illumination system was used to provide white light, which was filtered through a DAPI filter cube for photopolymerization. Since this light source is not monochromatic, the intensity spectral output was measured using a LumaSpec 800 Optical Power Meter (Prior Scientific) (see FIG. 35). An LED light source was utilized for photopolymerization due to its short-term and long-term stability and easily varied intensity. The total channel area exposed to UV light was determined by flooding the device with only the hydrogel forming macromere solution, assuring that the fluid was quiescent, and exposing the channel to UV using the 20×objective. After 10 seconds of exposure, a lower magnification objective and a Brightfield filter cube were used to image the polymerized structure. Using ImageJ, the diameter of the UV exposure area was determined from the dimensions of the structure, and later used in conjunction with the cross-sectional area and flow rate to determine exposure time, which under the previously indicated flow rate was 1.2 s.

Droplets traveling along the channel were polymerized by exposure to UV light at discrete intensities. Images of exposed droplets were acquired after the droplets were collected in a downstream reservoir (FIG. 2A) and later processed using ImageJ to determine droplet size, particle size, and unpolymerized shell thickness. The polymerized core of the droplets has a significantly different refractive index (see FIG. 2C) than the macromer solution, enabling polymerized particles and total droplet diameters to be easily measured.

Viscosity and solubility measurements: Oxygen solubility was measured using an Orion Star A113 Dissolved Oxygen Benchtop Meter and a 083005MD Orion polarographic dissolved oxygen sensor. Viscosity was measured using a Brookfield LVDV-E Laboratory Viscometer and a UL closed tube adapter.

Results and Discussion

A reaction-diffusion model has been developed to predict hydrogel structure formation by quantitatively comparing PEGDA photopolymerization kinetics and oxygen diffusion within droplets flowing through PDMS microfluidic channels. This model was validated and optimized through a series of systematic experiments in which process parameters were varied and the relative diameters of polymerized particles and the surrounding unpolymerized shell thickness were measured within a droplet of arbitrary diameter. The results presented here are reported as unpolymerized shell thickness as opposed to particle size because it has been shown that the former is a direct function of reaction kinetics and oxygen diffusion, whereas the latter is the geometric product of the unpolymerized shell thickness and the droplet size.[47] As such, using unpolymerized shell thickness allows these results to be extrapolated to photopolymerization within arbitrary sized droplets in order to obtain particles with specific sizes. To accurately relate polymerization kinetics to unpolymerized shell thickness, experimental measurements must be acquired under steady state conditions. Steady state is achieved when the oxygen profile throughout the droplet no longer changes with time, indicating an equivalence of oxygen consumption and diffusive flux at a fixed radial position. Additionally, an oxygen saturation boundary condition is assumed in order to establish the oxygen flux across the droplet interface, from the oil phase to the aqueous phase. To confirm that steady state had been reached in our experiments, and to verify the saturated oxygen boundary condition, a set of preliminary experiments were first conducted.

The exposure time required to reach steady state was determined by tracking the photopolymerization of PEGDA and photoinitiator containing emulsion droplets in a quiescent reservoir over a period of several seconds. The results, summarized in FIG. 3, show that the exposure time required to reach steady state depends strongly upon UV intensity, and that lower UV intensities yield larger unpolymerized shells and thus smaller particles from uniformly sized droplets. These results are consistent with the hypothesis that the thickness of the unpolymerized shell is proportional to the ratio of oxygen diffusion and consumption rates. Above a minimum threshold exposure time visible hydrogel particles appear and while their diameter does not change with increasing exposure time, the degree of crosslinking does continue to increase, as determined by the change in refractive index of the polymerized gels. This exposure time, described previously as the induction time, is the sum of the time required for the local oxygen to be depleted and the time necessary for the oligomer to be cross-linked into a gel. For multifunctional oligomers, gelation occurs at about 1-2% double bond conversion.[54] This simplifies data collection, as there is no risk of underexposing and not reaching steady state particle size.

Figure 3A:
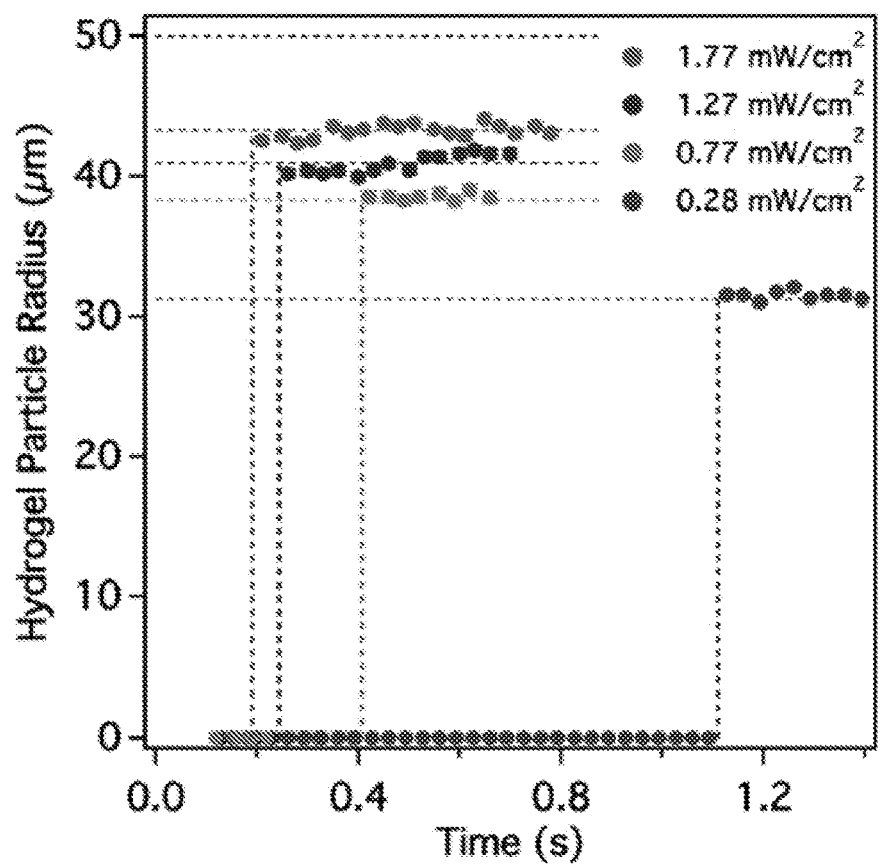
FIG. 3A. Plot of hydrogel particle radius as a function of exposure time and intensity. Dashed horizontal lines indicate particle radii at a given intensity after 30 s of UV exposure. Particles appear following an induction time, indicated by vertical dotted lines, after which their size remains constant. ([PEGDA 700]=0.5M, [LAP]=17 mM) FIG. 3B. Images of a droplet being photopolymerized in a microfluidic channel at different exposure times. Longer exposure times result in a visible increase in crosslinking, while the particle diameter (blue lines) remains constant. ([PEGDA 700]=0.3 M, [LAP]=17 mM, I=1.77 mW/cm$^2$)
Figure 3B:
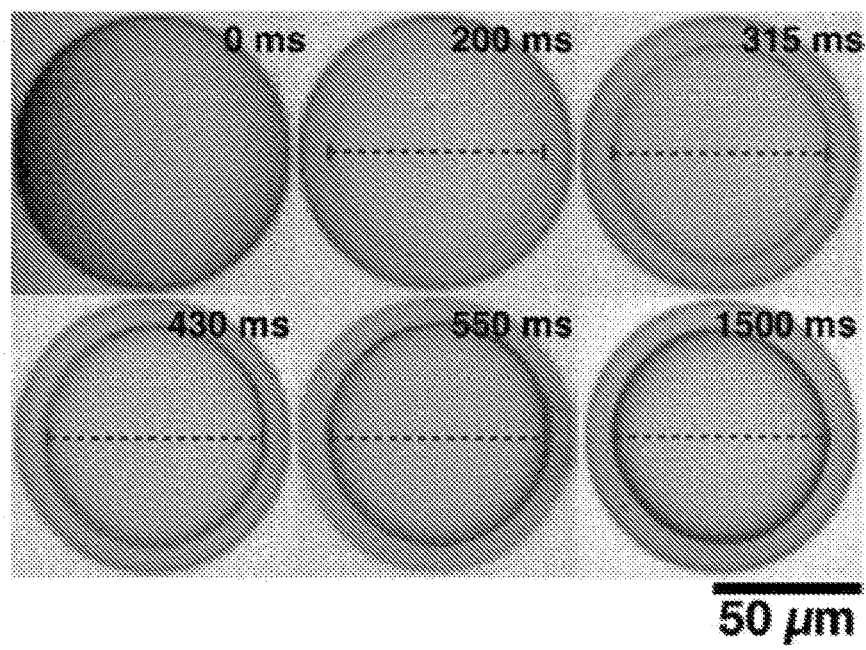

FIG. 3 also illustrates that UV intensity is a key variable that impacts photopolymerization kinetics. Intensity can be easily changed with either neutral-density filters or variable light attenuation controls in the illumination system. To demonstrate the range of particle sizes that can be obtained for a given solution of constant composition, all the experiments were conducted over a range of intensities from 0.19 to 1.77 mW/cm$^2$. A logarithmic trend was observed in all experimental data sets, in which the unpolymerized shell thickness displayed minor variation at higher intensities, while increasing drastically at lower intensities. These results suggest that in order to photopolymerize small particles from a larger droplet size, it is necessary to operate at relatively low UV intensities. It is worth noting that induction times are longer at lower intensity, therefore requiring longer exposure times (FIG. 3A) and a highly stable and well-controlled UV source. Thus, to reliably produce small particles, it is easier to polymerize smaller droplets at a higher intensity. Furthermore, FIG. 3B illustrates qualitatively that it is possible to vary the degree of crosslinking by changing exposure time.[55] The relative effects of UV exposure intensity and time are further described herein.

Figure 4A:
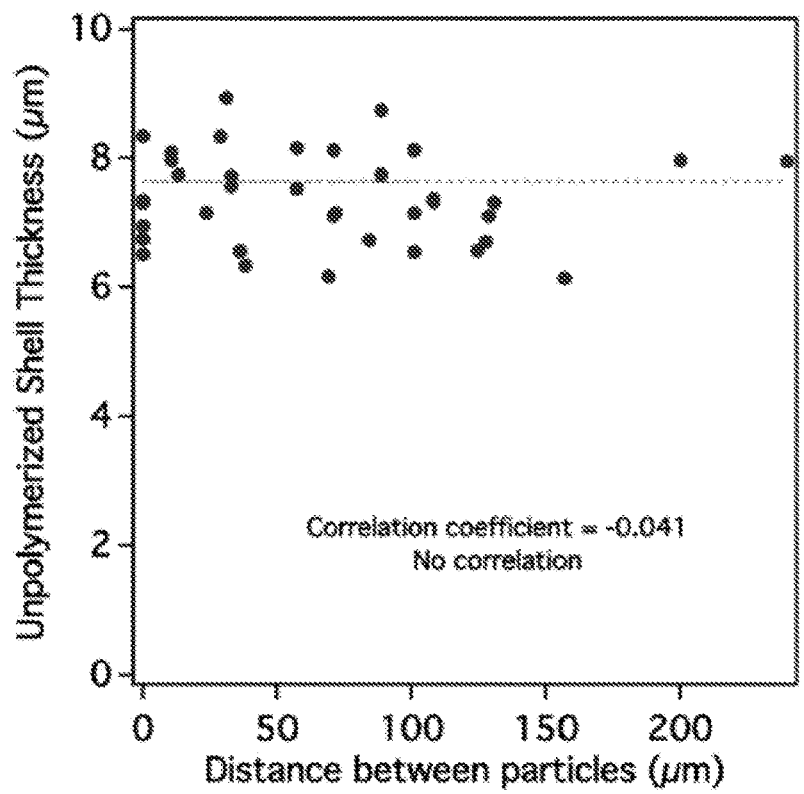
FIG. 4A. Emulsion droplets within fluorocarbon oils maintain a constant interfacial oxygen concentration during photopolymerization. Blue dots represent individual data points for the unpolymerized shell thickness in droplets at a given distance from the nearest aqueous droplet. Dotted red line indicates unpolymerized shell thickness in droplets polymerized under flow conditions (u=990 µm/s, Re=0.177). ([PEGDA 700]=0.5 M, [LAP]=17 mM, I=1.77 mW/cm$^2$) FIG. 4B. Experiments to assess kinetic parameters and their effect upon steady state hydrogel particle size were conducted in quiescent reservoirs, which match continuous flow conditions. ([PEGDA 700]=0.5 M, [LAP]=17 mM).

Effect of spacing on oxygen boundary conditions: Oxygen concentration boundary conditions at the droplet-oil interface were determined by exposing randomly positioned, variable spaced droplets in a microfluidic reservoir. As shown in FIG. 4A, there is no correlation between spacing and shell thickness, even when the droplets are in direct contact with other aqueous droplets. This indicates that no oxygen concentration gradient exists in the oil surrounding the droplet; instead, the high oxygen diffusivity and solubility of the oil maintain a constant oxygen concentration at the droplet boundary.

Figure 4B:
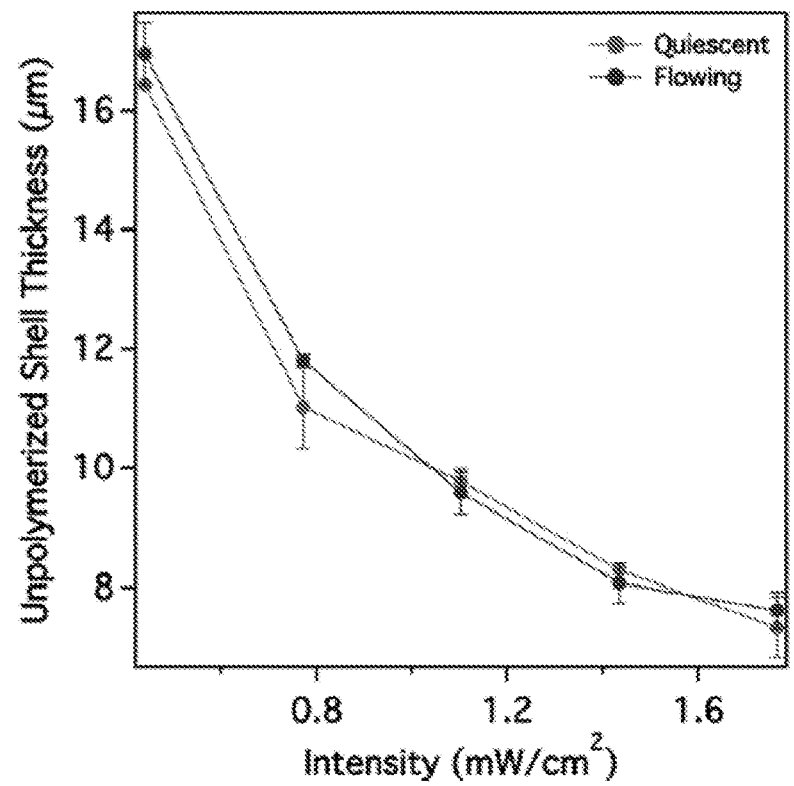

Effect of flow: Photopolymerization under flow was suspected to possibly affect the extent of droplet photopolymerization, as convective fluid motion outside and within the droplet can enhance the transport of chemical species. While external transport was shown to be inconsequential due to the high diffusivity of oxygen through fluorocarbon oil, recirculating flows within the droplet could potentially enhance convective mixing and thus the transport of reactive species throughout the droplet. Significant convective mixing, in addition to diffusive oxygen transport, would modify the resulting unpolymerized shell thickness. To establish whether the effect of convective transport must be considered, experiments were carried out using the same droplet composition under laminar flow (Re=0.177) and under quiescent conditions. The results show that there is no impact of flow on unpolymerized shell thickness (FIG. 4B) under the specified flow and exposure conditions. Therefore, for short exposure times (t<1.2 s), internal convection can be neglected within droplets flowing in linear channels operating under laminar conditions. In the experiments conducted, an exposure time of 1.2 seconds was generally sufficient to observe particle gelation in the intensity range used for photopolymerization (0.19 to 1.77 mW/cm$^2$).

Effects of PEGDA concentration, chain length and molecular weight: For biomedical applications, the diffusion of different sized solutes through a hydrogel is a basic design criterion that can be tailored by changing macromolecular architecture and crosslinking density.[57] The mesh size, tensile strength, and swelling ratio for a given PEGDA hydrogel particle can all be tuned by using PEGDA macromers with varying molecular weight and concentration in solution, and by controlling the degree of crosslinking.[14,55] Therefore, it is important to determine the impact of these variables on droplet photopolymerization kinetics and resulting particle size.

Figure 5:
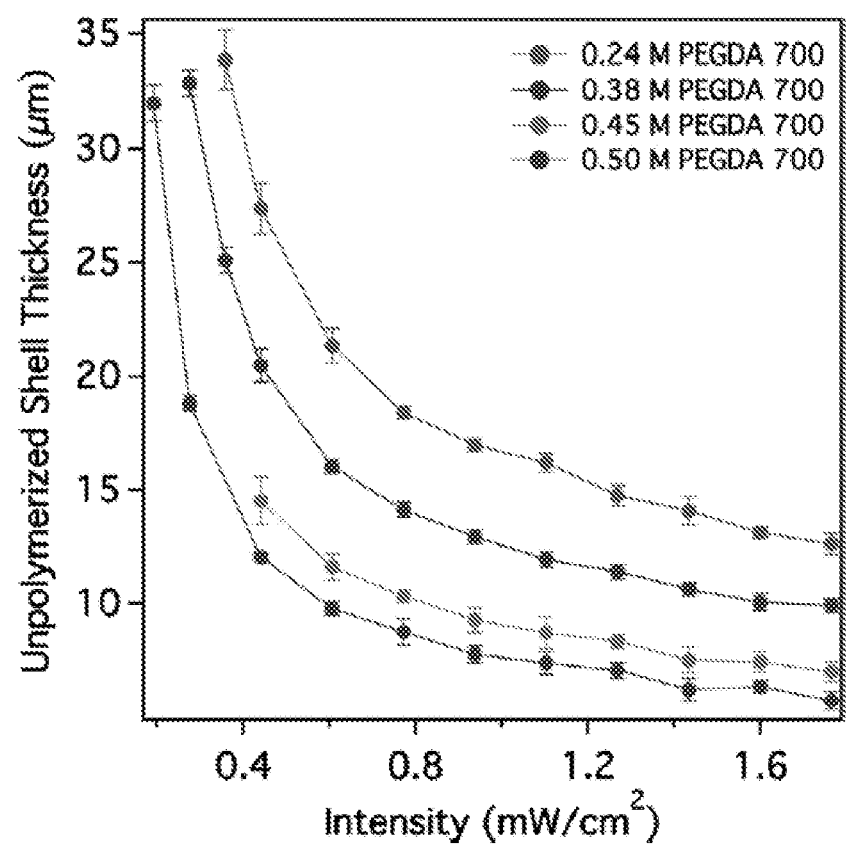
FIG. 5. Acrylate functional group concentration contributes to the regulation of unpolymerized shell thickness. Decreasing PEGDA concentration produces a clear trend toward larger thicker unpolymerized shell, which highlights its ability to vary the rate of oxygen consumption and, in turn, the diameter of photopolymerized particles. ([LAP]=17 mM).

To determine the effect of acrylate functional group concentration on unpolymerized shell thickness, four different concentrations of PEGDA 700, corresponding to 20, 30, 35, and 40 wt %, in combination with 17 mM LAP were exposed over a range of UV light intensity. The results (FIG. 5) show that higher concentrations of PEGDA 700 yield particles with a smaller unpolymerized shell thickness. We hypothesize that this correlation is attributable to the increasing density of acrylate functional groups at higher PEGDA concentration, which accelerates the propagation of polyacrylate chain growth and crosslinking. Faster polymerization kinetics push the polymerization boundary closer to the interface, resulting in thinner steady state shell thicknesses.

Figure 6A:
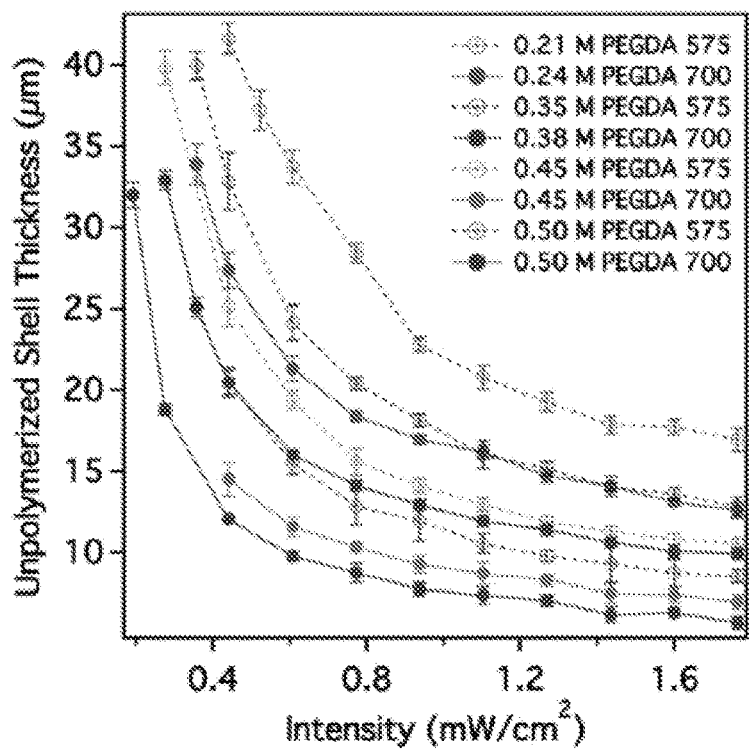
FIGS. 6A-6D. PEG architecture and acrylate concentration regulate unpolymerized shell thickness.

The effect of PEGDA chain length on photopolymerization kinetics was determined by replacing PEGDA 700 with a lower average molecular weight PEGDA molecule (575). Based solely upon photopolymerization kinetics (Equations 3-6), reaction rates are functions of the acrylate functional group concentration, which react to generate propagating radicals. Chain length is therefore not predicted to affect particle size if the concentration of acrylate functional groups is held constant. To achieve constant acrylate concentration, the PEGDA mass fraction was scaled in proportion to the length of the PEG chain. Four different concentrations of PEGDA 575, corresponding to 15, 22.5, 30, and 35 wt %, in combination with 17 mM LAP were exposed to UV light over the same intensity range as the PEGDA 700 solutions. The results (FIG. 6A) indicate that the same qualitative trend observed for PEGDA 700 holds true for PEGDA 575, where increasing concentrations of acrylate functional groups yield progressively smaller unpolymerized shell thicknesses. However, chain length does empirically impact the absolute thickness of the unpolymerized shell, as similar acrylate concentrations of PEGDA 575 yield thicker unpolymerized shell thickness (a.k.a., smaller particles) than their PEGDA 700 counterparts. This behavior has been previously observed for thin films,[58,59] in which a film thickness was reported to be more closely correlated with PEGDA weight percent than acrylate concentration, but has not been fully explained.

Figure 6B:
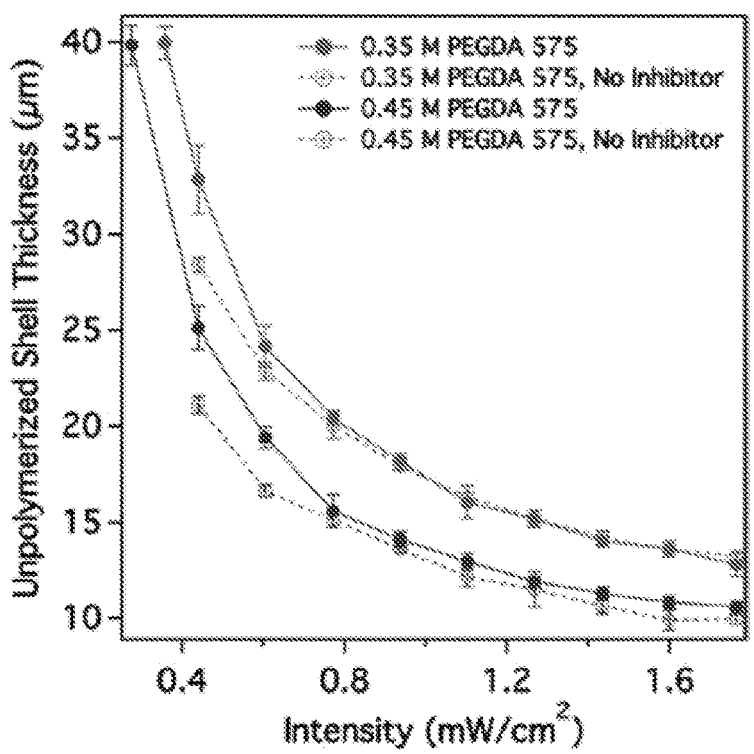

Effect of inhibitor present in PEGDA: Several parameters were investigated in order to explain the observed dependence upon PEGDA molecular weight. First, photopolymerization kinetics were characterized in the presence and absence of inhibitors—other than oxygen—in the oligomer solution. Inhibitors are commonly added to commercial monomers to prevent premature polymerization during storage and shipment, but they can either be removed prior to polymerization or used in combination of an excess of initiator to mitigate their effects.[60] As purchased, PEGDA 700 contains 100 ppm MEHQ/300 ppm BHT, while PEGDA 575 contains 400-600 ppm MEHQ. To evaluate the impact of inhibitor presence on the unpolymerized shell thickness, an inhibitor removal column was used to remove the MEHQ from PEGDA 575, and the inhibitor-free macromer solution was polymerized under the same exposure conditions as the macromer solution with inhibitor. The results, summarized in FIG. 6B, show that there is no significant difference in unpolymerized shell thickness following inhibitor removal, except at very low UV intensities. Because these inhibitors use dissolved oxygen to stabilize propagating radicals, their presence has little effect upon the photopolymerization reaction, during which oxygen is quickly consumed by initiator radicals prior to chain.[61,62]

Figure 6C:
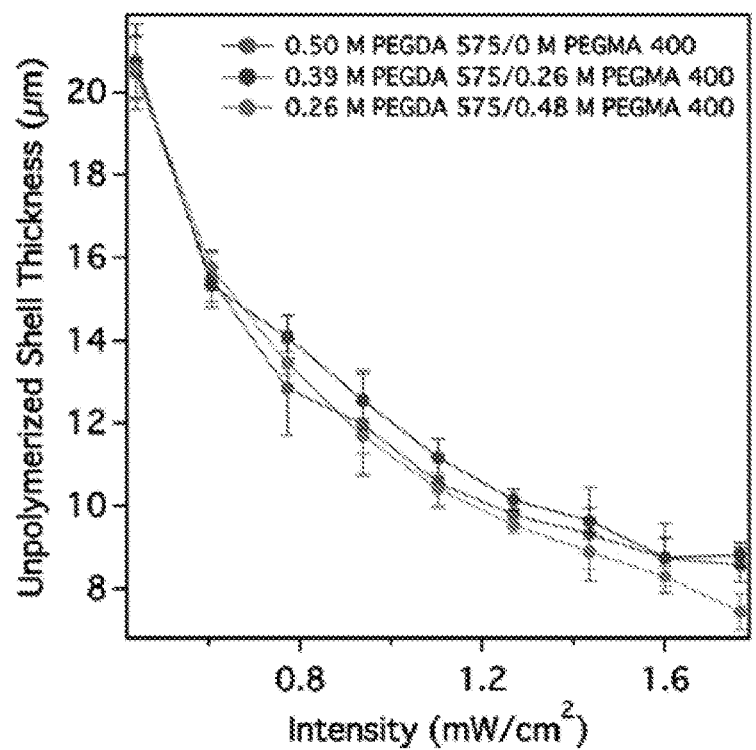

Effect of acrylate concentration: To further investigate the relative effects of PEGDA molecular weight and acrylate concentration, small amounts of poly(ethylene glycol) monoacrylate (PEGMA 400) were used in combination with PEGDA 575. The addition of PEGMA provided a means to establish constant acrylate concentration and solution viscosity, while changing the average macromer unit molecular weight. Further, the unreactive ends of PEGMA molecules modify hydrogel network properties, resulting in a decrease in the swelling ratio and an increase in the mechanical modulus and crosslinking density.[63] Maintaining a constant acrylate concentration of ~1 M, three different solutions containing different ratios of PEGDA/PEGMA were prepared and exposed to UV under constant initiator concentration. As shown in FIG. 6C, there is no significant difference in shell thickness at different PEGDA:PEGMA ratios, which indicates that, when keeping acrylate concentration and solution viscosity constant, the intrinsic distribution of PEG macromer molecular weight does not affect unpolymerized shell thickness by itself.

Oxygen solubility and diffusivity variation between PEGDA solutions: Changes to the concentration and molecular weight of PEGDA have been shown to alter the oxygen solubility and viscosity of hydrogel-forming solutions.[64,65] Oxygen solubility of the aqueous phase affects the system's initial and boundary conditions, as well as the oxygen flux into the droplet during photopolymerization. Previous work showed that oxygen solubility is inversely proportional to PEG concentration and molecular weight.[64] Moreover, viscosity has a significant impact on acrylate photopolymerization, due to its effect on the diffusivity of reactive species within the system. Lower viscosity solutions favor segmental mobility resulting in faster crosslinking rates, but this is countered by an increase of oxygen diffusion into the droplet.[65]

Figure 6D:
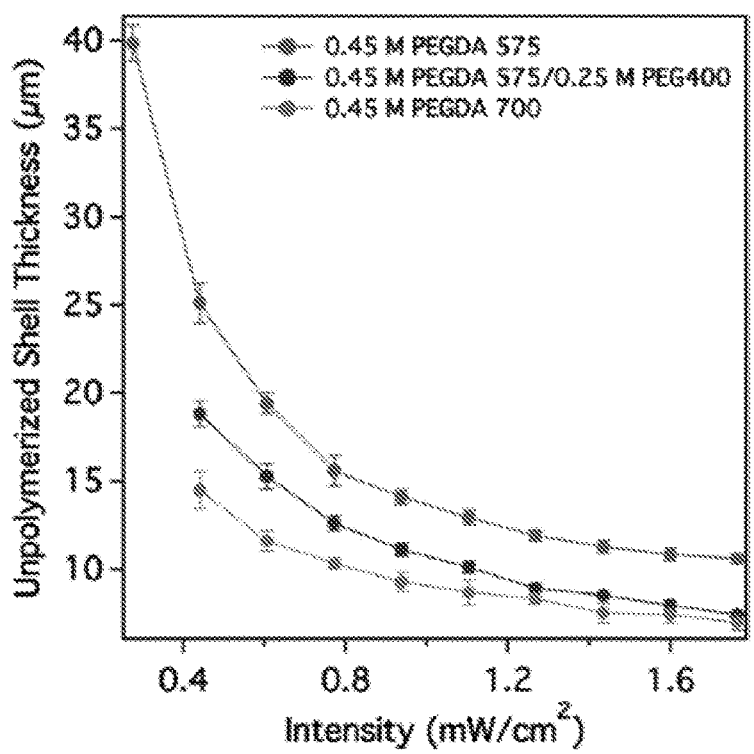
Figure 35:
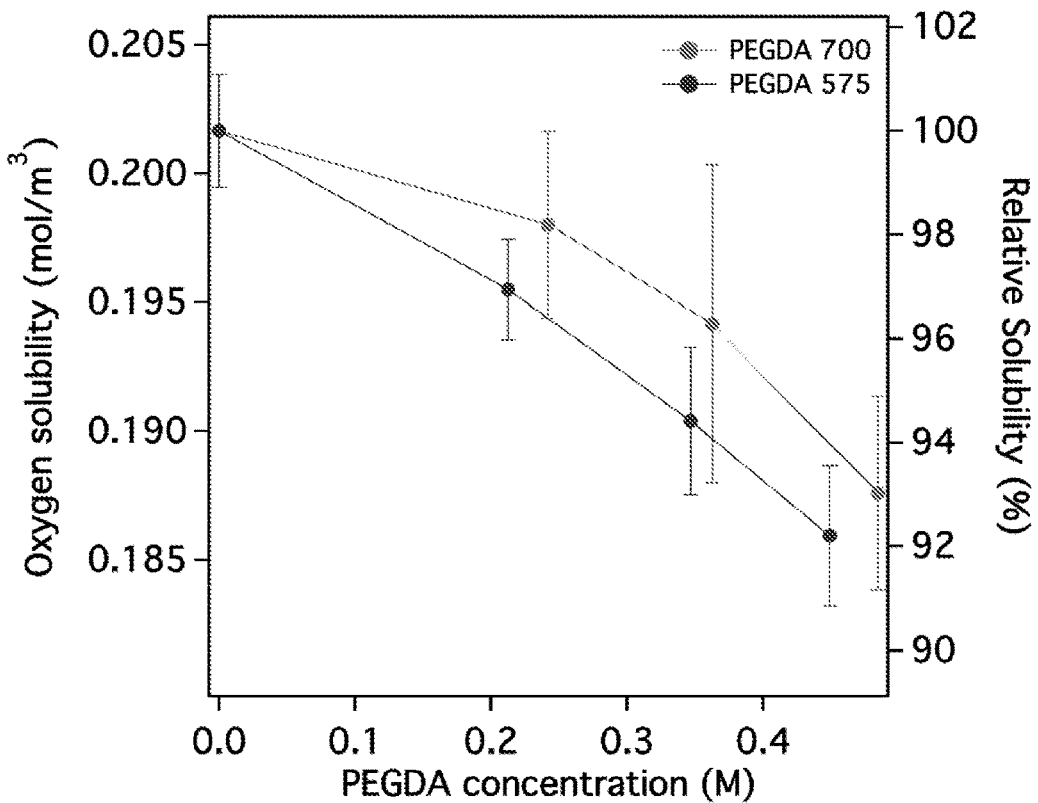
FIG. 35. Measured oxygen solubility (left axis) and relative oxygen solubility (right axis) in PEGDA solutions. Oxygen solubility is inversely proportional to PEGDA concentration; a significant difference in oxygen solubility between PEGDA 700 and PEGDA 575 solutions at equal acrylate concentrations was not observed.
Figure 36:
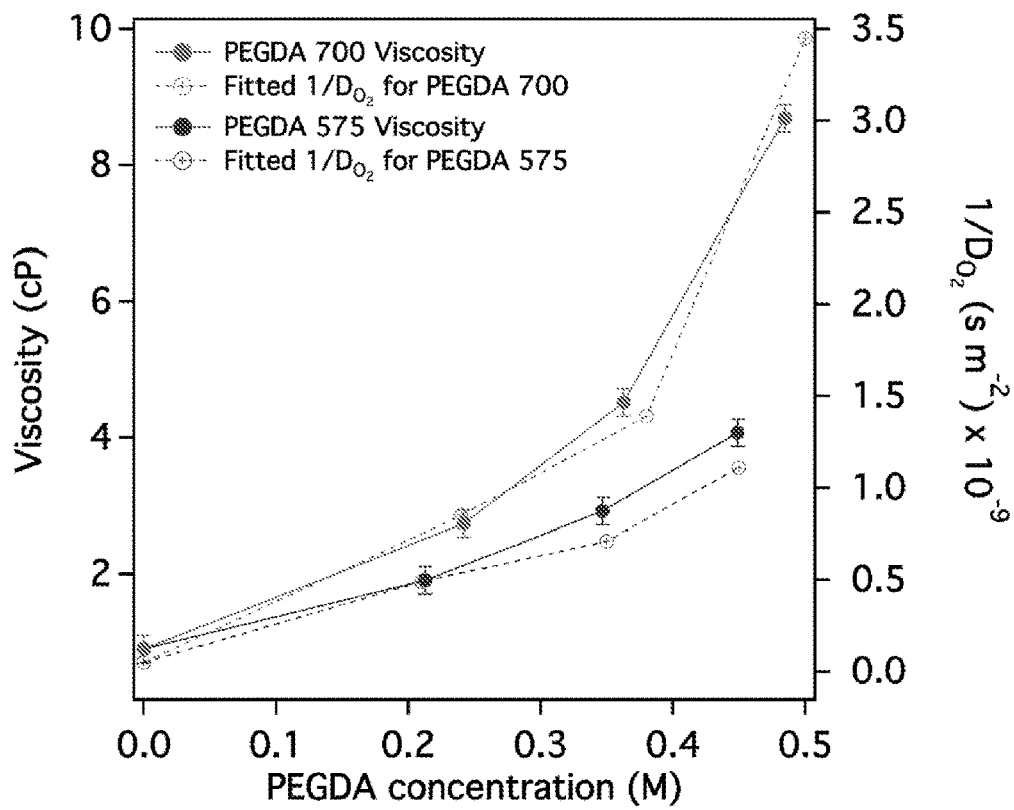
FIG. 36. Measured viscosity of PEGDA solutions (left axis) and inverse of the model fitted oxygen diffusivity coefficient (right axis) show a close correlation between these two variables. This justifies the use of fitted oxygen diffusivity in the reaction-diffusion model and establishes a need to incorporate viscosity data into this model to obtain accurate predictions.

Oxygen solubilities for solutions with varying concentrations of PEGDA 575 and 700 were measured and are reported in FIG. 35. An overall decrease in oxygen solubility is observed as PEGDA concentration increases, which partially explains the increase in shell thickness at lower concentrations, resulting from a higher rate of oxygen diffusion into the droplet as a result of an increased oxygen concentration difference between the particle edge and the emulsion interface. However, the difference in oxygen solubility between solutions of the two different PEGDA molecular weights is not significant, Moreover, modeling results, which are discussed later, showed little sensitivity to these small changes in oxygen solubility, warranting the measurement of solution viscosity to explain the difference between these two data sets. As shown in FIG. 36, there is a considerable viscosity difference between PEGDA 575 and 700 at similar acrylate concentrations. This is expected, as a higher weight percent of PEGDA 700 is required to match the acrylate concentration in PEGDA 575 solutions. We hypothesized that this variation in viscosity when varying PEGDA molecular weight and concentration has a larger effect on particle photopolymerization than acrylate concentration. To further investigate the hypothesis that solution viscosity dramatically affects oxygen diffusivity, unreactive poly(ethylene glycol) (PEG) was added to PEGDA solutions to increase solution viscosity without affecting acrylate stoichiometry. Unreactive poly(ethylene glycol) (PEG) has previously been used in combination with PEGDA to make porous hydrogels.[66,67] The addition of 0.25 M PEG 400 to a 0.45 M PEGDA 575 solution had a visible impact on photopolymerization (FIG. 6D), which is attributable to an increase in viscosity from 4.07±0.2 cP to 6.29±0.2 cP. The resulting decrease in the unpolymerized shell thickness reaffirms the inverse relationship between viscosity and photopolymerization kinetics, which strongly affects the thickness of the unpolymerized zone. The observed behavior merits the inclusion of solution viscosity and its effect on oxygen diffusivity as a modeling parameter to obtain accurate predictions of the hydrogel formation process. Previously developed models adequately capture stoichiometric effects but have failed to incorporate this alteration in oxygen transport in solutions when varying PEGDA molecular weights and concentrations, which can lead to large errors in the predicted behavior.

Figure 7:
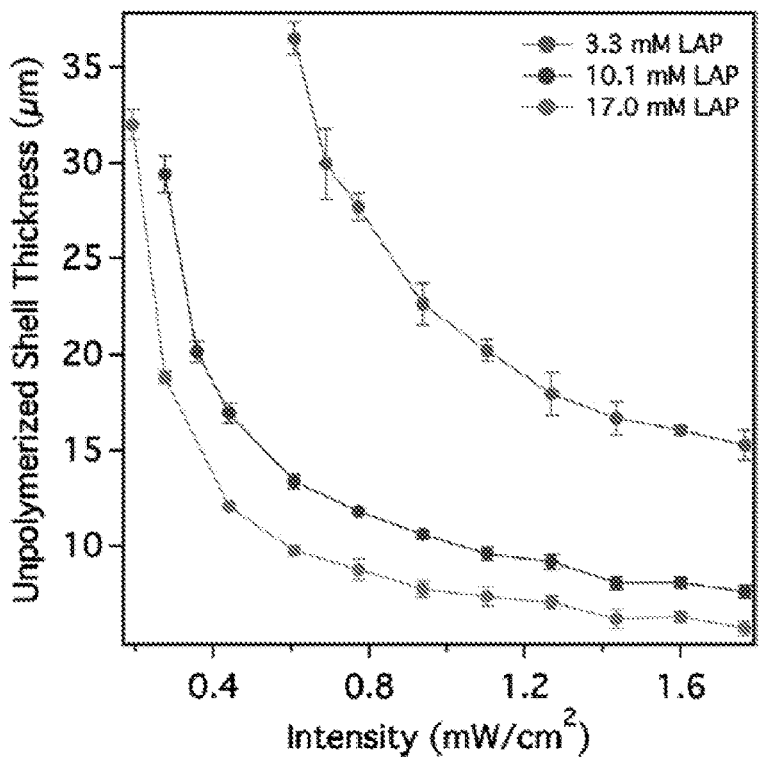
FIG. 7. Photoinitiator (LAP) concentration and intensity regulate reaction kinetics and oxygen consumption, providing broad control over shell thickness. ([PEGDA 700]=0.5 M).

Effect of photoinitiator concentration: We have shown that UV intensity, acrylate concentration, and viscosity-mediated oxygen solubility all affect the competing rates of photopolymerization and oxygen diffusion that determines the unpolymerized shell thickness. The selection of photoinitiator can also dramatically alter photopolymerization rates when all other parameters are fixed. Photoinitiators are generally selected based on their absorption and efficiency, as well as their solubility and application compatibility. We used a lithium acylphosphinate salt (lithium phenyl-2,4,6-trimethylbenzoylphosphinate (LAP)) with high water solubility and activity at UV wavelength ranges. Three discrete concentrations of LAP were used in combination with 0.5 M PEGDA 700. The results (FIG. 7) show that photoinitiator concentration is inversely proportional to unpolymerized shell thickness. Higher photoinitiator concentrations increase the concentration of radicals available to consume oxygen, which pushes the steady state oxygen boundary closer to the aqueous-oil interface, resulting in a smaller unpolymerized shell.

Figure 8:
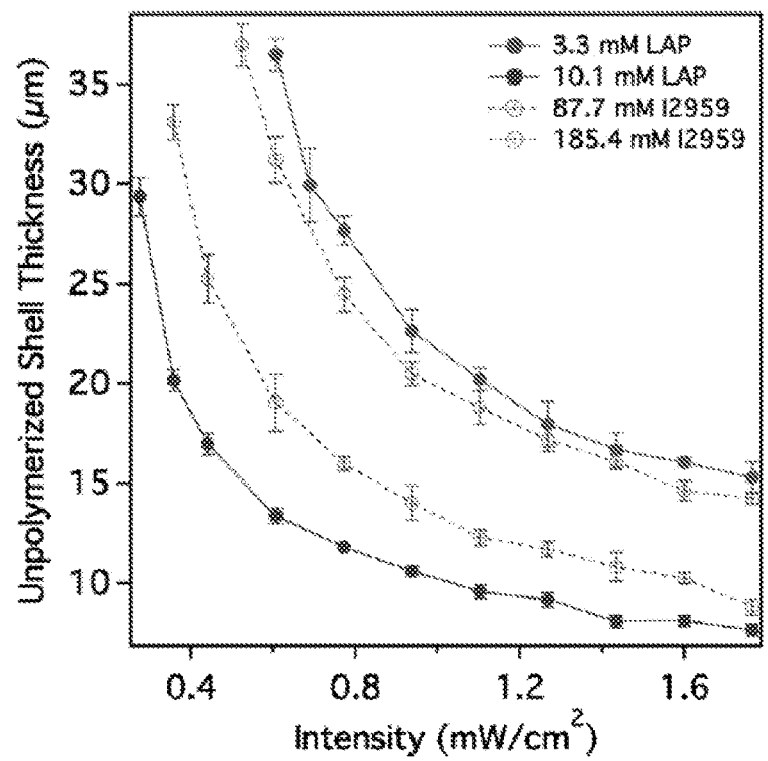
FIG. 8. A comparison of two common photoinitiators (LAP vs. Irgacure 2959) reveal stark kinetic differences, which correspond to large variations in shell thickness over significant differences in initiator concentration. While these differences are dramatic, they are not nearly as extreme as predicted by Equation 2 in conjunction with literature values for extinction coefficient and quantum yield. An empirical determination of an initiator-dependent rate constant instead allows the droplet-size independent shell thickness, and therefore produced particle size, to be predicted for a given hydrogel forming solution composition. ([PEGDA 700]=0.5 M).

Another photoinitiator, 2-hydroxy-1-[4-(2-hydroxyethoxy)phenyl]-2-methyl-1-propanone (I2959), was used to compare initiator efficiency and absorption. I2959 has also been used extensively in cell and biomolecule encapsulation applications due to its relatively high water solubility, moderate efficiency at lower wavelengths, and overall biocompatibility. FIG. 8 compares the results from the two photoinitiators, revealing stark kinetic differences, requiring significantly different initiator concentrations to obtain similar shell thicknesses.

An axisymmetric model to describe the effect of process parameters and physical properties: We have developed an axisymmetric one-dimensional, steady-state model for free radical hydrogel photopolymerization under different operating conditions. Specifically, we describe the spatial and temporal concentration of chemical species found within water-in-oil emulsion droplets in a microfluidic channel. With this model, we aim to quantify the effect of the operating parameters and variables on the unpolymerized shell thickness of a particle polymerized in situ. The equations and parameters used, including kinetic and transport constants, are included in Table 1.[45,47,68] This model evaluates the spatial distribution of photopolymerization rates as a function of chemical species concentration. When compared to the experimental results (FIG. 9), the predicted data shows close agreement, with the trends established previously being confirmed by the model.

TABLE 1

Transport and kinetic parameters used in the reaction-diffusion model for the oxygen inhibited photopolymerization of PEGDA particles within droplets in a microfluidic device

Figures 37A, 37B:
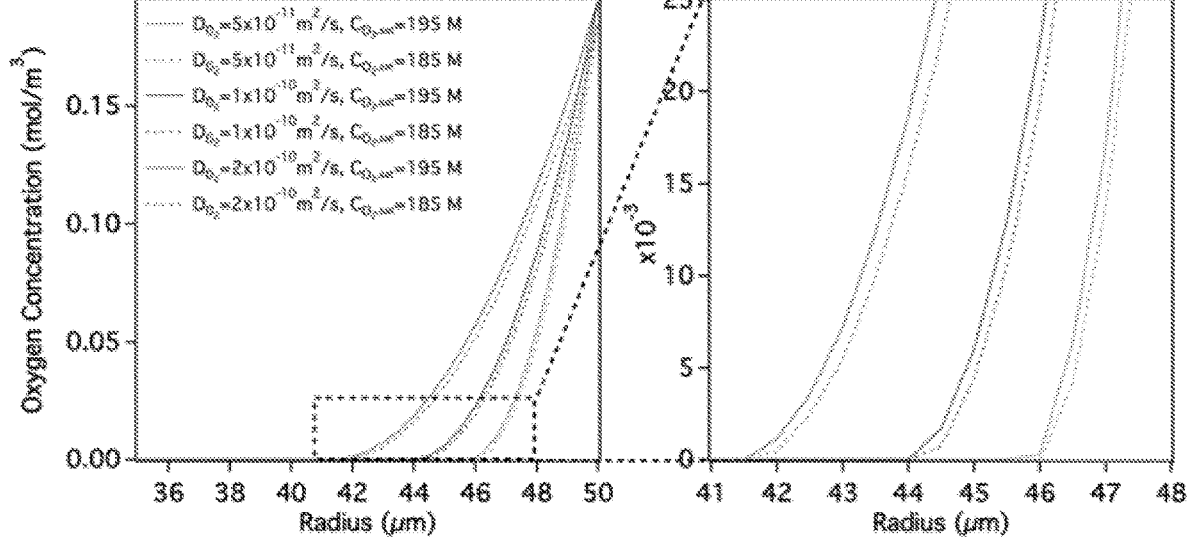
FIGS. 37A-37D. Sensitivity analysis for oxygen solubility and diffusivity in the developed reaction-diffusion model for a droplet with radius=50 µm. Oxygen concentration profile (FIGS. 37A-37B) and extent of monomer conversion (FIGS. 37C-37D) along droplet radius show little sensitivity to oxygen solubility, with very slight variation in the oxygen concentration profile and no change in predicted shell thickness.
Figures 37C, 37D:
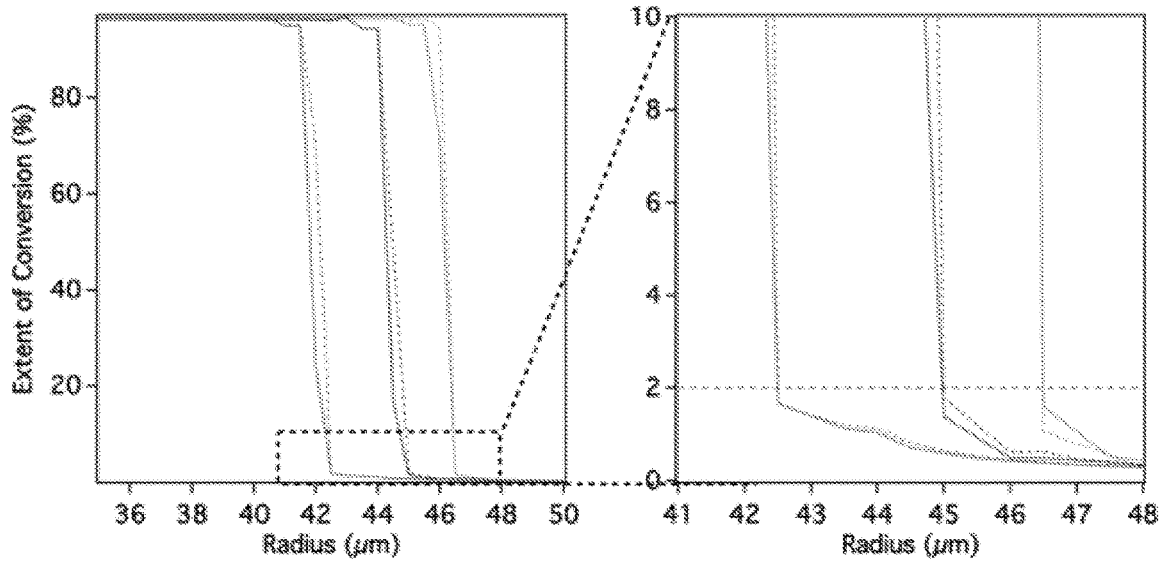

| Parameter | Description | Value | Unit | Source |
|---|---|---|---|---|
| $k_p$ | Rate constant of polymerization | $2.165 \times 10^4$ | L/(mol s) | 2 |
| $k_t$ | Rate constant of termination by coupling | $2.516 \times 10^6$ | L/(mol s) | 2 |
| $k_{O_2}$ | Rate constant of inhibition by oxygen | $3 \times 10^9$ for LAP<br>$4.2 \times 10^9$ for I2959<br>$5 \times 10^8$ for Acrylates | L/(mol s) | 3, 4<br>3, 4<br>5, 6 |
| $k_i$ | Rate constant of initiation | $1.9 \times 10^8$ for LAP<br>$4.8 \times 10^5$ for I2959 | L/(mol s) | 4, 7<br>8, 9 |
| $\varphi$ | Quantum yield | 0.29 for I2959<br>0.35 for LAP | | 10, 11<br>7 |
| $\varepsilon$ | Extinction coefficient | FIG. 37 | m²/mol | 1 |
| I | Intensity | Measured (FIG. 37) | mW/cm² | |
| $C_{O_2-H_2O}^{sat}$ | Saturation concentration of oxygen in water | Measured (FIG. 35) | mol/m³ | |
| $D_{M-H_2O}$ | Diffusivity of monomer in water* | $7.6 \times 10^{-12}$ | m²/s | Calculated (Eq. 7) |
| $D_{R\bullet-H_2O}$ | Diffusivity of initiator radical in water* | $1.1 \times 10^{-11}$ | m²/s | Calculated (Eq. 7) |
| $D_{M\bullet-H_2O}$ | Diffusivity of propagating radical in water | 0 | m²/s | 12 |
| $D_{PI-H_2O}$ | Diffusivity of initiator in water* | $1.6 \times 10^{-11}$ | m²/s | Calculated (Eq. 7) |

The modeling results for acrylate concentration (FIGS. 9A-9B) were fitted by changing oxygen diffusivity, which is justified by the aforementioned change in viscosity under varying PEGDA concentration. Generalized equations for diffusion of small molecules in liquids, such as the Wilke-Chang equation (Equation 8), show an inverse proportionality between diffusivity and solution viscosity. When comparing measured viscosity and the inverse of the fitted oxygen diffusivity for each PEGDA concentration (FIG. 36), there is a clear correlation between the two, validating the model's predictive capability. While changes in oxygen diffusivity greatly affected the predicted particle size, changes in oxygen solubility in the measured range (185-200 M) were shown to have a negligible impact on the predicted oxygen concentration profile, and did not affect the predicted unpolymerized shell thickness at all (FIG. 37). Conversely, varying diffusivity values for all other mobile chemical species, including photoinitiator, monomer, and initiator radical, indicated no effect on the predicted shell thickness. When viscous effects on oxygen diffusivity are ignored, the model shows that there is little effect on changing acrylate concentration on the unpolymerized shell thickness. This matches previous reports[39] that have shown that the local decrease in oxygen concentration, which allows the polymerization reaction to take place, is independent of acrylate concentration.

Figure 9A:
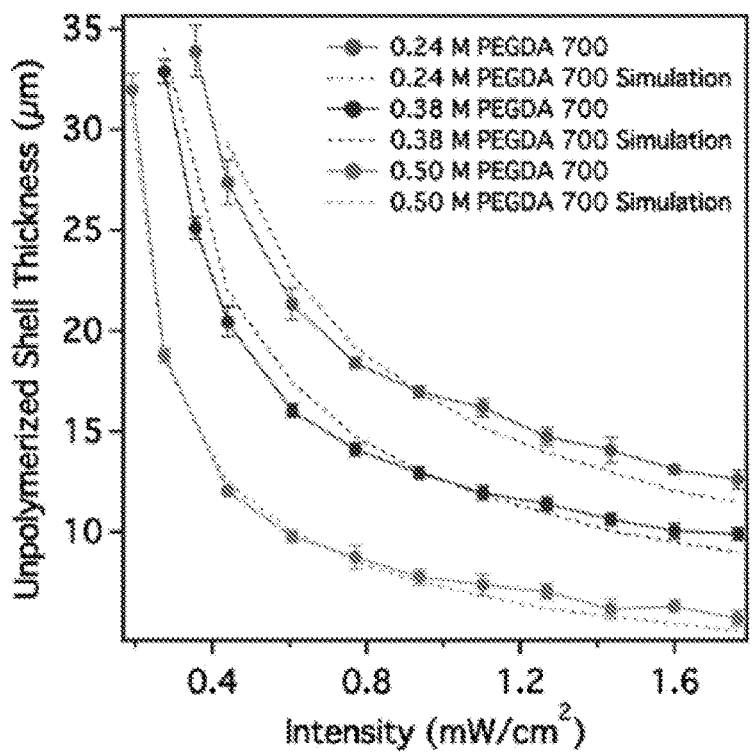
FIGS. 9A-9D. Predicted unpolymerized shell thicknesses under different operating conditions closely resemble empirical data.
Figure 9B:
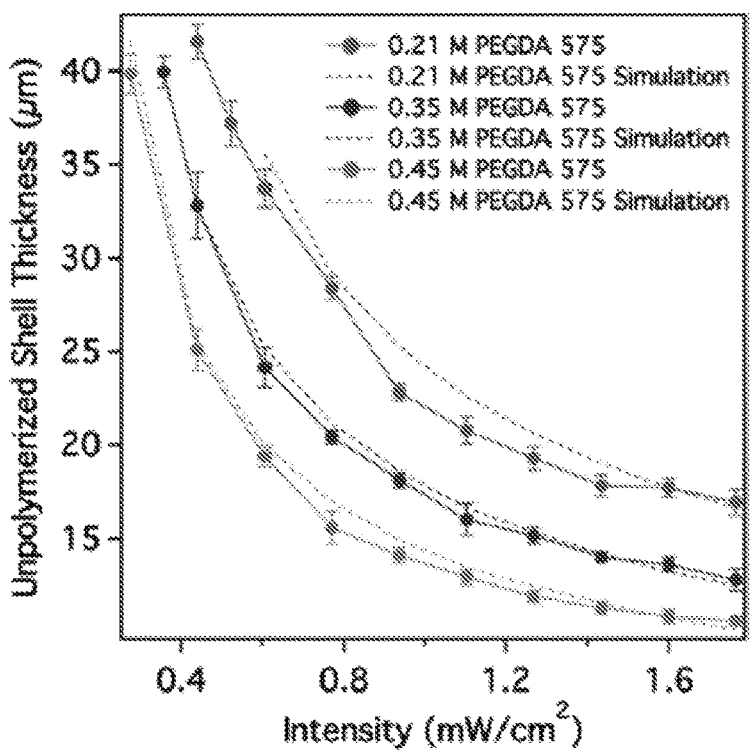
Figure 9C:
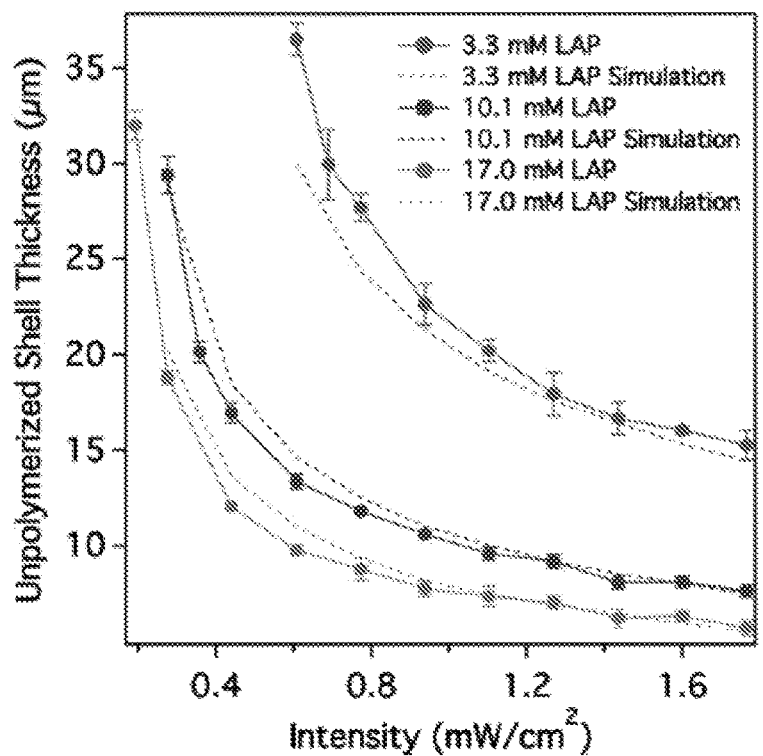
Figure 9D:
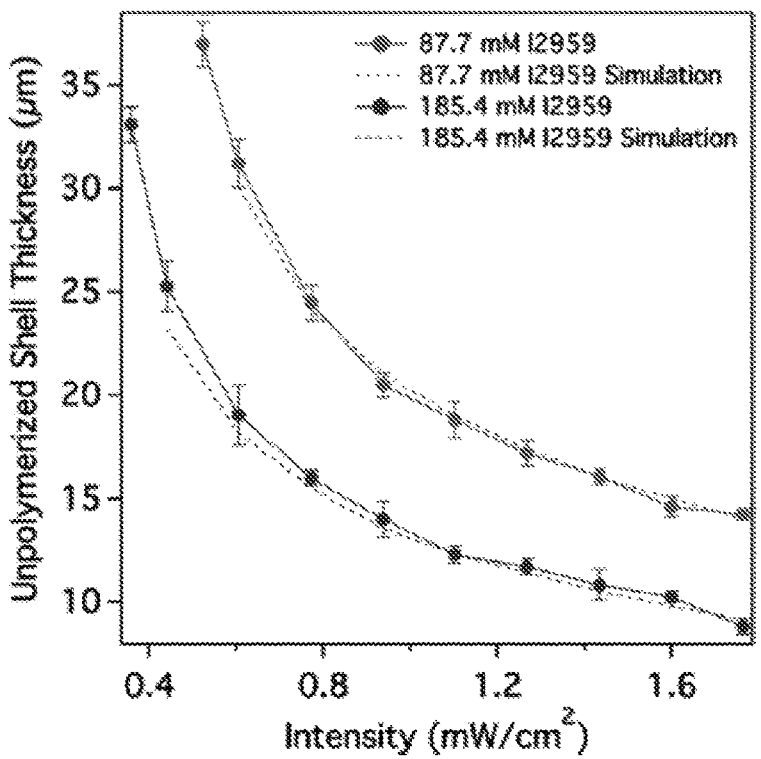

FIG. 9C shows close agreement between collected data and model predictions when using LAP, without requiring a change in transport parameters, as the addition of small photoinitiator molecules does not impact solution viscosity.

Figure 38:
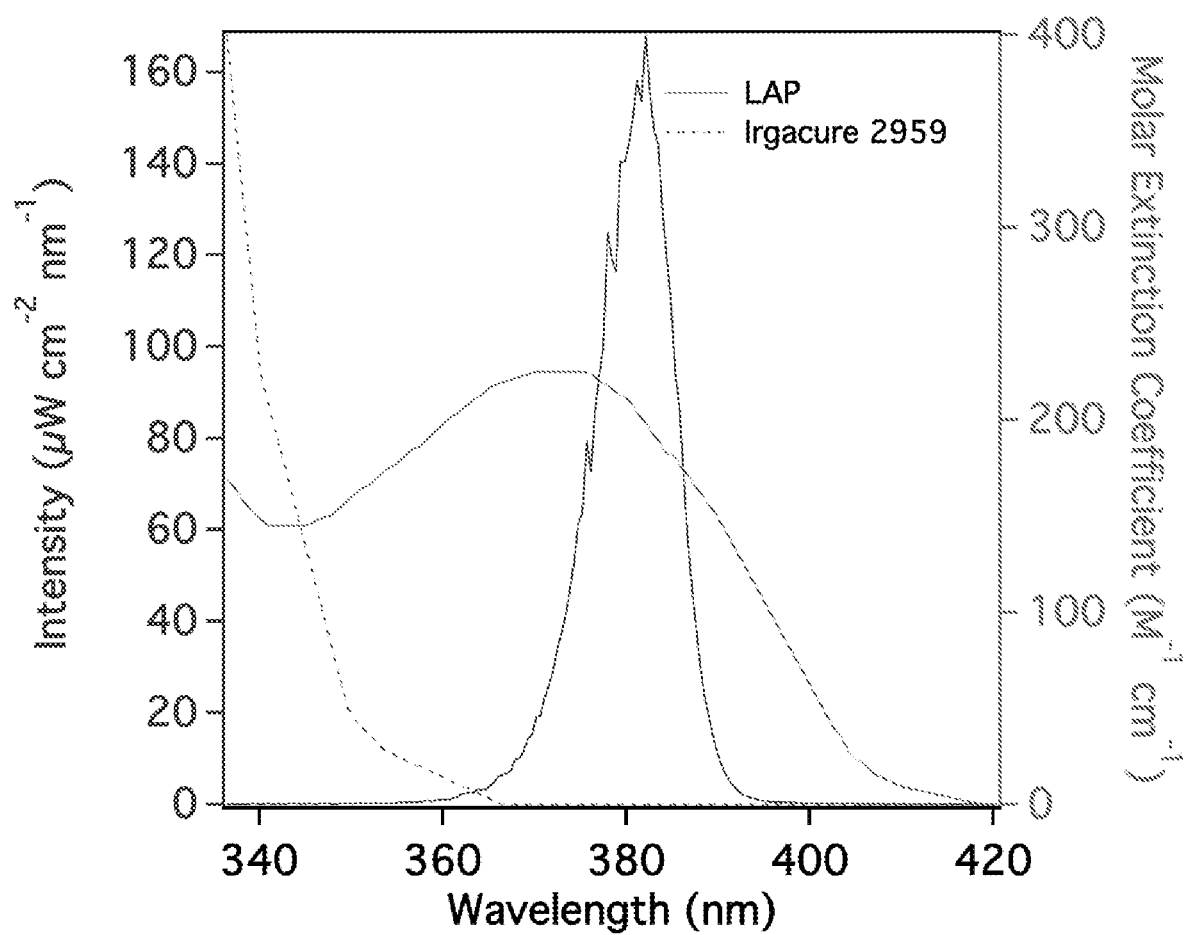
FIG. 38. Measured fluorescent light source spectral output at 100% intensity (blue) and theoretical molar extinction coefficient for LAP and Irgacure 2959 (green).[1] The area under the overlap of these two curves is used to predict $k_d$ values for each initiator (Equation S2). LAP has significantly higher activity in the wavelength range used, but empirical results coupled with a fitted model have determined the difference in the activity of these two initiators is not as substantial as the theoretical data predicts.

Initially, the model predicted that no photopolymerization would occur when using Irgacure2959 even at high concentrations, due to its low molar extinction coefficient and poor overlap with the operating spectral range (FIG. 38). Fitting $k_d$ values resulted in a 30-fold difference between the predicted and fitted value (FIG. 9D), indicating a discrepancy between theoretical and experimental kinetic behavior of this photoinitiator.

Oxygen-inhibited photopolymerization of PEGDA droplets in a microfluidic device was conducted under different operating conditions to obtain particles over a wide range of sizes from parent droplets with a single diameter. It has been shown that ratio of unpolymerized and polymerized droplet radius is governed by the relative rates of oxygen consumption and diffusive replenishment. In turn, the steady state oxygen profile is influenced by a host of stoichiometric and physical properties inherent to the emulsion. Ultraviolet intensity, macromer concentration and molecular weight, and initiator concentration and type were experimentally varied to quantify their individual effects on the unpolymerized shell surrounding the polymerized hydrogel particle. Preliminary experiments revealed that, beyond a critical induction time, hydrogel particle size remains unchanged despite a visible increase in crosslinking, presenting the intriguing possibility that hydrogel particles with defined mechanical properties may be produced by simply manipulating exposure time,[55] facilitating the production of tailored hydrogel particles for drug delivery[9,24] and tissue engineering.[7]

As hypothesized, UV intensity and particle size are directly proportional, exhibiting increased sensitivity to intensity as particle size decreased. Initiator stoichiometry also behaved in a predictable manner, and revealed substantially different initiator activity between LAP and Irgacure 2959. Varying PEGDA concentration and molecular weight revealed that acrylate stoichiometry has little effect on particle size; rather, physical changes in solution viscosity surpassed kinetic effects. The number of independent variables and their often counteracting effects on polymerization and diffusion demand the development of a robust predictive model. We have presented a refined finite element reaction-diffusion model that provides good agreement with experimental results, indicating that we are able to precisely control and quantitatively predict unpolymerized shell thickness to obtain specific particle sizes in droplets of arbitrary diameter. By using this technique, we have demonstrated that it is possible to continually produce monodisperse hydrogel particles in the micro- and nano- scale from larger, easily produced droplets, overcoming the drawbacks of alternative microfluidic techniques that have limited ranges of application.[29,30,32]

Supplemental Information

Model
Reactions

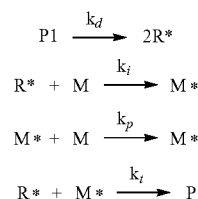

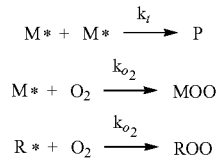

Where: PI: Photoinitiator, R*: Primary radical, M: Acrylate functional group, M*: Propagating radical, $O_2$: Oxygen, P: Terminated polymer chain, ROO: Primary radical peroxide, MOO: Propagating radical peroxide Kinetics $$\frac{d[PI]}{dr} = -k_d[PI] \quad [\text{Eq. 1}]$$

$$k_d = \left(\frac{\varphi}{N_A hc}\right) \int \varepsilon(\lambda) I(\lambda) d\lambda \quad [\text{Eq. 2}]$$

$$\frac{d[R*]}{dt} = 2k_d[PI] - k_i[R*][M] - k_t[R*][M*] - k_{O_2}[R*][O_2] \quad [\text{Eq. 3}]$$

$$\frac{d[M]}{dt} = -k_i[M][R*] - k_p[M][M*] \quad [\text{Eq. 4}]$$

$$\frac{d[M*]}{dt} = k_i[R*][M] - k_t[M*][R*] - k_t[M*]^2 - k_{O_2}[M*][O_2] \quad [\text{Eq. 5}]$$

$$\frac{d[O_2]}{dt} = -k_{O_2}[O_2][M*] - k_{O_2}[O_2][R*] \quad [\text{Eq. 6}]$$

$$p = \frac{[M]}{[M]_o} - 1 \quad [\text{Eq. 7}]$$

Where: p: Extent of conversion

Mass transport

Wilke-Chang Equation $$D_i = \frac{7.4 \times 10^{-8} T \sqrt{\alpha_{SV} M_{SV}}}{\eta_{SV} V_{b,a}^{0.6}} \quad [\text{Eq. 8}]$$

Where: $D_i$: Diffusivity of small molecule in liquid phase system, T: Absolute temperature (K), $\alpha_{sv}$: Solvent association coefficient, $M_{sv}$: Solvent molecular weight, $V_b$: Molar volume at the normal boiling point of solute $$\frac{\partial c_i}{\partial t} + \nabla \cdot (-D_i \nabla c_i) = R_i \quad [\text{Eq. 9}]$$

TABLE 2

Fitted oxygen diffusivity values for PEGDA solutions. (Even though diffusivity of mobile species was determined to vary depending on viscosity, a sensitivity analysis on the model showed little or no effect of these diffusivity values on the model).

| PEGDA Molecular Weight | Concentration (M) | Oxygen Diffusivity ($m^2/s$) |
|---|---|---|
| 700 | 0.24 | $1.175 \times 10^{-10}$ |
|  | 0.38 | $7.172 \times 10^{-11}$ |
|  | 0.5 | $2.900 \times 10^{-11}$ |

TABLE 2-continued

Fitted oxygen diffusivity values for PEGDA solutions. (Even though diffusivity of mobile species was determined to vary depending on viscosity, a sensitivity analysis on the model showed little or no effect of these diffusivity values on the model).

| PEGDA Molecular Weight | Concentration (M) | Oxygen Diffusivity ($m^2/s$) |
|---|---|---|
| 575 | 0.21 | $2.027 \times 10^{-10}$ |
|  | 0.35 | $1.399 \times 10^{-10}$ |
|  | 0.45 | $9.020 \times 10^{-11}$ |

TABLE 3

Materials and Methods: Chemical species information.

| Chemical Name | Abbreviation | Vendor | Catalog No. |
|---|---|---|---|
| Poly(ethylene glycol) diacrylate 575 | PEGDA 575 | Sigma-Aldrich | 26570-48-9 |
| Poly(ethylene glycol) diacrylate 700 | PEGDA 700 | Sigma-Aldrich | 26570-48-9 |
| Poly(ethylene glycol) monoacrylate 400 | PEGMA 400 | Polysciences, Inc. | 25736-86-1 |
| Poly(ethylene glycol) 400 | PEG 400 | Sigma-Aldrich | 25322-68-3 |
| 2-hydroxy-4'-(2-hydroxyethoxy)-2-methylpropiophenone | Irgacure 2959 | Sigma-Aldrich | 106797-53-9 |
| Lithium phenyl-2,4,6-trimethyl-benzoylphosphinate | LAP | Synthesized from protocol | 85073-19-4 |
| 3-ethoxy-1,1,1,2,3,4,4,5,5,6,6,6-dodecafluoro-2-trifluoromethyl-hexane | Novec 7500 | Dolomite Microfluidics | 297730-93-9 |
| Picosurf (Poly-fluorinated surfactant) | — | Dolomite Microfluidics | — |

REFERENCES (1) Griffith, L. G. Polymeric Biomaterials. Acta mater 2000, No. 48, 263-277.
(2) Saenz, A.; Rivera-Muñoz, E.; Brostow, W.; Castaño, V. M. Ceramic Biomaterials: an Introductory Overview; 1999; Vol. 21, pp 297-306.
(3) Niinomi, M. Metallic Biomaterials. *J Artif Organs* 2008, 11 (3), 105-110.
(4) Peppas, N. A.; Hilt, J. Z.; Khademhosseini, A.; Langer, R. Hydrogels in Biology and Medicine: From Molecular Principles to Bionanotechnology. *Adv. Mater.* 2006, 18 (11), 1345-1360.
(5) Ahmed, E. M. Hydrogel: Preparation, Characterization, and Applications: a Review. *Journal of Advanced Research* 2015, 6 (2), 105-121.
(6) Anseth, K. S.; Metters, A. T.; Bryant, S. J.; Martens, P. J.; Elisseeff, J. H.; Bowman, C. N. In Situ Forming Degradable Networks and Their Application in Tissue Engineering and Drug Delivery. *Journal of Controlled Release* 2002, 78, 199-209.
(7) Hoffman, A. S. Hydrogels for Biomedical Applications. *Advanced Drug Delivery Reviews* 2012, 64, 18-23.
(8) Datta, A. Characterization of Polyethylene Glycol Hydrogels for Biomedical Applications. 2007, 1-116.
(9) Hamidi, M.; Azadi, A.; Rafiei, P. Hydrogel Nanoparticles in Drug Delivery. *Advanced Drug Delivery Reviews* 2008, 60 (15), 1638-1649.
(10) Lin, C.-C.; Anseth, K. S. PEG Hydrogels for the Controlled Release of Biomolecules in Regenerative Medicine. *Pharm Res* 2008, 26 (3), 631-643.
(11) Oh, J. K.; Drumright, R.; Siegwart, D. J.; Matyjaszewski, K. The Development of Microgels/Nanogels for Drug Delivery Applications. *Progress in Polymer Science* 2008, 33 (4), 448-477.
(12) Zhu, J. Bioactive Modification of Poly(Ethylene Glycol) Hydrogels for Tissue Engineering. Biomaterials 2010, 31 (17), 4639-4656.
(13) Turturro, M. V.; Rendón, D. M. V.; Tcymour, F.; Papavasiliou, G. Kinetic Investigation of Poly(Ethylene Glycol) Hydrogel Formation via Perfusion-Based Frontal Photopolymerization: Influence of Free-Radical Polymerization Conditions on Frontal Velocity and Swelling Gradients. Macromolecular Reaction Engineering 2013, 7 (2), 107-115.
(14) Hagel, V.; Haraszti, T.; Boehm, H. Diffusion and Interaction in PEG-DA Hydrogels. *Biointerphases* 2013, 8 (36), 1-9.
(15) Ramanan, R. M. K.; Chellamuthu, P.; Tang, L.; Nguyen, K. T. Development of a Temperature-Sensitive Composite Hydrogel for Drug Delivery Applications. *Biotechnol Progress* 2006, 22 (1), 118-125.
(16) Du, Y. J.; Lemstra, P. J.; Nijenhuis, A. J.; van Aert, H. A. M.; Bastiaansen, C. ABA Type Copolymers of Lactide with Poly(Ethylene Glycol). Kinetic, Mechanistic, and Model Studies. *Macromolecules* 1995, 28, 2124-2132.
(17) Harrane, A.; Leroy, A.; Nouailhas, H.; Garric, X.; Coudane, J.; Nottelet, B. PLA-Based Biodegradable and Tunable Soft Elastomers for Biomedical Applications. Biomed. Mater. 2011, 6 (6), 065006-065012.
(18) Kharkar, P. M.; Kiick, K. L.; Kloxin, A. M. Design of Thiol- and Light-Sensitive Degradable Hydrogels Using Michael-Type Addition Reactions. *Polym. Chem.* 2015, 6 (31), 5565-5574.
(19) Kloxin, A. M.; Tibbitt, M. W.; Anseth, K. S. Synthesis of Photodegradable Hydrogels as Dynamically Tunable Cell Culture Platforms. *Nature Protocols* 2010, 5 (12), 1867-1887.
(20) West, J. L.; Hubbell, J. A. Polymeric Biomaterials with Degradation Sites for Proteases Involved in Cell Migration. *Macromolecules* 1999, 32 (1), 241-244.
(21) Yang, C.; DelRio, F. W.; Ma, H.; Killaars, A. R.; Basta, L. P.; Kyburz, K. A.; Anseth, K. S. Spatially Patterned Matrix Elasticity Directs Stem Cell Fate. *Proc Natl Acad Sci USA* 2016, 113 (31), E4439-E4445.
(22) Fairbanks, B. D.; Schwartz, M. P.; Bowman, C. N.; Anseth, K. S. Photoinitiated Polymerization of PEG-Diacrylate with Lithium Phenyl-2,4,6-Trimethylbenzoylphosphinate: Polymerization Rate and Cytocompatibility. Biomaterials 2009, 30 (35), 6702-6707.
(23) Helgeson, M. E.; Chapin, S. C.; Doyle, P. S. Hydrogel Microparticles From Lithographic Processes: Novel Materials for Fundamental and Applied Colloid Science. *Current Opinion in Colloid & Interface Science* 2011, 16 (2), 106-117.
(24) Buwalda, S. J.; Vermonden, T.; Hennink, W. E. Hydrogels for Therapeutic Delivery: Current Developments and Future Directions. *Biomacromolecules* 2017, 18 (2), 316-330.
(25) Saunders, B.; Vincent, B. Microgel Particles as Model Colloids: Theory, Properties and Applications. *Advances in Colloid and Interface Science* 1999, No. 80, 1-25.
(26) Zhu, P.; Wang, L. Passive and Active Droplet Generation with Microfluidics: a Review. *Lab Chip* 2017, 17 (1), 34-75.
(27) Teh, S.-Y.; Lin, R.; Hung, L.-H.; Lee, A. P. Droplet Microfluidics. *Lab Chip* 2008, 8 (2), 198-23.

(28) De Geest, B. G.; Urbanski, J. P.; Thorsen, T.; Demeester, J.; Dc Smedt, S. C. Synthesis of Monodisperse Biodegradable Microgels in Microfluidic Devices. *Langmuir* 2005, 21 (23), 10275-10279.

(29) Anna, S. L.; Mayer, H. C. Microscale Tipstreaming in a Microfluidic Flow Focusing Device. *Phys. Fluids* 2006, 18 (12), 121512-121514.

(30) Jeong, W.-C.; Lim, J.-M.; Choi, J.-H.; Kim, J.-H.; Lee, Y.-J.; Kim, S.-H.; Lee, G.; Kim, J.-D.; Yi, G.-R.; Yang, S.-M. Controlled Generation of Submicron Emulsion Droplets via Highly Stable Tip-Streaming Mode in Microfluidic Devices. *Lab Chip* 2012, 12 (8), 1446-1449.

(31) Kim, H.; Luo, D.; Link, D.; Weitz, D. A.; Marquez, M.; Cheng, Z. Controlled Production of Emulsion Drops Using an Electric Field in a Flow-Focusing Microfluidic Device. *Appl. Phys. Lett.* 2007, 91 (13), 133106-3.

(32) Tan, Y.-C.; Lee, A. P. Microfluidic Separation of Satellite Droplets as the Basis of a Monodispersed Micron and Submicron Emulsification System. *Lab Chip* 2005, 5 (10), 1178-6.

(33) He, M.; Sun, C.; Chiu, D. T. Concentrating Solutes and Nanoparticles Within Individual Aqueous Microdroplets. *Anal. Chem.* 2004, 76 (5), 1222-1227.

(34) Sang, Y. Y. C.; Lorenceau, E.; Wahl, S.; Stoffel, M.; Angelescu, D. E.; Höhler, R. A Microfluidic Technique for Generating Monodisperse Submicron-Sized Drops. *RSC Advances* 2013, 3 (7), 2330-2336.

(35) Gou, L.; Opheim, B.; Coretsopoulos, C. N.; Scranton, A. B. Consumption of the Molecular Oxygen in Polymerization Systems Using Photosensitized Oxidation of Dimethylanthracene. *Chemical Engineering Communications* 2006, 193 (5), 620-627.

(36) Hofer, M.; Moszner, N.; Liska, R. Oxygen Scavengers and Sensitizers for Reduced Oxygen Inhibition in Radical Photopolymerization. *J. Polym. Sci. A Polym. Chem.* 2008, 46 (20), 6916-6927.

(37) Chong, J. Oxygen Consumption During Induction Period. *Journal of Applied Polymer Science* 1969, 13, 241-247.

(38) Ligon, S. C.; Husár, B.; Wutzel, H.; Holman, R.; Liska, R. Strategies to Reduce Oxygen Inhibition in Photoinduced Polymerization. *Chem. Rev.* 2014, 114 (1), 557-589.

(39) Decker, C.; Jenkins, A. D. Kinetic Approach of O2 Inhibition in Ultraviolet- and Laser-Induced Polymerizations. *Macromolecules* 1985, 1241-1244.

(40) O'Brien, A. K.; Bowman, C. N. Impact of Oxygen on Photopolymerization Kinetics and Polymer Structure. *Macromolecules* 2006, 39 (7), 2501-2506.

(41) Merkel, T. C.; Bondar, V. I.; Nagai, K.; Freeman, B. D.; Pinnau, I. Gas Sorption, Diffusion, and Permeation in Poly(Dimethylsiloxane). *Journal of Polymer Science Part B Polymer Physics* 2000, 38, 415-434.

(42) McDonald, J. C.; Whitesides, G. M. Poly(Dimethylsiloxane) as a Material for Fabricating Microfluidic Devices. *Acc. Chem. Res.* 2002, 35 (7), 491-499.

(43) Miller, C. W.; Hoyle, C. E.; Jönsson, S.; Nason, C.; Lee, T. Y.; Kuang, W. F.; Viswanathan, K. N-Vinylamides and Reduction of Oxygen Inhibition in Photopolymerization of Simple Acrylate Formulations. In *Photoinitiated Polymerization*; ACS Symposium Series; American Chemical Society: Washington, D C, 2009; Vol. 847, pp 2-14.

(44) Kloosterboer, J. G.; Lijten, G. F. C. M.; Boots, H. M. J. Network Formation by Chain Crosslinking Photopolymerization and Its Applications in Electronics. *Makromol. Chem.* 1989, 24, 223-230.

(45) Dendukuri, D.; Panda, P.; Haghgooie, R.; Kim, J. M.; Hatton, T. A.; Doyle, P. S. Modeling of Oxygen-Inhibited Free Radical Photopolymerization in a PDMS Microfluidic Device. *Macromolecules* 2008, 41 (22), 8547-8556.

(46) Shim, T. S.; Yang, S.-M.; Kim, S.-H. Dynamic Designing of Microstructures by Chemical Gradient-Mediated Growth. *Nat Comms* 2015, 6, 6584-6587.

(47) Krutkramelis, K.; Xia, B.; Oakey, J. Monodisperse Polyethylene Glycol Diacrylate Hydrogel Microsphere Formation by Oxygen-Controlled Photopolymerization in a Microfluidic Device. *Lab Chip* 2016, 16 (8), 1457-1465.

(48) Kizilel, S.; Pérez-Luna, V. H.; Teymour, F. Mathematical Model for Surface-Initiated Photopolymerization of Poly(Ethylene Glycol) Diacrylate. *Macromol. Theory Simul.* 2006, 15 (9), 686-700.

(49) Goodner, M. D.; Bowman, C. N. Development of a Comprehensive Free Radical Photopolymerization Model Incorporating Heat and Mass Transfer Effects in Thick Films. *Chemical Engineering Science* 2002, 57 (5), 887-900.

(50) O'Brien, A. K.; Bowman, C. N. Modeling the Effect of Oxygen on Photopolymerization Kinetics. *Macromol. Theory Simul.* 2006, 15 (2), 176-182.

(51) Majima, T.; Schnabel, W.; Weber, W. Phenyl-2,4,6-Trimethylbenzoylphosphinates as Water-Soluble Photoinitiators. Generation and Reactivity of O=P(C6H5)(O—) Radical Anions. *Makromol. Chem.* 1991, 2307-2315.

(52) Holtze, C.; Rowat, A. C.; Agresti, J. J.; Hutchison, J. B.; Angilè, F. E.; Schmitz, C. H. J.; Köster, S.; Duan, H.; Humphry, K. J.; Scanga, R. A.; Johnson, J. S.; Pisignano, D.; Weitz, D. A. Biocompatible Surfactants for Water-in-Fluorocarbon Emulsions. *Lab Chip* 2008, 8 (10), 1632-1639.

(53) Anderson, J. R.; Chiu, D. T.; Jackman, R. J.; Cherniavskaya, O.; McDonald, J. C.; Wu, H.; Whitesides, S. H.; Whitesides, G. M. Fabrication of Topologically Complex Three-Dimensional Microfluidic Systems in PDMS by Rapid Prototyping. *Anal. Chem.* 2000, 72 (14), 3158-3164.

(54) Andrzejewska, E. Photopolymerization Kinetics of Multifunctional Monomers. *Progress in Polymer Science* 2001, 26 (4), 605-665.

(55) Hwang, D. K.; Oakey, J.; Toner, M.; Arthur, J. A.; Anseth, K. S.; Lee, S.; Zeiger, A.; Van Vliet, K. J.; Doyle, P. S. Stop-Flow Lithography for the Production of Shape-Evolving Degradable Microgel Particles. *J. Am. Chem. Soc.* 2009, 131 (12), 4499-4504.

(56) Dendukuri, D.; Panda, P.; Haghgooie, R.; Kim, J. M.; Hatton, T. A.; Doyle, P. S. Modeling of Oxygen-Inhibited Free Radical Photopolymerization in a PDMS Microfluidic Device. *Macromolecules* 2008, 41 (22), 8547-8556.

(57) Peppas, N.; Sahlin, J. A Simple Equation for the Description of Solute Release. III. Coupling of Diffusion and Relaxation. *International Journal of Pharmaceutics* 1989, No. 57, 169-172.

(58) Cruise, G.; Scharp, D.; Hubbell, J. Characterization of Permeability and Network Structure of Interfacially Photopolymerized Poly(Ethylene Glycol) Diacrylate Hydrogels. *Biomaterials* 1998, No. 19, 1287-1294.

(59) Kizilel, S.; Perez-Luna, V. H.; Teymour, F. Mathematical Model for Surface-Initiated Photopolymerization of Poly(Ethylene Glycol) Diacrylate. *Macromol. Theory Simul.* 2006, 15 (9), 686-700.

(60) Odian, G. *Principles of Polymerization*; John Wiley & Sons, Inc.: Hoboken, N.J., 2004; pp 1-839.

(61) Burton, G. W.; Ingold, K. U. Autoxidation of Biological Molecules. *J. Am. Chem. Soc.* 1981, No. 103, 6472-6477.
(62) Becker, H.; Vogel, H. The Role of Hydroquinone Monomethyl Ether in the Stabilization of Acrylic Acid. *Chem. Eng. Technol.* 2006, 29 (10), 1227-1231.
(63) Beamish, J. A.; Zhu, J.; Kottke-Marchant, K.; Marchant, R. E. The Effects of Monoacrylated Poly(Ethylene Glycol) on the Properties of Poly(Ethylene Glycol) Diacrylate Hydrogels Used for Tissue Engineering. *J. Biomed. Mater. Res.* 2009, 9999A, NA-NA.
(64) Mexal, J.; Fisher, J.; Osteryoung, J.; Reid, C. P. P. Oxygen Availability in Polyethylene Glycol Solutions and Its Implications in Plant-Water Relations. Plant Physiology 1975, No. 55, 20-24.
(65) Scherzer, T.; Langguth, H. Temperature Dependence of the Oxygen Solubility in Acrylates and Its Effect on the Induction Period in UV Photopolymerization. *Macromol. Chem. Phys.* 2005, 206 (2), 240-245.
(66) Choi, N. W.; Kim, J.; Chapin, S. C.; Duong, T.; Donohue, E.; Pandey, P.; Broom, W.; Hill, W. A.; Doyle, P. S. Multiplexed Detection of mRNA Using Porosity-Tuned Hydrogel Microparticles. *Anal. Chem.* 2012, 84 (21), 9370-9378.
(67) Lee, A. G.; Arena, C. P.; Beebe, D. J.; Palecek, S. P. Development of Macroporous Poly(Ethylene Glycol) Hydrogel Arrays Within Microfluidic Channels. *Biomacromolecules* 2010, 11 (12), 3316-3324.
(68) Xia, B.; Krutkramelis, K.; Oakey, J. Oxygen-Purged Microfluidic Device to Enhance Cell Viability in Photopolymerized PEG Hydrogel Microparticles. *Biomacromolecules* 2016, 17 (7), 2459-2465.

Supplemental (1) Fairbanks, B. D.; Schwartz, M. P.; Bowman, C. N.; Anseth, K. S. Photoinitiated Polymerization of PEG-Diacrylate with Lithium Phenyl-2,4,6-Trimethylbenzoylphosphinate: Polymerization Rate and Cytocompatibility. Biomaterials 2009, 30 (35), 6702-6707.
(2) Kizilel, S.; Pérez-Luna, V. H.; Tcymour, F. Mathematical Model for Surface-Initiated Photopolymerization of Poly(Ethylene Glycol) Diacrylate. *Macromol. Theory Simul.* 2006, 15 (9), 686-700.
(3) Jockusch, S.; Turro, N. J. Phosphinoyl Radicals: Structure and Reactivity. a Laser Flash Photolysis and Time-Resolved ESR Investigation. *J Am. Chem. Soc.* 1998, 120 (45), 11773-11777.
(4) Colley, C. S.; Grills, D. C.; Besley, N. A.; Jockusch, S.; Matousck, P.; Parker, A. W.; Towrie, M.; Turro, N. J.; Gill, P. M. W.; George, M. W. Probing the Reactivity of Photoinitiators for Free Radical Polymerization: Time-Resolved Infrared Spectroscopic Study of Benzoyl Radicals. *J. Am. Chem. Soc.* 2002, 124 (50), 14952-14958.
(5) Dendukuri, D.; Panda, P.; Haghgooie, R.; Kim, J. M.; Hatton, T. A.; Doyle, P. S. Modeling of Oxygen-Inhibited Free Radical Photopolymerization in a PDMS Microfluidic Device. *Macromolecules* 2008, 41 (22), 8547-8556.
(6) Decker, C.; Jenkins, A. D. Kinetic Approach of O2 Inhibition in Ultraviolet- and Laser-Induced Polymerizations. *Macromolecules* 1984, 18, 1241-1244.
(7) Majima, T.; Schnabel, W.; Weber, W. Phenyl-2,4,6-Trimethylbenzoylphosphinates as Water-Soluble Photoinitiators. Generation and Reactivity of O=P(C6H5) (O—) Radical Anions. *Makromol. Chem.* 1991, 2307-2315.
(8) Hristova, D.; Gatlik, I.; Rist, G.; Dietliker, K.; Wolf, J.-P.; Birbaum, J.-L.; Savitsky, A.; MÖbius, K.; Gescheidt, G. Addition of Benzoyl Radicals to Butyl Acrylate: Absolute Rate Constants by Time-Resolved EPR. *Macromolecules* 2005, 38 (18), 7714-7720.
(9) Jockusch, S.; Turro, N. J. Radical Addition Rate Constants to Acrylates and Oxygen: A-Hydroxy and A-Amino Radicals Produced by Photolysis of Photoinitiators. *J. Am. Chem. Soc.* 1999, 121 (16), 3921-3925.
(10) Scaiano, J. C.; Stamplecoskie, K. G.; Hallett-Tapley, G. L. Photochemical Norrish Type I Reaction as a Tool for Metal Nanoparticle Synthesis: Importance of Proton Coupled Electron Transfer. *Chem. Commun.* 2012, 48 (40), 4798-11.
(11) Jockusch, S.; Landis, M. S.; Freiermuth, B.; Turro, N. J. Photochemistry and Photophysics of A-Hydroxy Ketones. *Macromolecules* 2001, 34 (6), 1619-1626.
(12) Goodner, M. D.; Bowman, C. N. Development of a Comprehensive Free Radical Photopolymerization Model Incorporating Heat and Mass Transfer Effects in Thick Films. *Chemical Engineering Science* 2002, 57 (5), 887-900.

Example 2— Fabrication of Non-Spherical Hydrogel Particles for Drug Delivery

Abstract

Hydrogel microparticles have become an intensively studied platform for the delivery of drugs to treat many diseases, since they can be easily modified to enhance treatment efficacy. Conventional particle fabrication methods usually generate spherical particles, but there is an interest in producing non-spherical particles because particle shape has been shown to affect drug release profiles, particle degradation, transport in the body, and targeting abilities. There is a limited availability of techniques that produce non-spherical particles, amongst which microfluidics stands out because it allows precise dose control of each substance and facile functionalization of particle surfaces. However, current microfluidic methods are restricted by device geometry and capillary pressure, making it almost impossible to produce particles small enough (<10 µm) to be used for drug delivery applications. Using poly(ethylene glycol) diacrylate (PEGDA) as a model polymer platform, we describe a microfluidic technique to produce non-spherical hydrogel particles by taking advantage of oxygen inhibition, often undesirable, to control droplet size and shape. Briefly, due to oxygen diffusion and inhibition of the radical photopolymerization reaction, droplets polymerize from the core outward. This enables us to use larger and easily produced micro-droplets to fabricate independently sized particles by controlling the outer unpolymerized shell thickness. In a similar fashion, a variety of shapes, such as rods, discs, and wires, were produced by photopolymerizing deformed droplets as they traveled down channels with varying dimensions. Using this method, we were able to overcome the limitations in current microfluidic methods and produce non-spherical hydrogel.

Droplet Microfluidics

Figure 10:
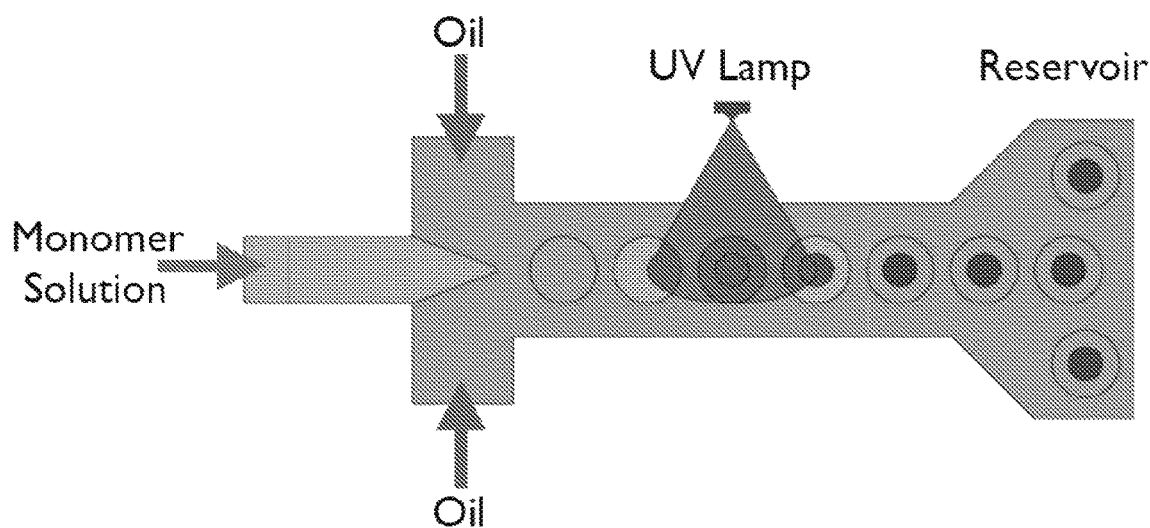
FIG. 10. provides an example devices for droplet microfluidics.

In droplet microfluidic, two immiscible phases interact to form discrete droplets due to high interfacial forces, a surfactant is used to stabilize these emulsions.[1] Microfluidic devices (as shown in FIG. 10) offer precise control over droplet formation, and allow us to control the volume and concentrations within single droplets.[2] These devices are usually made from PDMS (Polydimethylsiloxane), a transparent and easily molded material that is also highly permeable to gases.[3]

Oxygen Inhibited Droplet Photopolymerization

Figure 11:
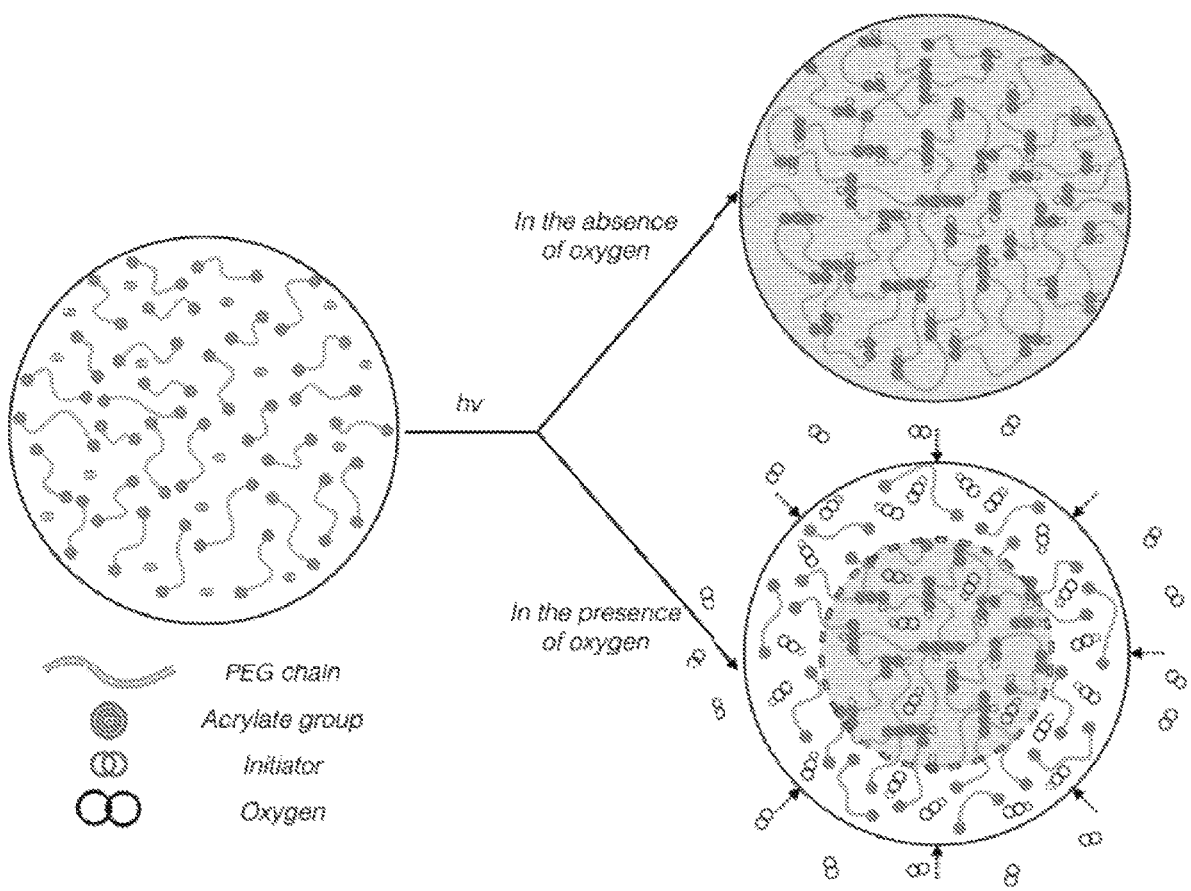
FIG. 11. illustrates Oxygen Inhibited Droplet Photopolymerization.

Photoinitiated chain polymerization of acrylated PEG precursors can be used to form gels with specific properties. Advantages include high reaction rates and high spatial control. In microfluidic devices, oxygen can permeate through the PDMS and into the droplets, leading to oxygen inhibition, which reduces the rate of polymerization and forms peroxy radicals as described in FIG. 11.[4,5]

Size Control

Figure 12:
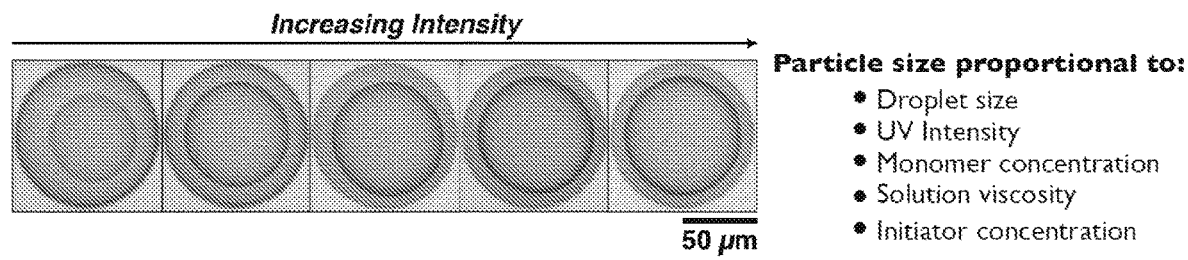
FIG. 12. demonstrates that particle size may be controlled.

Making homogeneous, monodisperse micro-scale droplets and polymerizing them in ambient conditions allows us to fabricate particles independent of particle size as illustrated in FIG. 12, reaching the lower limits of particle size without as many device operation constraints.

Particle Size is proportional to: Droplet size, UV intensity, monomer concentration, solution viscosity and initiator concentration.

Non-Spherical Particles

Shape, along with size and chemistry, is a critical feature of drug delivery particles. Particle degradation and release profiles for encapsulated molecules will be dictated by particle shape. Transport along the body will also be affected by particle shape due to particle velocity, diffusion, and adhesion. The particle's targeting ability is also dictated by the shape, since it impacts overall surface area and ligand and opsonin adsorption, as well as fitting the contours of target cell membranes.

Figure 13:
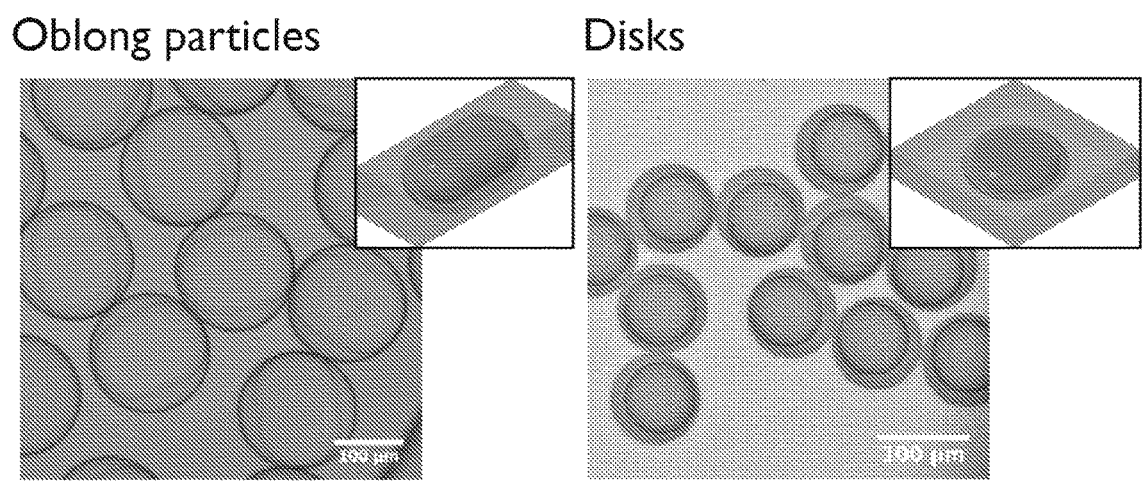
FIG. 13. provides examples of oblong and disk shaped particles.
Figure 14:
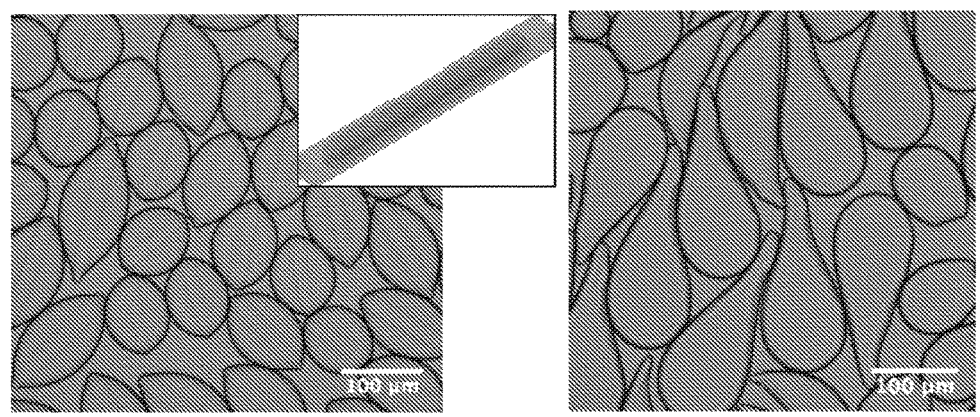
FIG. 14. provides examples of rod and wire shaped particles.
Figure 15:
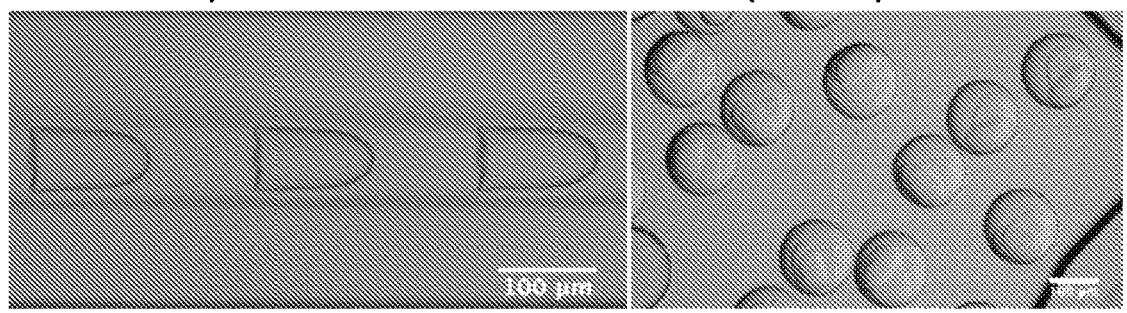
FIG. 15. provides examples of bullet shaped particles as well as particles that have been received multiple exposures.

Oblong and disk-shaped particles are illustrated in FIG. 13. Disk-shaped, flexible particles with diameters of ~10 μm routinely pass through the spleen; spherical particles require diameters under 200 nm to accomplish the same task. Rod shaped and wire shaped particles are illustrated in FIG. 14. Local curvature and surface area to volume ratio affect particle's targeting ability. More advanced shapes are also disclosed herein, for example, bullet shapes and particles after multiple exposures are provided in FIG. 15. Multiple exposure particles can possess regionally distinct mechanical properties.

Functional Surface

Surface chemistry influences the interactions of particles with cells and tissues in the body. For drug delivery purposes, we can tailor the surface properties to: 1) minimize recognition by the components of the immune system and 2) target carriers to specific tissues using targeting ligands such as antibodies and peptides.

Figure 16:
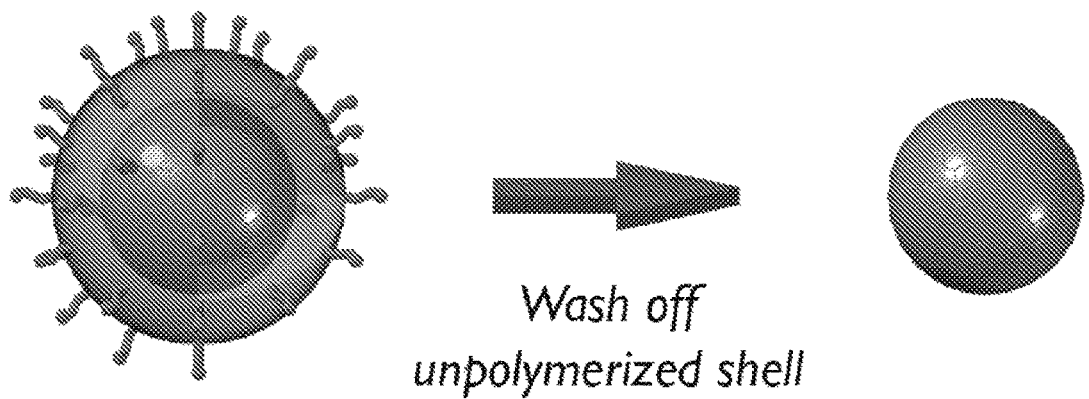
FIG. 16. illustrates that surfactant may be removed from the surface by not fully polymerizing the particle.

Fully polymerized particles retain a surfactant layer on the surface that hinders functionality. We can wash the unpolymerized layer to obtain a surfactant-free functional surface, as described in FIG. 16.

Figure 17:
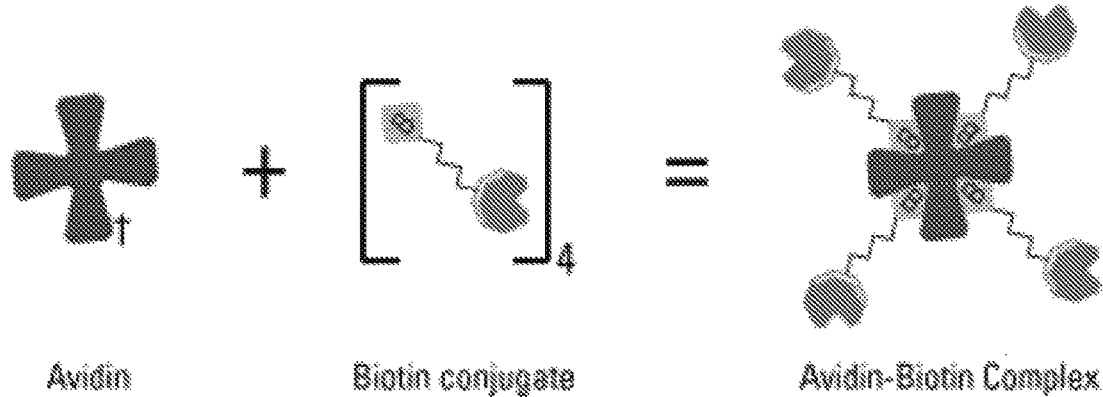
FIG. 17. illustrates that Acrylate-PEG-Biotin can be cross-linked into the hydrogel matrix.
Figure 18:
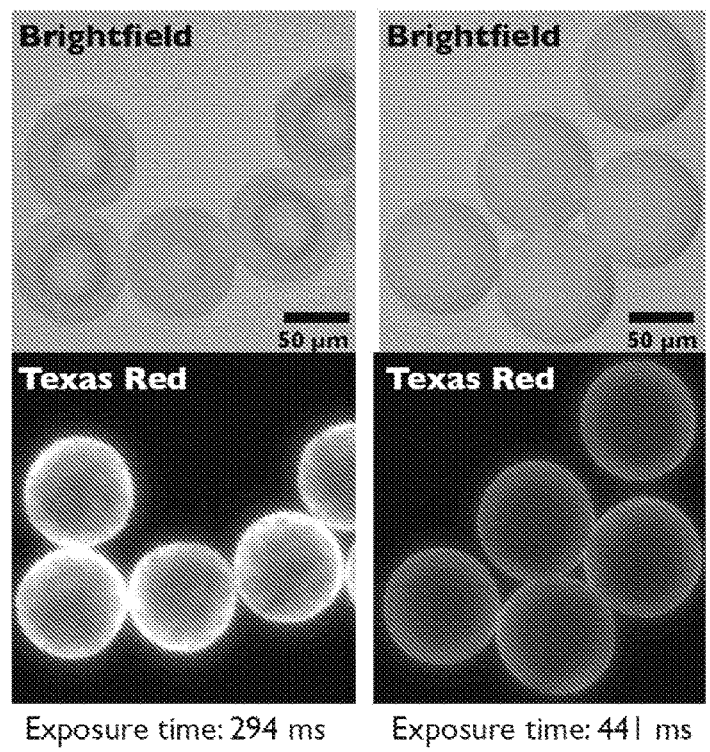
FIG. 18. shows fluorescent intensity correlates to biotin groups present at the interface. Particles exposed for less time show increased surface roughness.
Figure 19:
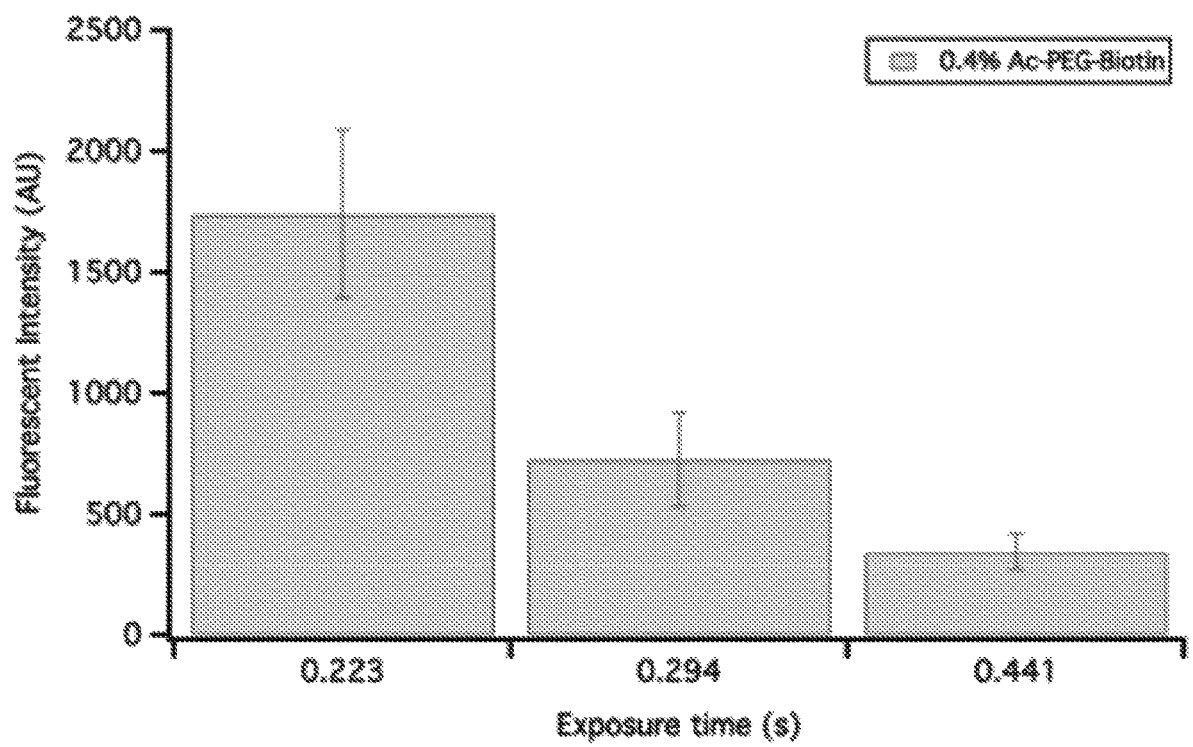
FIG. 19. Surface activity decreases with increasing exposure time due to crosslinking gradient at the particle surface.
Figure 20A:
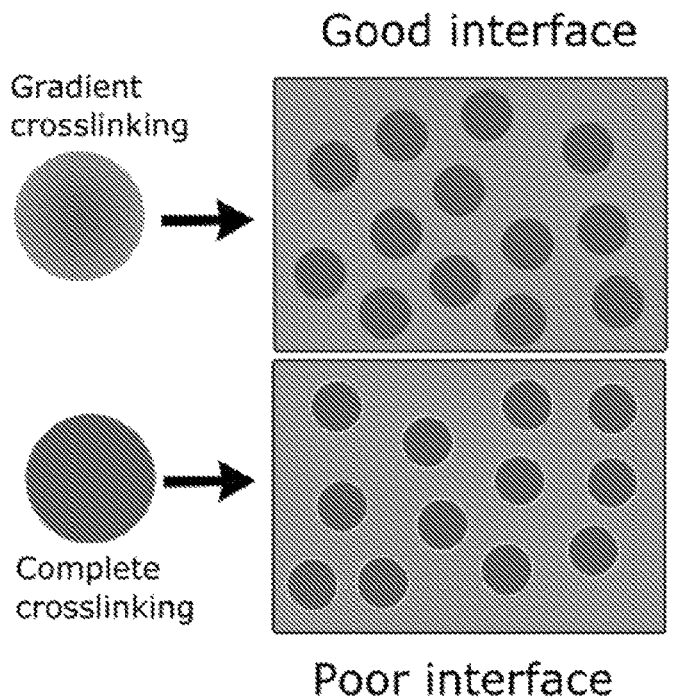
FIGS. 20A-20B. Schematic of effect of interfacial bonding on hydrogel properties.
Figure 20B:
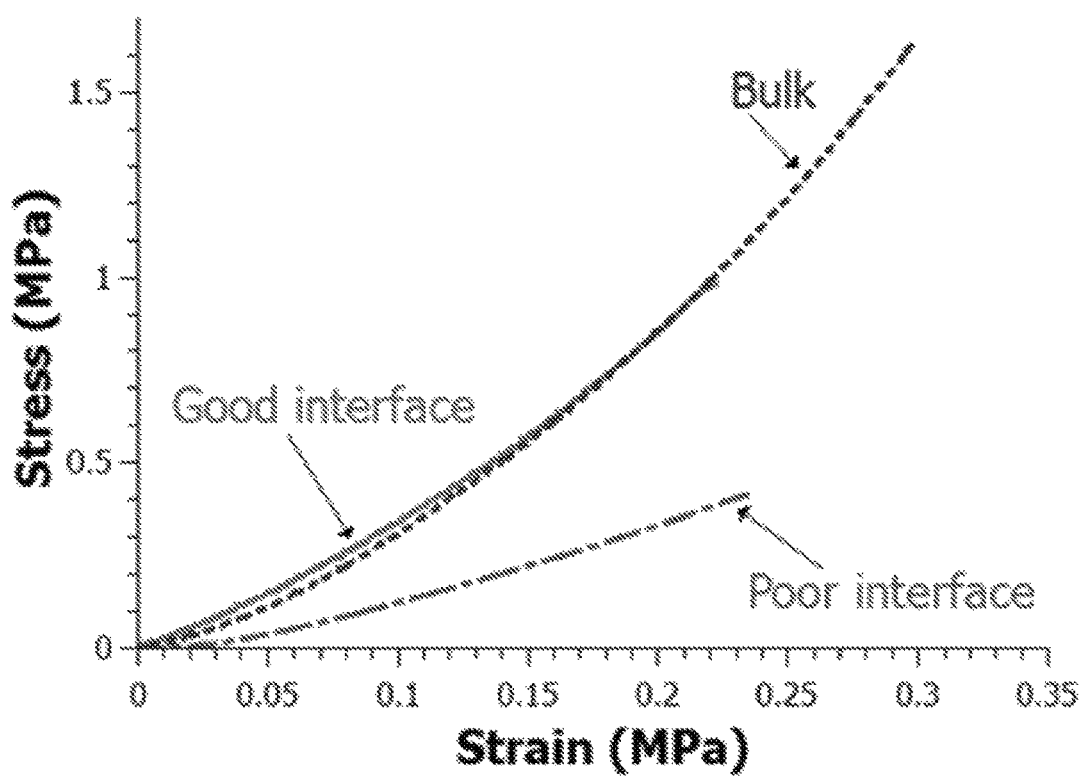
Figure 21A:
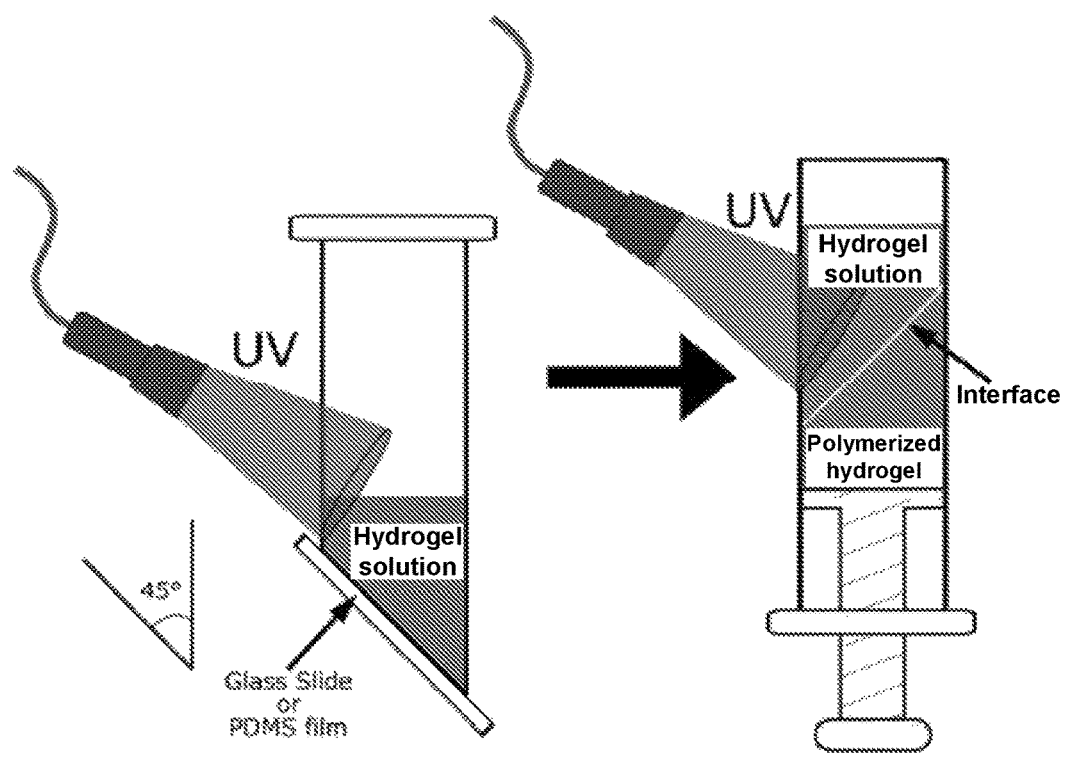
FIGS. 21A-B.
Figure 21B:
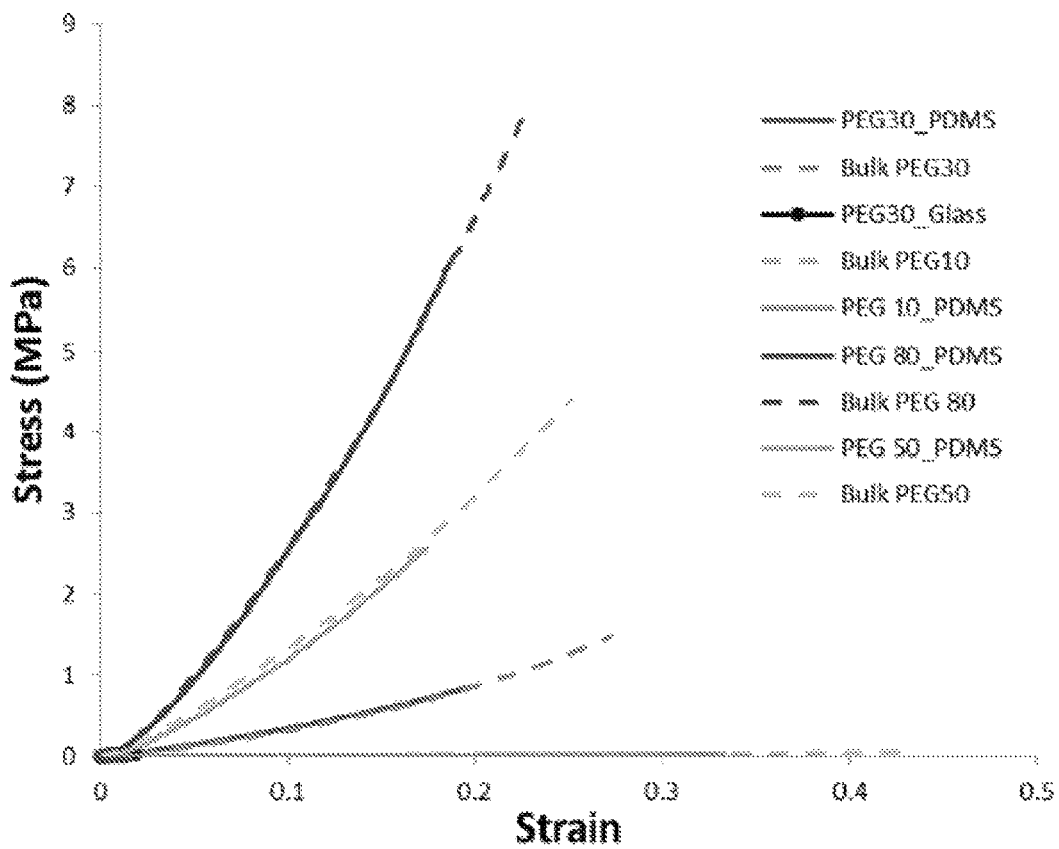
Figure 22:
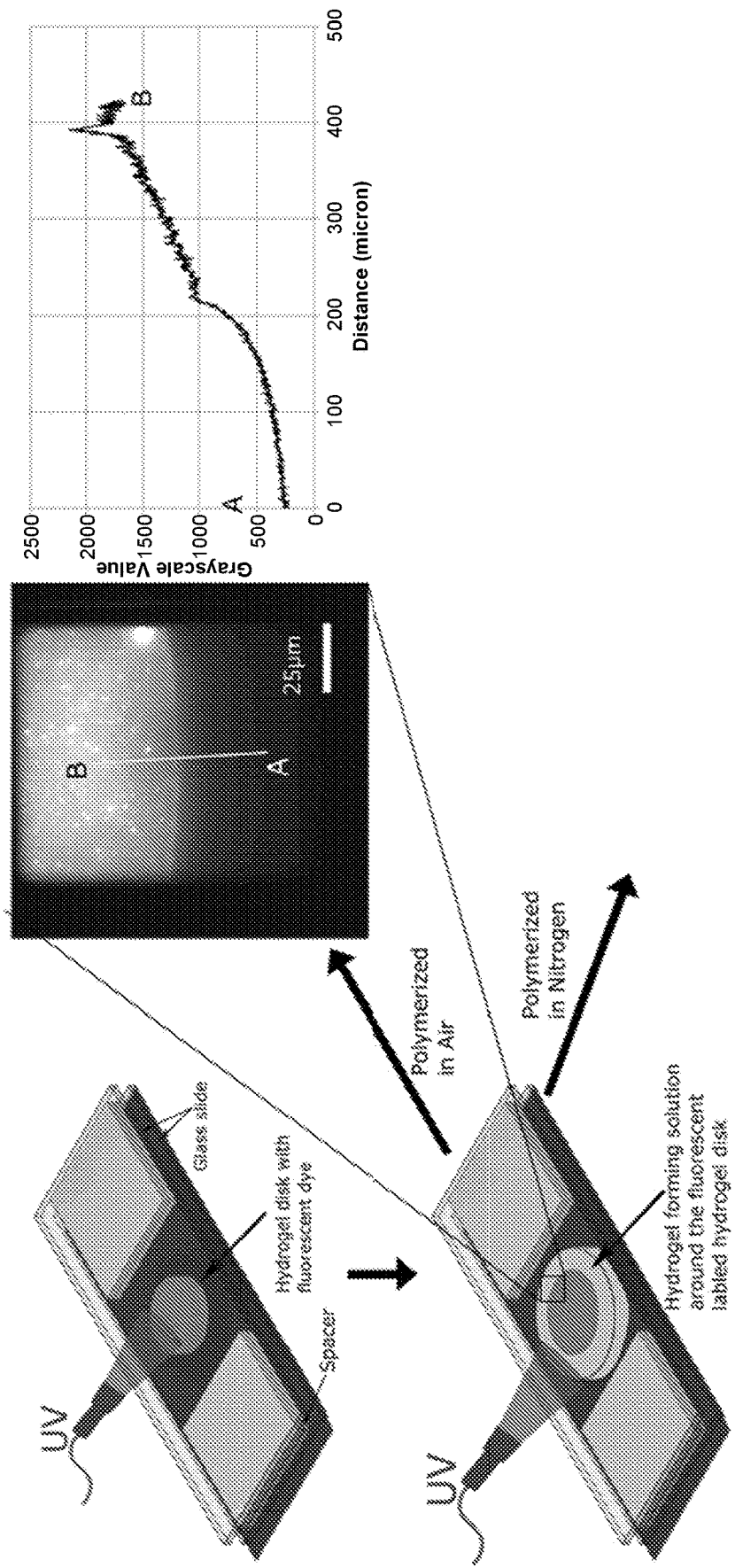
FIG. 22. (Left) Schematic diagram of the experimental setup to observe the hydrogel network at the fully- and partially-polymerized hydrogel surface. (Right) Fluorescent images show that gradual increase of the fluorescent at the interface for hydrogel polymerized in Air compared to steep increase for hydrogel polymerized in Nitrogen (This result is expected, however cannot be confirmed from the current results. Need to image in higher magnification). rhodamine at the surface polymerized against PDMS.
Figure 23A:
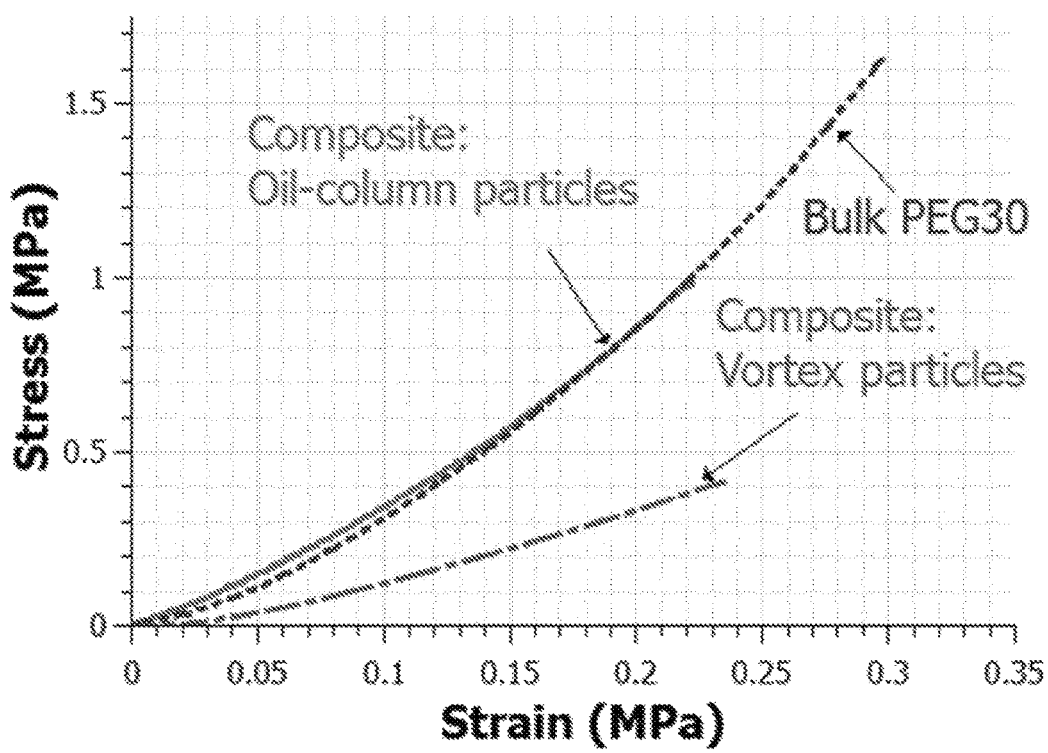
FIG. 23A. Composite hydrogel with hydrogel particles from vortex-suspension and oil-column method as well as hydrogel pieces. Composite hydrogel with vortex particles shows lower elastic modulus while composite with particles from oil-column shows bulk material similar elastic modulus.
Figure 23B:
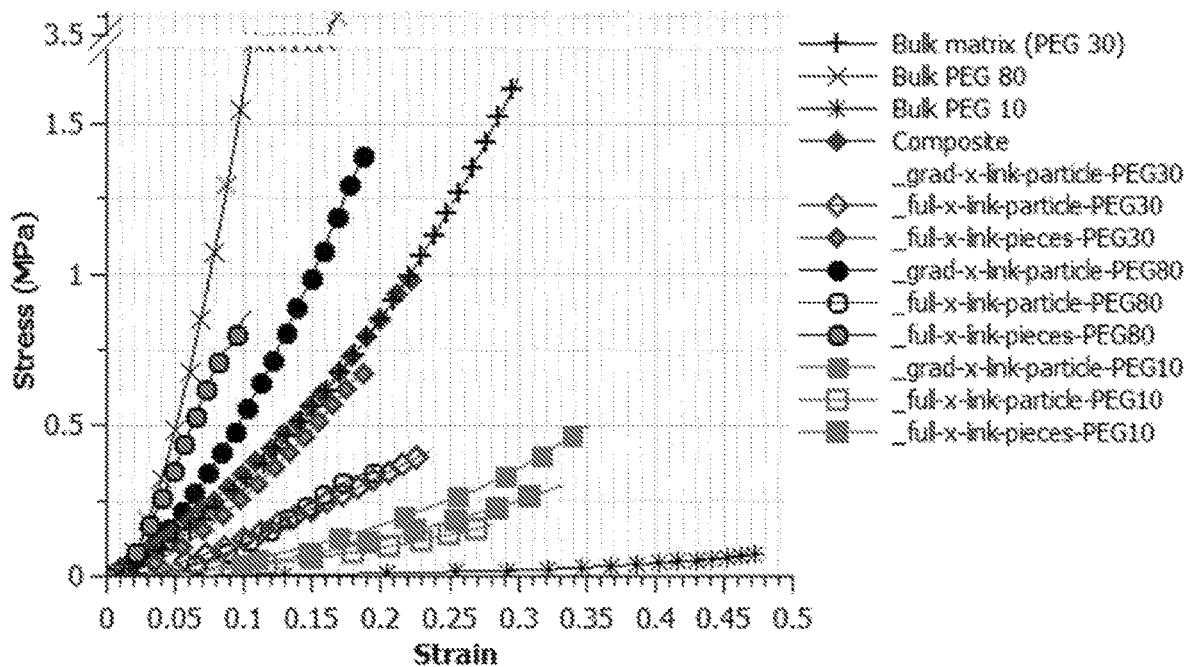
FIG. 23B. Composite made with soft-matrix and stiff-particles from oil-column method shows reinforcement, but particles from vortex suspension method deteriorate the overall composite behavior. Composites with small pieces from bulk hydrogel as discontinuous phase showed bulk hydrogel-similar modulus, but lower strength compared to composite with oil-column particles.
Figure 25A:
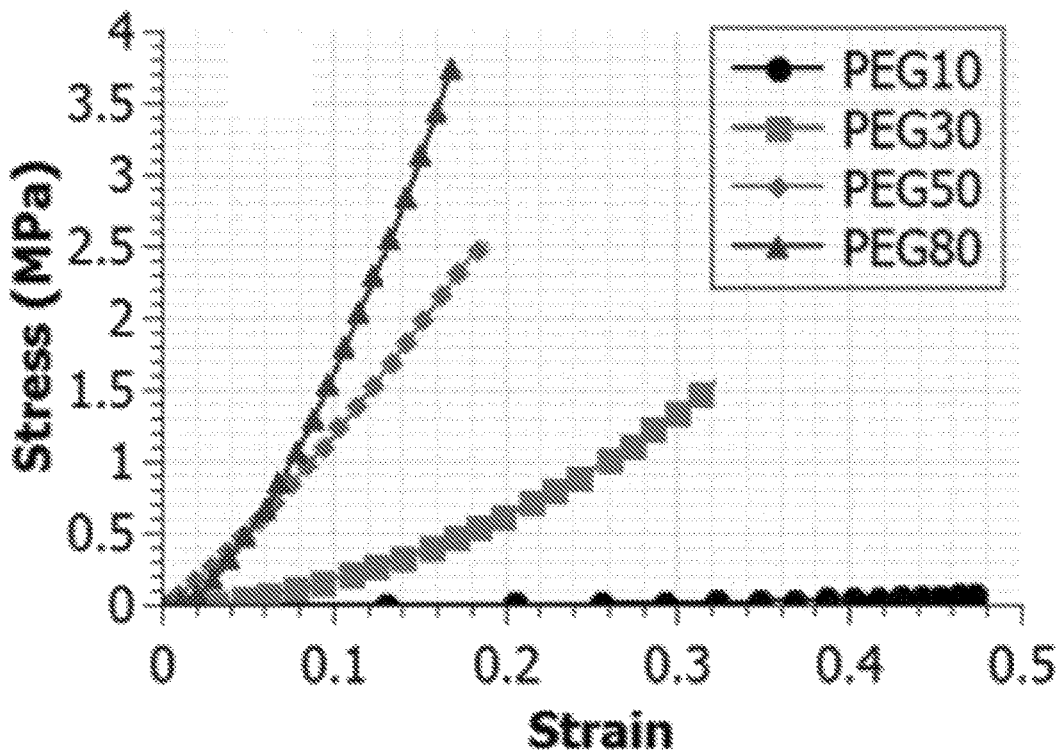
FIGS. 25A-25D. Composite with various volume fractions of vortex particles.
Figure 25B:
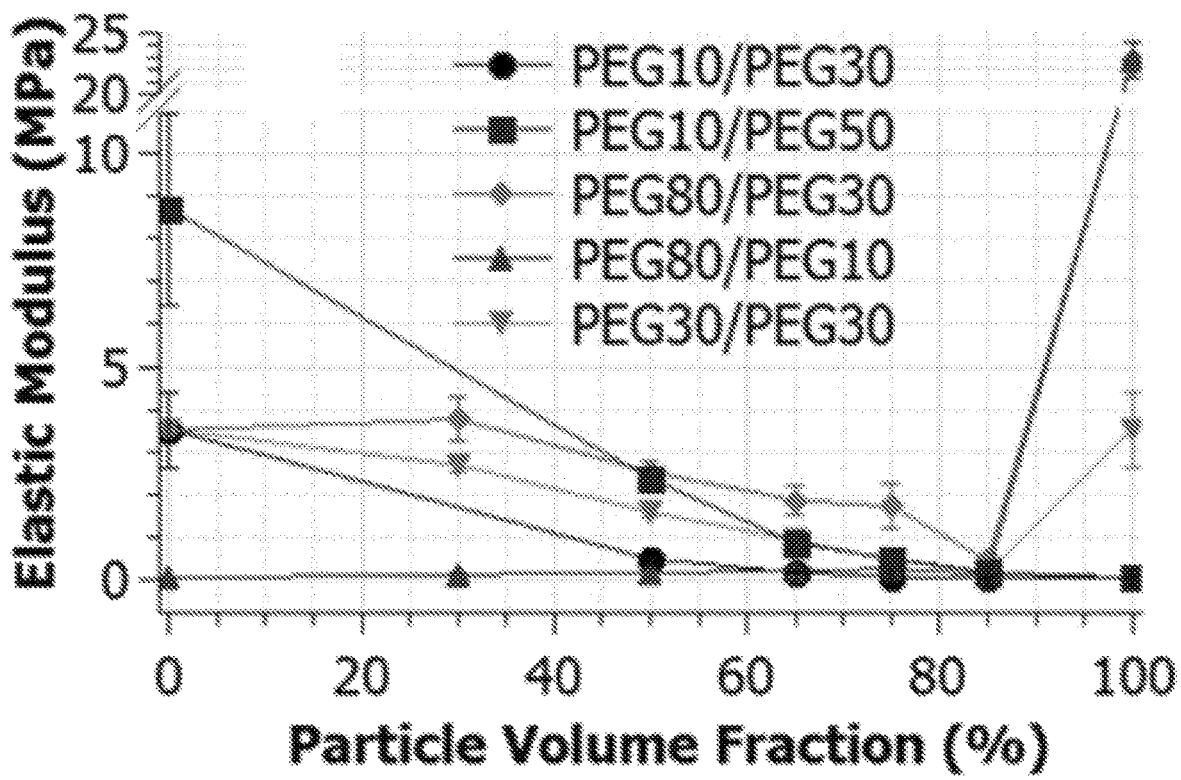
Figure 25C:
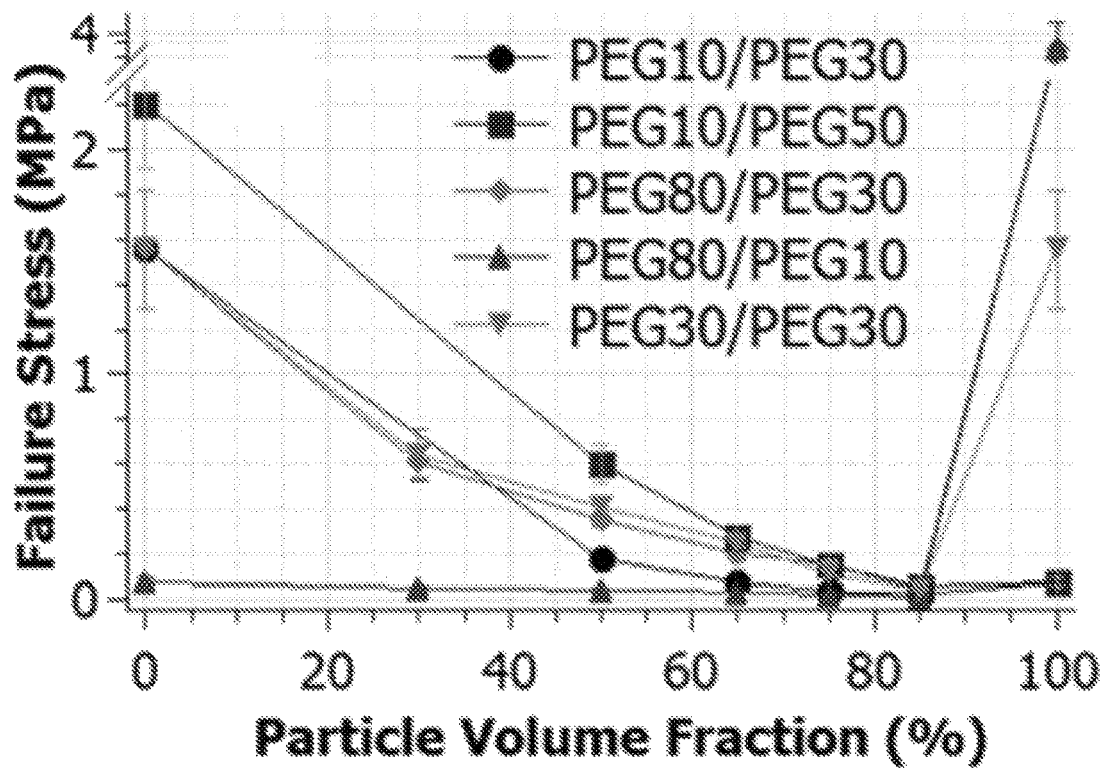
Figure 25D:
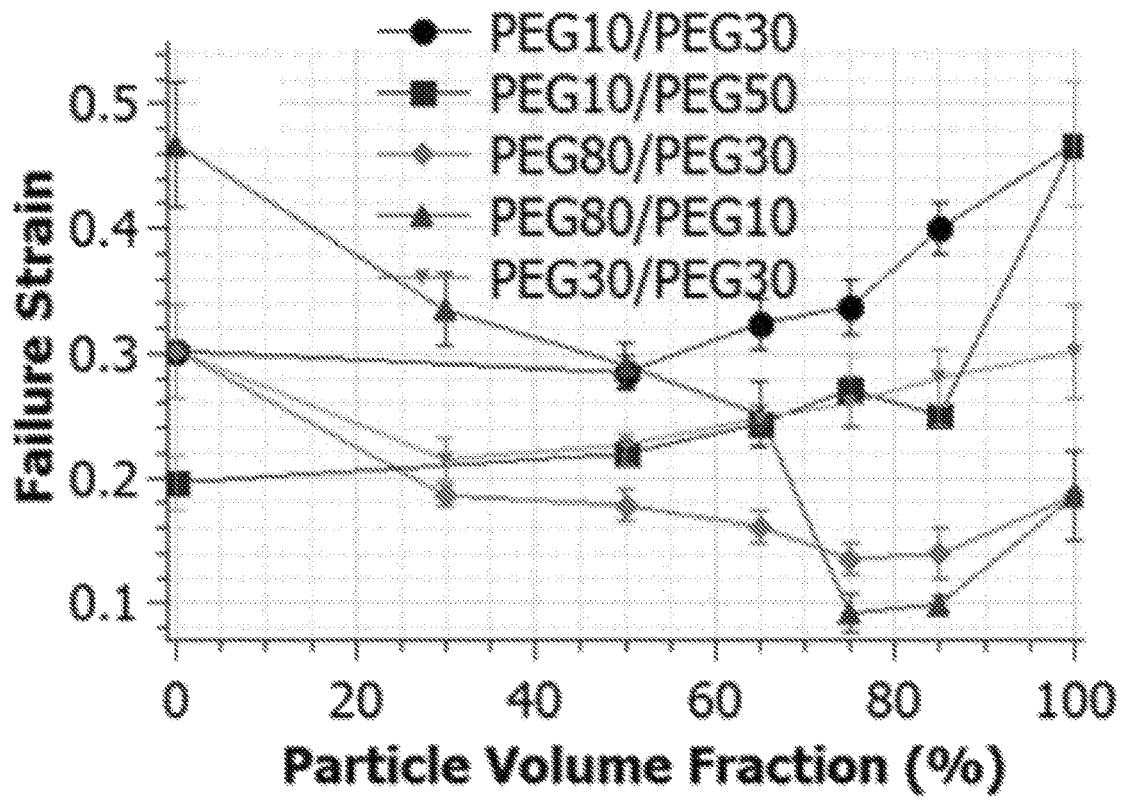
Figure 26:
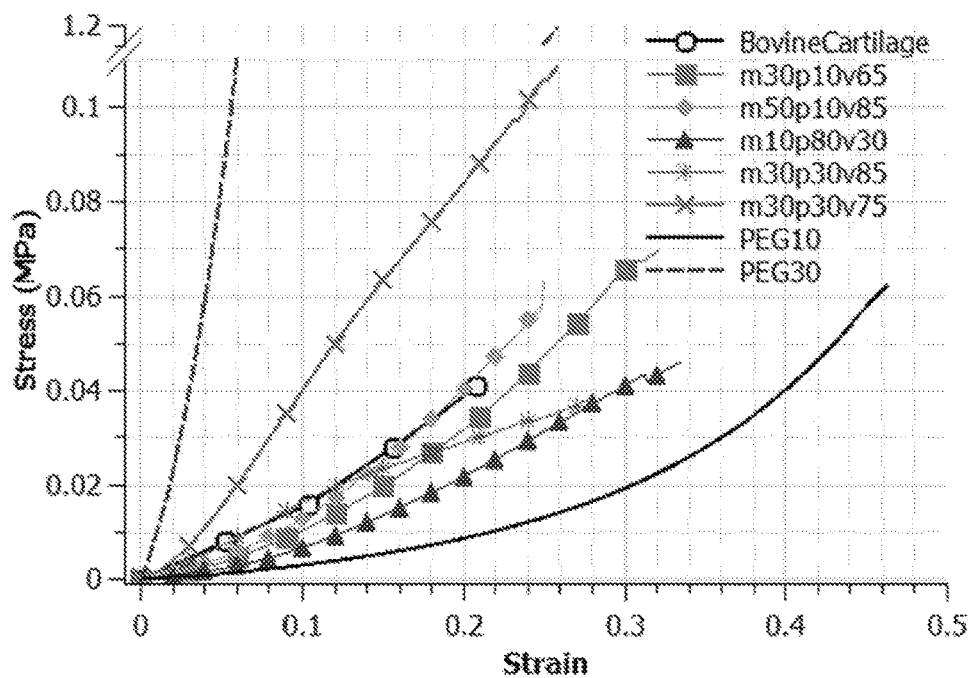
FIG. 26. Various composites with vortex particles match cartilage behavior showing possible applications.
Figure 27:
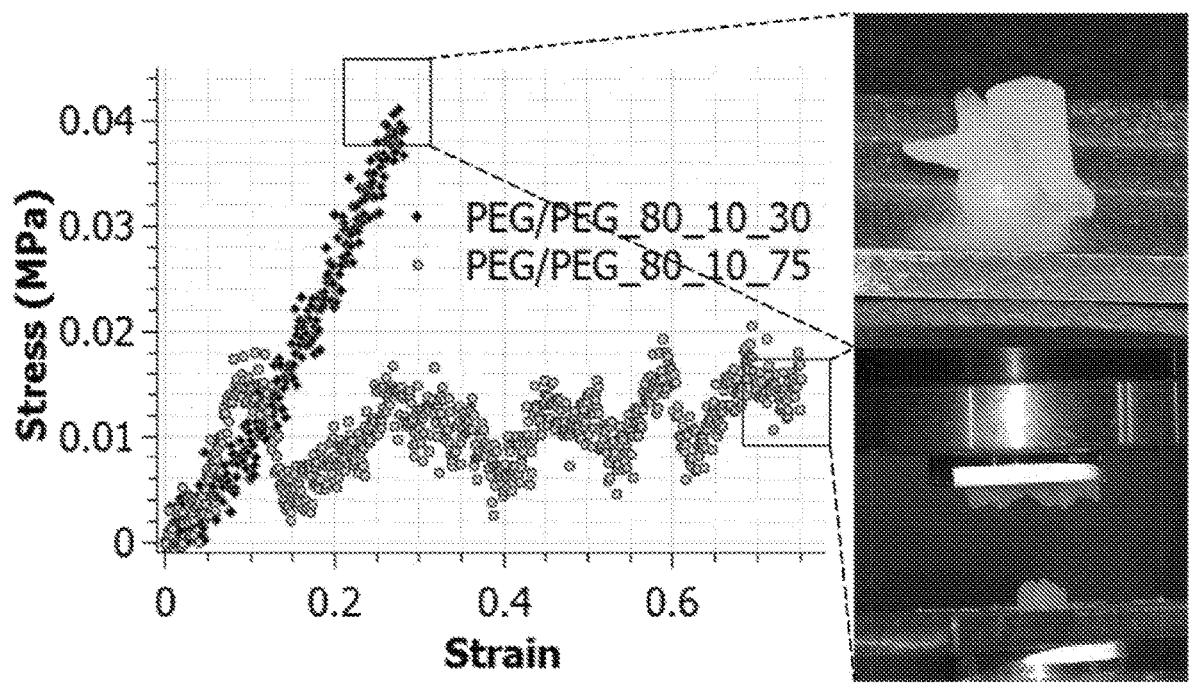
FIG. 27. Strain controlled test of composites with high volume fraction of stiff-vortex-particles shows debonding.
Figure 28:
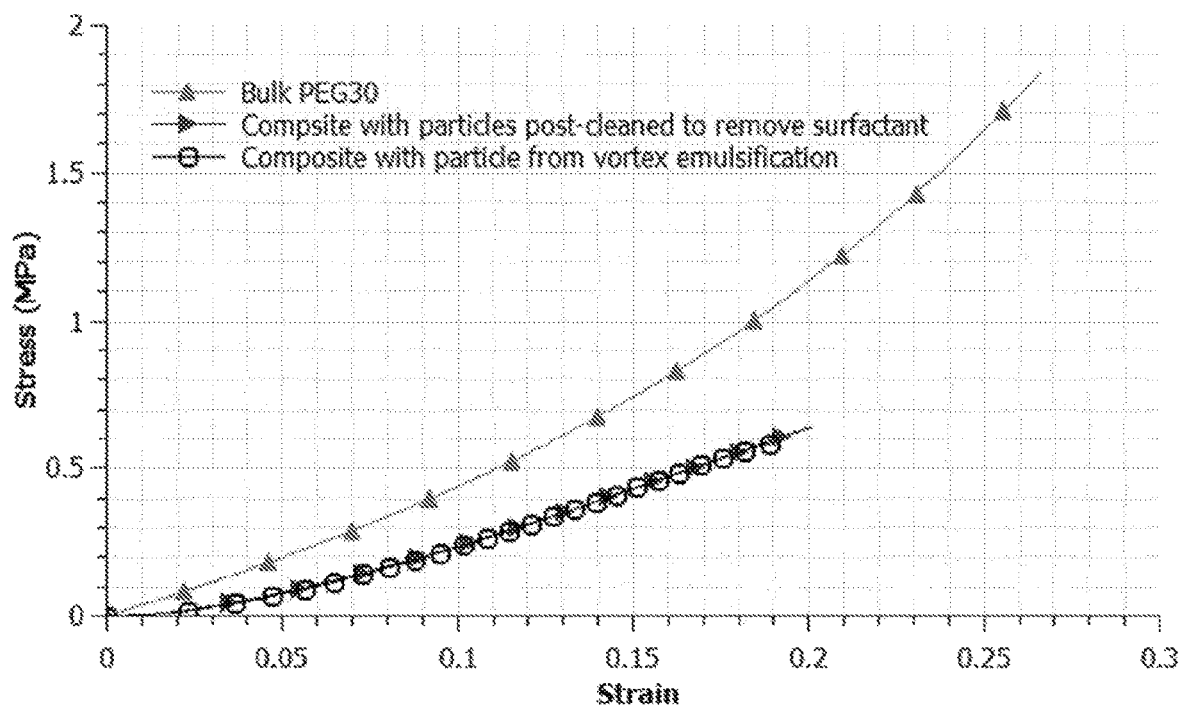
FIG. 28. Cleaning of vortex-particles with ethanol and acetone did not improve the composite modulus. This confirms that presence of surfactant in vortex particles cannot cause the poor interfacial bonding.
Figure 29A:
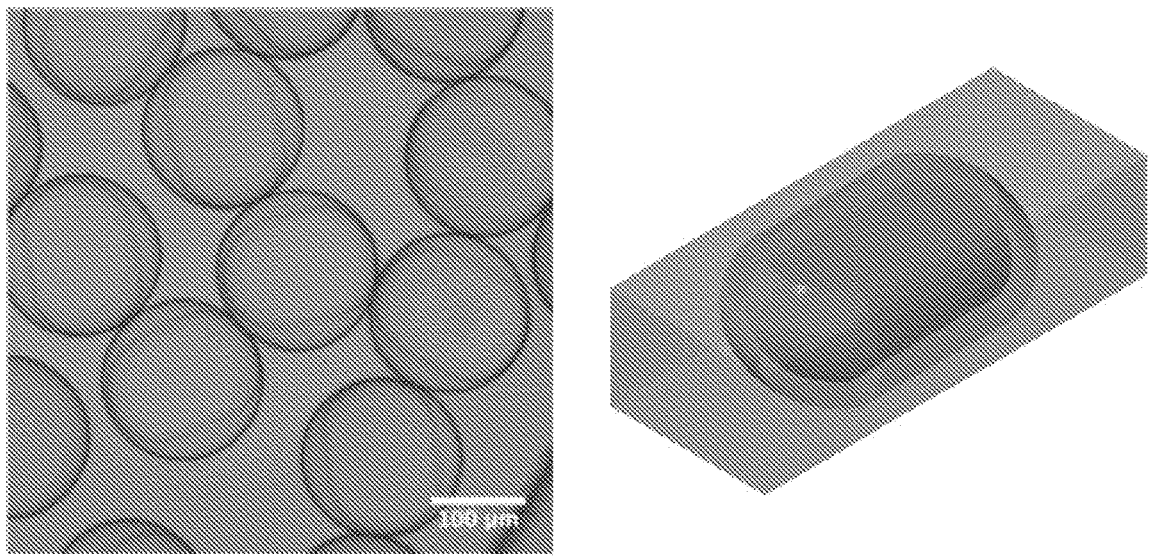
FIGS. 29A-29C. Size-controlled hydrogel particles with different shapes, such as oblong shapes (FIG. 29A), disks (FIG. 29B), and rods (FIG. 29C), can be produced in a high throughput fashion using droplet microfluidics in combination with oxygen-inhibited particle photopolymerization. Aqueous and oil phase flow conditions determine droplet volume; channel geometry dictates particle shape and aspect ratio; the particles final dimensions can be tuned using oxygen-inhibited photopolymerization.
Figure 29B:
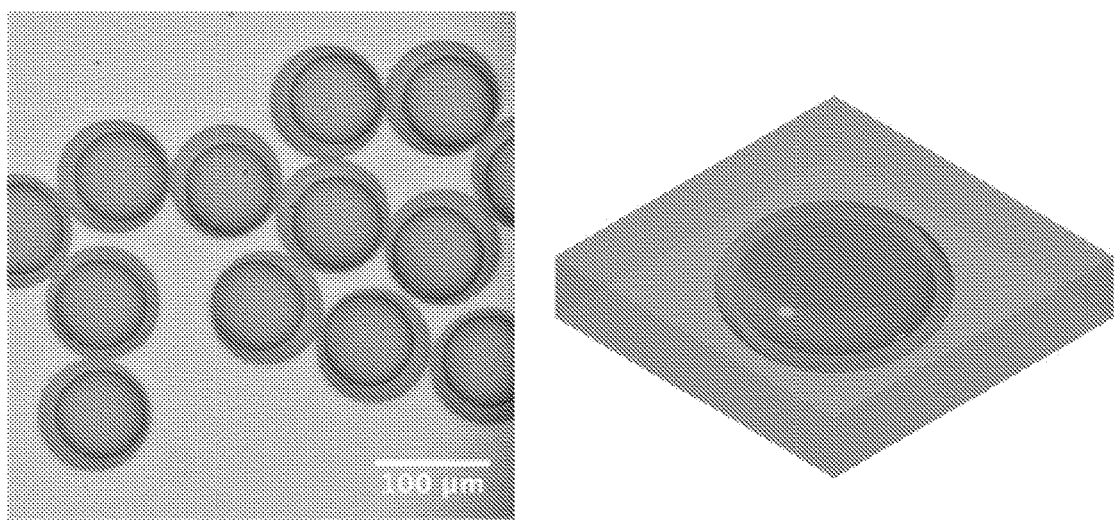
Figure 29C:
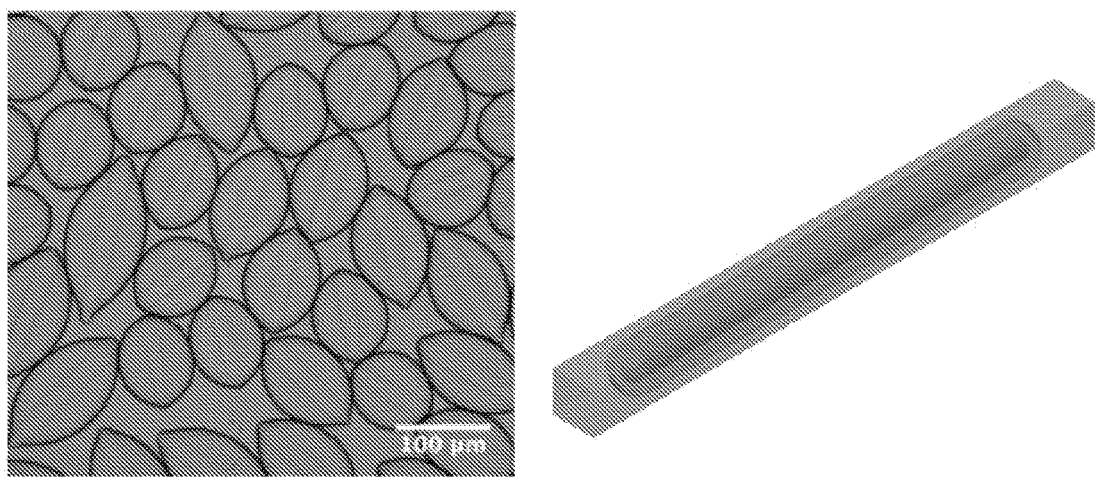
Figure 30:
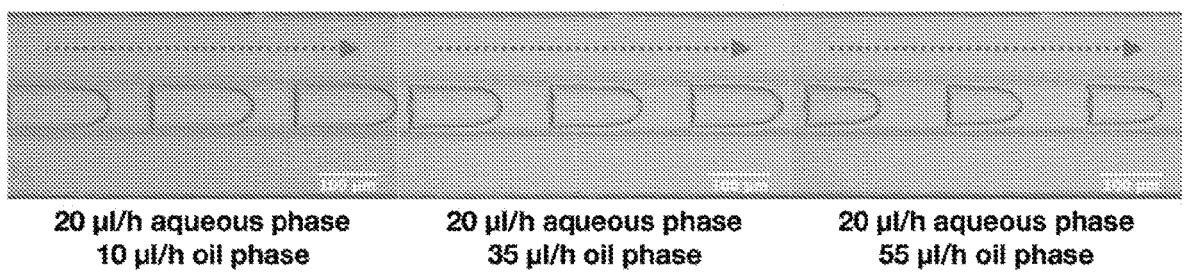
FIG. 30. Droplet deformation when using heavy mineral oil (viscosity>130 cP) combined with in situ photopolymerization provides the means to produce uniquely shaped particles from transient shapes. (Channel dimensions: width=100 µm; height=90 µm).
Figure 31:
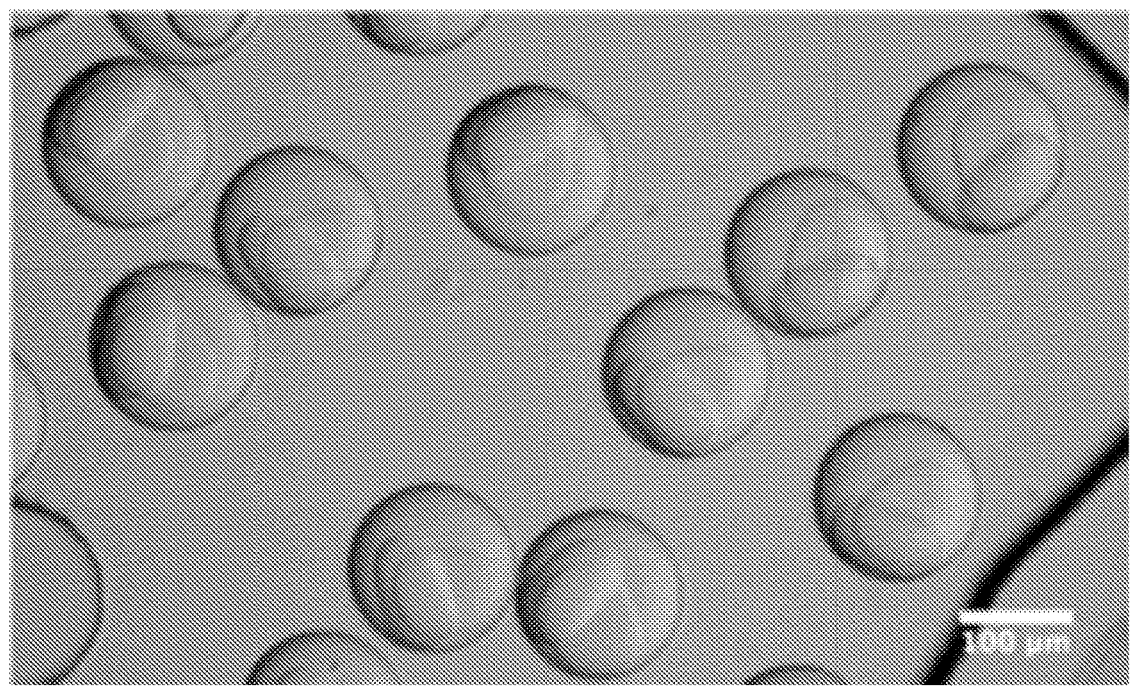
FIG. 31. Multiple exposure particles can possess regionally distinct mechanical properties.
Figure 32:
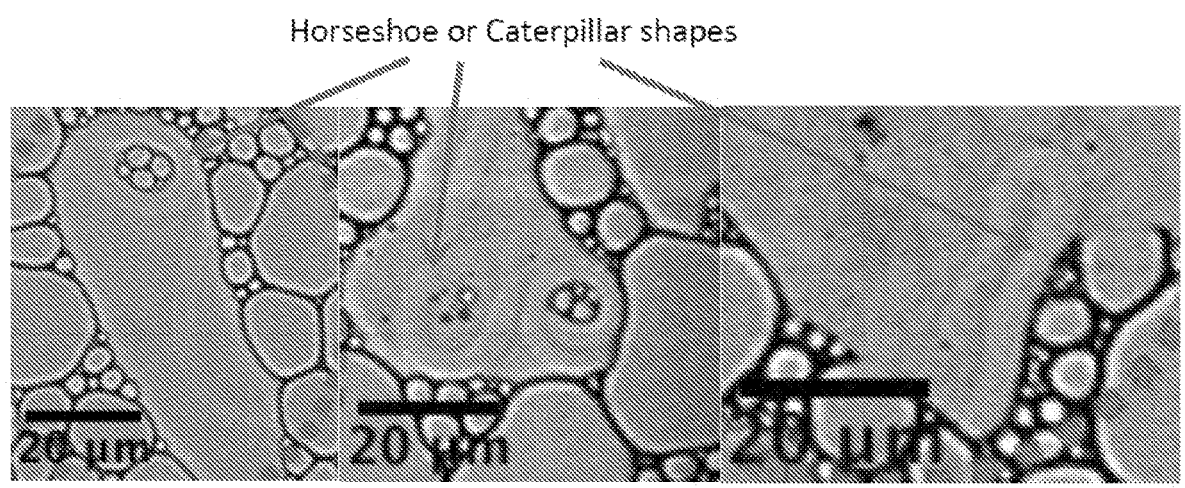
FIG. 32. Using glass-bonded PDMS microfluidic devices can produce hydrogel particles with crosslinking gradients due to asymmetric oxygen diffusivity profiles. In the pictures, elongated droplets were polymerized into wires with crosslinking gradients, resulting in diverse coiling patterns. (25 wt % PEGDA 700, 0.5% LAP).
Figure 33:
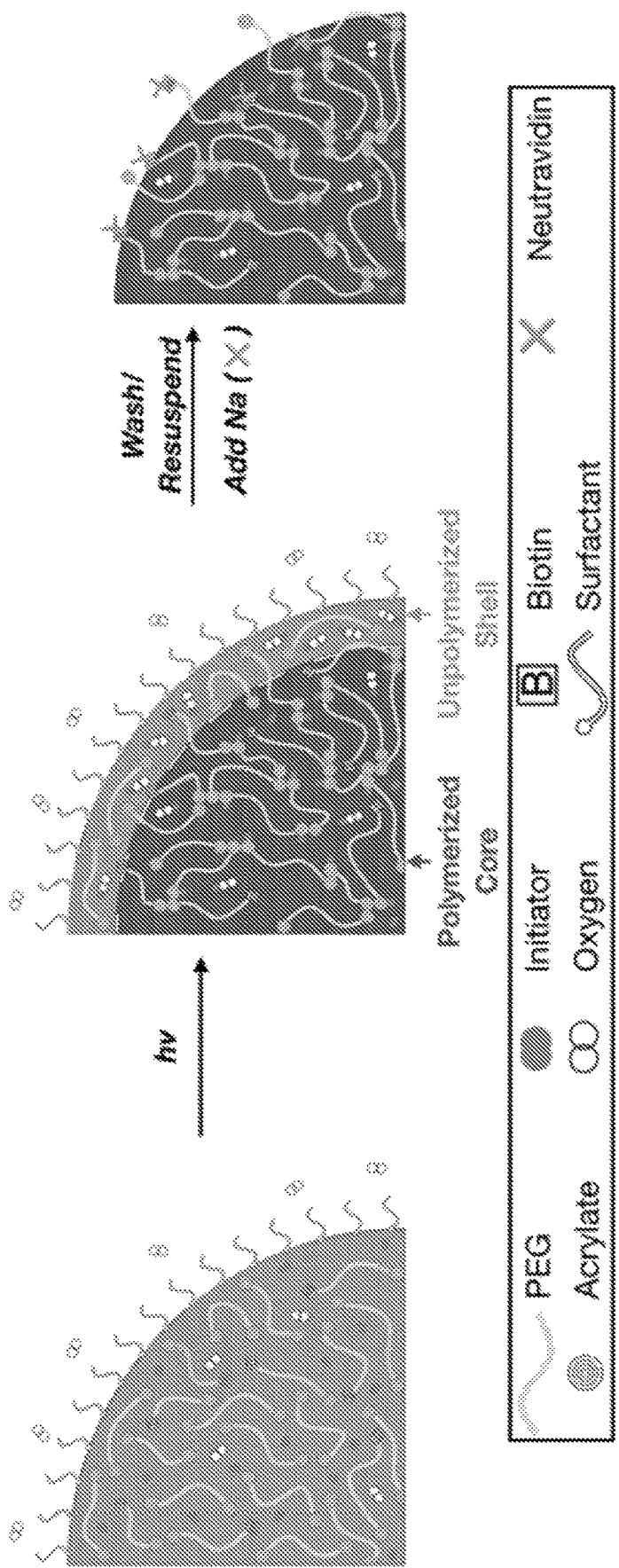
FIG. 33. Schematic of surface-functionalized hydrogel particle fabrication via oxygen-inhibited photopolymerization of droplets within a microfluidic device.
Figure 34A:
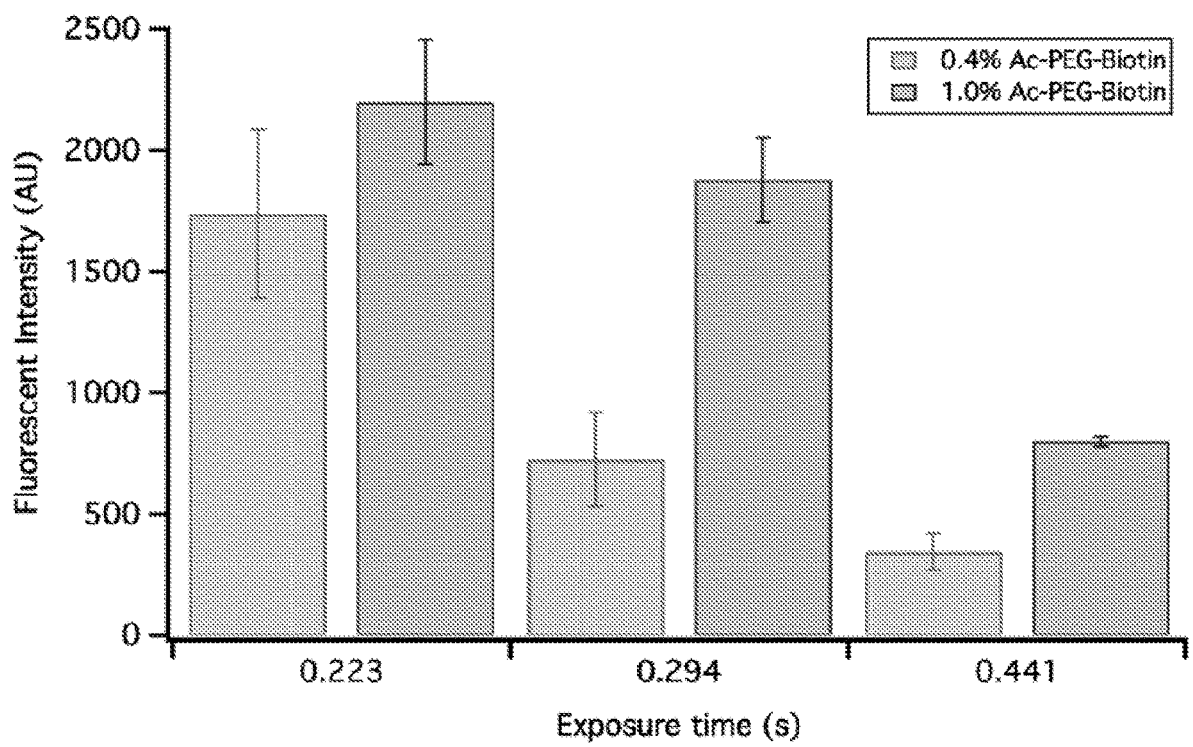
FIGS. 34A-34B. Influence of photopolymerization exposure time (30% PEGDA 700, 0.5% LAP, 1.0% Ac-PEG-Biotin 2 k)
Figure 34B:
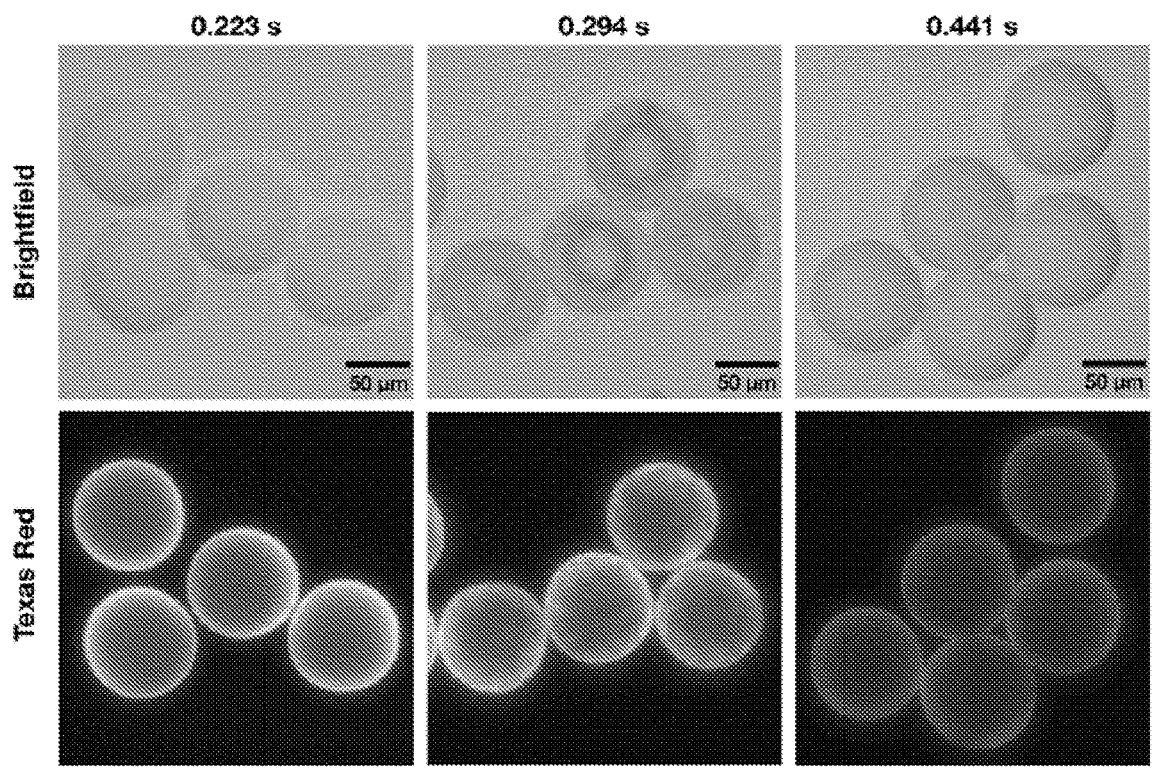

Acrylate-PEG-Biotin can be cross-linked into the hydrogel matrix as shown in FIG. 17. Biotin groups will be present on the particle surface, and in combination with a fluorescent avidin, displays visibly measurable activity. In FIG. 18 provides an example using 0.4% Ac-PEG-Biotin, 30% PEGDA 700 and 0.5% LAP. Fluorescent intensity correlates to biotin groups that are present at the interface. Particles exposed for less time show increased surface roughness. FIG. 19 illustrates that surface activity decreases with increasing exposure time due to crosslinking gradient at the particle surface.

REFERENCES (1) Teh, S.-Y.; Lin, R.; Hung, L.-H.; Lee, A. P. Droplet Microfluidics. *Lab Chip* 2008, 8 (2), 198-23.
(2) Tan, Y.-C.; Fisher, J. S.; Lee, A. I.; Cristini, V.; Lee, A. P. Design of Microfluidic Channel Geometries for the Control of Droplet Volume, Chemical Concentration, and Sorting. *Lab Chip*
(3) Kim, M.-C.; Lam, R. H. W.; Thorsen, T.; Asada, H. H. Mathematical Analysis of Oxygen Transfer Through Polydimethylsiloxane Membrane Between Double Layers of Cell Culture Channel and Gas Chamber in Microfluidic Oxygenator. Microfluid Nanofluid 2013, 15 (3), 285-296.
(4) Dendukuri, D.; Panda, P.; Haghgooie, R.; Kim, J. M.; Hatton, T. A.; Doyle, P. S. Modeling of Oxygen-Inhibited Free Radical Photopolymerization in a PDMS Microfluidic Device. *Macromolecules* 2008, 41 (22), 8547-8556.
(5) Krutkramelis, K.; Xia, B.; Oakey, J. Monodisperse Poly(ethylene) Glycol Diacrylate Hydrogel Microsphere Formation by Oxygen-Controlled Photopolymerization in a Microfluidic Device. *Lab Chip* 2016, 16 (8), 1457-1465.

Example 3—Engineering Functional Hydrogel Microparticle Interfaces by Controlled Oxygen-Inhibited Photopolymerization Abstract Functional poly(ethylene glycol) diacrylate (PEGDA) hydrogel microparticles for the detection of bioactive macromolecules were fabricated via oxygen-inhibited photopolymerization in a droplet microfluidic device. Hydrogel network functionalization and architecture were characterized using a biotin-avidin binding assay, which revealed radial network inhomogeneities dependent on exposure conditions. Empirical results were corroborated using a reaction-diffusion model, describing the effects of exposure intensity on the spatial photopolymerization kinetics and resulting polymeric mesh network. The combination of finely controlled exposure conditions and predictive simulations enables the generation of tailored particles with microengineered interfaces and gradients in crosslinking density, which dictate solute diffusivity and elasticity, augmenting the utility of this approach in engineering multifunctional, size-excluding hydrogel particles for multiplexed biomolecular sensing.

Introduction

Synthetic, photopolymerized hydrogels are versatile and widely used biomaterials that consist of highly crosslinked, water-swollen, sample-spanning polymer networks. Techniques to tailor hydrogel network properties are commonly used to control the conjugation, steric encapsulation, and release of bioactive macromolecules. Hydrogels composed of poly(ethylene glycol) diacrylate (PEGDA) have attracted particular and widespread interest due to their fabrication versatility and high degree of tunability. Diacrylated PEG-containing block copolymers have been used to form hydrogels with dynamic network properties enabling them to be used for a diversity of applications in various microenvironments. Photoinitiated polymerization lends exquisite spatial and temporal control over polymerization kinetics as well as the ability to lithographically pattern PEGDA hydrogel structures with dimensions on the micrometer scale. Microscale hydrogels have been used as drug delivery vehicles, tissue scaffolds, biosensors, and diagnostic platforms.

Various applications for hydrogels benefit from the direct conjugation of functional moieties to the hydrogel network in order to impart heterogeneous spatial properties and function.[10,11] Biosensing applications particularly rely on the copolymerization of proteins and enzymes in the hydrogel network for detection and quantification of specific analytes.[12-14] Hydrogel microparticle-based biosensing platforms possess many advantages over benchtop techniques, such as low cost, greater detection sensitivity, small sample consumption, multiplexing, and the ability to perform on-site analysis. [15-18] Hydrogel microparticles have been produced via a variety of methods, including suspension, emulsion, and precipitation polymerization and photolithographic techniques.[19] Stop flow lithography (SFL) has many advantages over batch techniques due to its fine control over particle size, shape, and network properties and has been used to fabricate bar-coded hydrogel microparticles for multiplexed protein and nucleic acid detection and quantification.[20,21] The introduction of mesh size gradients in hydrogel microparticles generated using SFL further increases detection specificity by incorporating molecular size exclusion capabilities, enabling the size-selective sieving of molecules such as mRNA.[22,23] Despite its versatility, SFL can only generate particles with internal mesh size gradients via macromer molecular weight gradients formed by laminar flow lithography[21] or gradient generators,[24] or through the use of porogens.[22] SFL is also an inherently low throughput (<5 Hz) production method.[21] To address these challenges, here we report a high-throughput technique that enables the continuous generation of hydrogel particles with complex and tunable network properties without the need for porogens or graded material precursors Droplet microfluidics, a technique used to produce emulsion droplets by merging two coflowing immiscible fluid phases, has emerged as a versatile and high-throughput alternative, allowing the continuous production of monodisperse microparticles[25] that can be easily functionalized.[25] Polydimethylsiloxane (PDMS) is commonly used to construct droplet microfluidic devices, because it is inexpensive, hydrophobic, and transparent, which facilitates imaging and coupling of a UV light source to photopolymerize flowing droplets in situ.[27] The high gas permeability of PDMS, combined with the high oxygen solubility of fluorocarbon carrier oils commonly used for droplet formation, renders droplets polymerized in PDMS-based microchannels susceptible to oxygen inhibition.[28] This phenomenon refers to the quenching of primary initiating or propagating radicals by oxygen to form peroxyl radicals. Since peroxyl radicals do not initiate acrylate double bond conversion, radical chain polymerization cannot proceed until dissolved oxygen is consumed almost completely.[29,30] The competition between the diffusion and consumption of oxygen is evident in droplets due to the constant replenishment of oxygen over the short diffusion length scales across the oil-aqueous interface to the aqueous core. As a consequence, exposed droplets possess a polymerized core and unpolymerized shell, with the thickness of shell being determined by the diffusion and reaction of oxygen. While generally deleterious to many biological applications,[31] oxygen inhibition has been previously exploited to produce hydrogel particles in droplet templates with precise size control.[32] Additionally, a predictive reaction-diffusion model was developed to fully describe particle-to-droplet diameter ratio as a function of processing parameters during oxygen-inhibited particle photopolymerization in emulsion droplets Controlled oxygen-inhibited droplet photopolymerization presents a unique platform in which immunofunctional hydrogel particles with precisely microengineered interfaces can be produced in a high-throughput fashion. Further, rigorous control over exposure conditions enables exquisite manipulation of the internal network architecture of these particles without the need for porogens. This technique is demonstrated by fabricating particles with biotin-decorated hydrogel networks which are subsequently incubated within a fluoro-neutravidin solution. Specific binding of the tagged ligand reveals the availability of copolymerized functional groups at the particle surface and neutravidin's (NA) accessibility to the particle interior. Additionally, experimental results are corroborated with a reaction-diffusion model that describes the effect of photopolymerization kinetics on local hydrogel network architecture. The integrated approach of combining experimental results and model prediction enables the fabrication of particles with a range of controllable spatial gradients in their degree of crosslinking. For example, weakly crosslinked particles allow NA to diffuse across their entire radius, while the highly crosslinked particles are completely impenetrable to NA. As crosslinking increases, biotin accessibility becomes sterically constrained entirely by the polymeric mesh network. These bounding cases highlight the tractability of this fabrication approach and illustrate the importance of considering photopolymerization conditions when microfabricating particles for biosensing applications. Particles fabricated by this platform can be designed with gradients in crosslinking density, diffusive conductivity, and elasticity, highlighting the utility of this approach in engineering multifunctional, size-excluding hydrogel particles for biomolecular sensing.

Experimental Section

Hydrogel forming solution preparation: A solution composed of 0.38 M PEGDA 700, 17 mM Lithium phenyl-2, 4.6-trimethylbenzoylphosphinate (LAP), and 2.1 mM Acryl-PEG-Biotin (2000 Da) in a phosphate buffered saline (PBS, GenClone) was used as the aqueous phase, and a fluorocarbon oil (Novec 7500+2% Picosurf 1, Dolomite) was used as the oil phase for the microfluidic droplet process.

Neutravidin-Rhodamine preparation: Neutravidin (Na) was conjugated to NHS-Rhodamine (NHS—Rh) according to the protocol provided by Thermo Scientific, and diluted to a concentration of 0.43 mg/ml.

Microfluidic device preparation and operation: Flow focusing PDMS microfluidic devices were prepared using standard soft lithography techniques. [33] Briefly, a two layer photoresist pattern was fabricated by two sequential UV exposure steps with two different photomasks to obtain different channel depths for each device section: 30 µm for the droplet pinch-off section, and 110 µm for the downstream photopolymerization section.

Liquid flow was delivered to and controlled within the device using a series of syringe pumps (neMESYS), flowing at 20 µl/hr for the aqueous phase, 40 µl/hr for the droplet pinch-off oil phase, and 140 µl/hr for the downstream oil phase. At these flow rates, droplets with diameters of 100 µm were formed and exposed for 708±15 ms. Droplets were photopolymerized using a white light LED source with a DAPI filter (350-400 nm) and a 10×objective (Olympus UPlanFLN 10×/0.30Ph1). After collecting particles for 15 minutes, 1 ml of deionized water was added, and the mixture was vortexed for 30 s to wash off the unpolymerized shell, after which the particles were separated from the oil and most of the water using a 5 μm centrifuge filter (1350 rpm for 5 min), and recovered particles were resuspended in 400 μl of PBS. 30 μl aliquots of the particle mixture were combined with 7.5 μl of the Na—Rh solution and mixed for two days, after which the particles were washed and resuspended in 100 μl PBS, incubated for 2 days to allow unincorporated Na—Rh to diffuse out, and imaged. For fluorescent imaging, a 20× objective was used in combination with a white light source filtered with a Texas Red filter cube (Ex: 535-580 nm, Em: 590-670 nm). A high-resolution camera (QIClick, QImaging) was used to collect images of 30 particles for each exposure intensity, using an exposure time of 100 ms. ImageJ was used to obtain an averaged radial profile of the fluorescent intensity for each particle, and after normalizing each data set, the average profile was calculated.

Confocal images were acquired using an Olympus IX-81 microscope equipped with a Yokogawa spinning disk (CSU X1) and a scientific complementary metal-oxide semiconductor (sCMOS) camera (Orca-FLASH 4.0, Hammatsu. Two objectives (20× and 60×) were used to acquire images.

Results and Discussion

Figure 39:
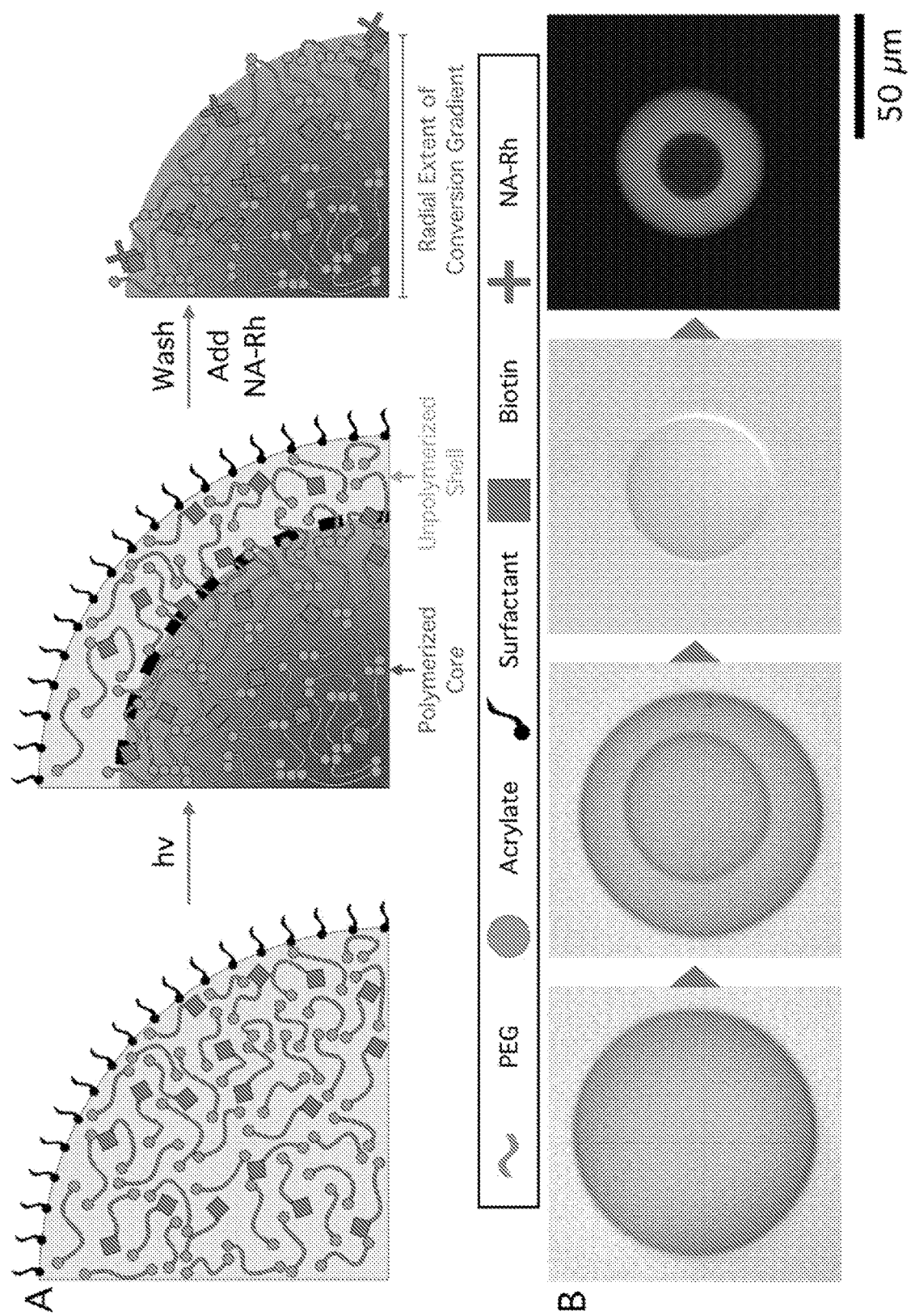
FIGS. 39A-B. Oxygen-inhibited photopolymerization of droplets containing Acryl-PEG-biotin produces functional hydrogels with surfactant-free surfaces.

Photopolymerizable emulsions were formed using a flow-focusing PDMS microfluidic device and polymerized in situ. FIG. 39 is a schematic representation of the copolymerization of acryl-PEG-biotin with PEGDA to form a hydrogel microparticle via photopolymerization in a microfluidic device under ambient conditions. Continuous generation of hydrogel droplets within microfluidic devices enables facile and reproducible control over the composition of each droplet as it is being formed, presenting a unique advantage over batch polymerization processes. Upon exposure to UV light, a polymerized hydrogel core, surrounded by an unpolymerized shell is formed as a consequence of oxygen inhibition, as previously described.[28,32] The thickness of this shell and, consequently, the size of the polymerized core can be easily tuned by adjusting the droplet composition and exposure intensity. The unpolymerized shell, along with surfactant retained at the droplet interface, can be removed via sonication and centrifugation to produce particles with surface properties distinct from that of the parent droplets. The ease of surfactant removal presents yet another advantage of oxygen-inhibited photopolymerization relative to fully-polymerized particles produced in an oxygen-depleted environment, in which the surfactant molecules remain entangled in the hydrogel network at the interface, requiring a second surfactant to re-suspend the particles in an aqueous solution. Surfactant-coated hydrogel interfaces can modify surface interactions and even make the particle surface and functional groups tethered to it inaccessible.

To visualize and quantify the concentration and availability of biotin groups copolymerized in the hydrogel network during the photopolymerization process, particles were incubated within a solution containing Neutravidin-Rhodamine (NA-Rh), which diffused into the hydrogel and bound specifically to biotin. Subsequently hydrogel particles were thoroughly washed and re-suspended in buffer. The strong avidin-biotin affinity retained NA-Rh within the particles, ensuring that fluorescence observed after rinsing was the result of NA-Rh bound to the biotin in the hydrogel network. Fluorescent imaging of particles (FIG. 1B) revealed NA-Rh was distributed inhomogeneously throughout the hydrogel network, suggesting that either the hydrogel network or the availability or activity of biotin displayed spatial variation. Imaging the fluorescence intensity distribution within particles while still immersed in the NA-Rh solution show that the particle core is inaccessible to NA, even after long incubation times. After particle washing, the gradient in fluorescent intensity became apparent, revealing that bound NA was retained in a radially varying manner. It has been previously reported that oxidized biotin does not lose affinity or binding capacity to avidin groups.[34] As Acryl-PEG-Biotin is incorporated into the hydrogel network in a statistical proportion to PEGDA,[35] it follows that the observed NA-Rh intensity traces the crosslinking density of the hydrogel network.

To quantitatively explore this phenomenon, four discrete exposure intensities were used to photopolymerize droplets, while holding all other processing parameters, such as droplet composition and exposure time, constant. Increasing exposure intensity accelerates the rate of photoinitiator radical production. In addition to reducing the unpolymerized shell thickness, increasing UV intensity should affect the rate of macromer conversion and crosslinking. Particles would therefore be generated with crosslinking maxima at the center, crosslinking minima at their surface, and radial crosslinking density profiles that vary nonlinearly with transient oxygen concentration during photopolymerization. As seen in FIG. 40B, particles produced with varying exposure intensity indeed differ not only in size, but also in the final distribution of NA-Rh throughout the particle. Clearly, the radial crosslinking density gradient within the hydrogel network allowed NA molecules, globular proteins with a molecular weight of roughly 60 k Da, to penetrate to a given radial position at which point the hydrogel mesh size becomes too constricted to allow NA diffusion. This penetration length can be visualized as a fluorescent shell surrounding a dark spherical core. This has been observed previously in hydrogel particles for nucleic acid hybridization assays,[16] but the photopolymerization kinetics and their effect on hydrogel network properties were not described.

Figure 40:
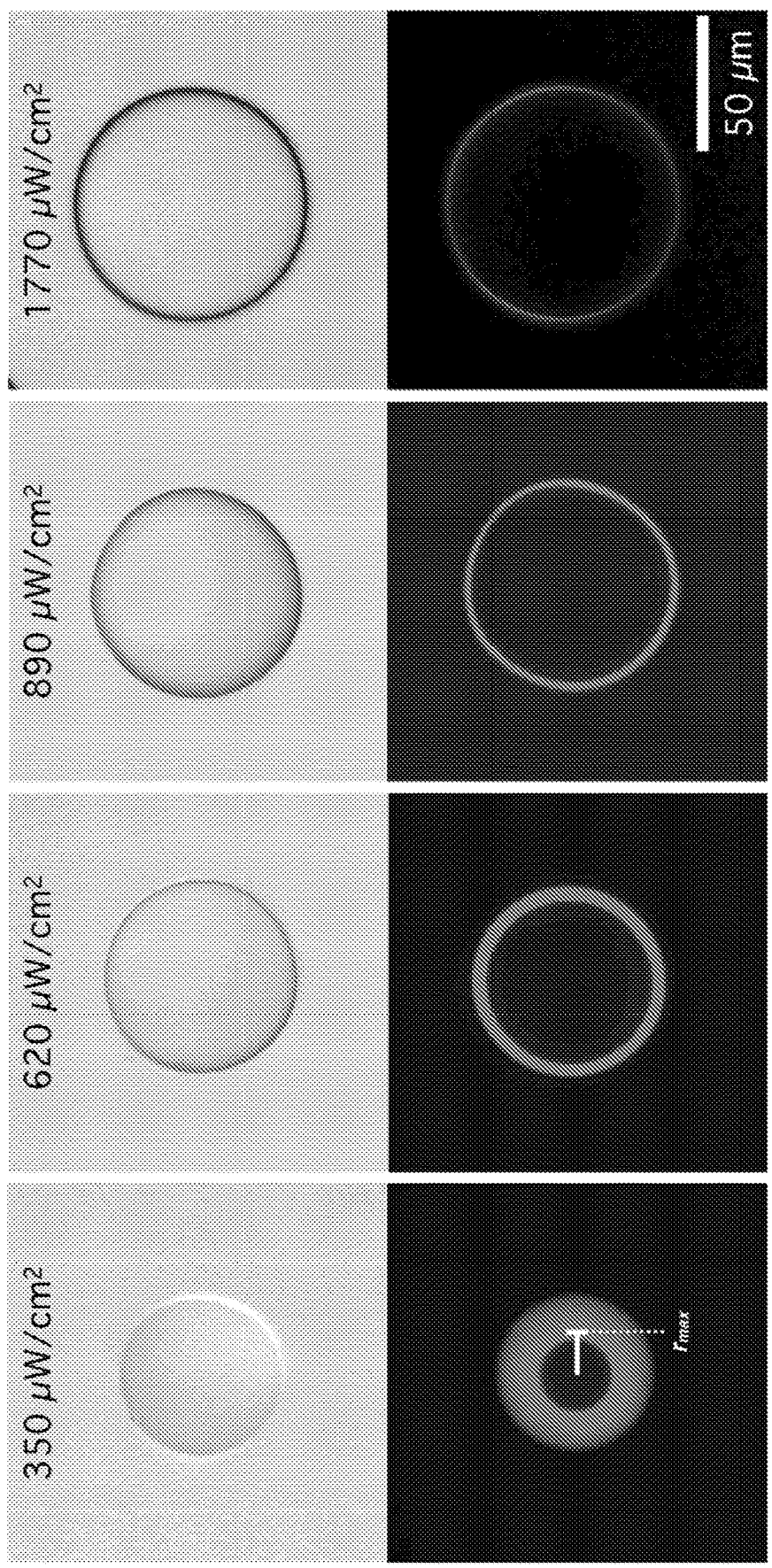
FIG. 40. A Biotin/Neutravidin-Rhodamine (NA-Rh) assay reveals that Neutravidin (NA) penetration is limited to a radial distance that is dictated by photopolymerization conditions. Elucidating the governing reaction-diffusion behavior allows the network architecture to be defined, dictating local hydrogel mechanical properties and biomolecular diffusion for applications such as drug release or bioassays. $r_{max}$: radial position of the maximum florescence intensity.
Figure 41:
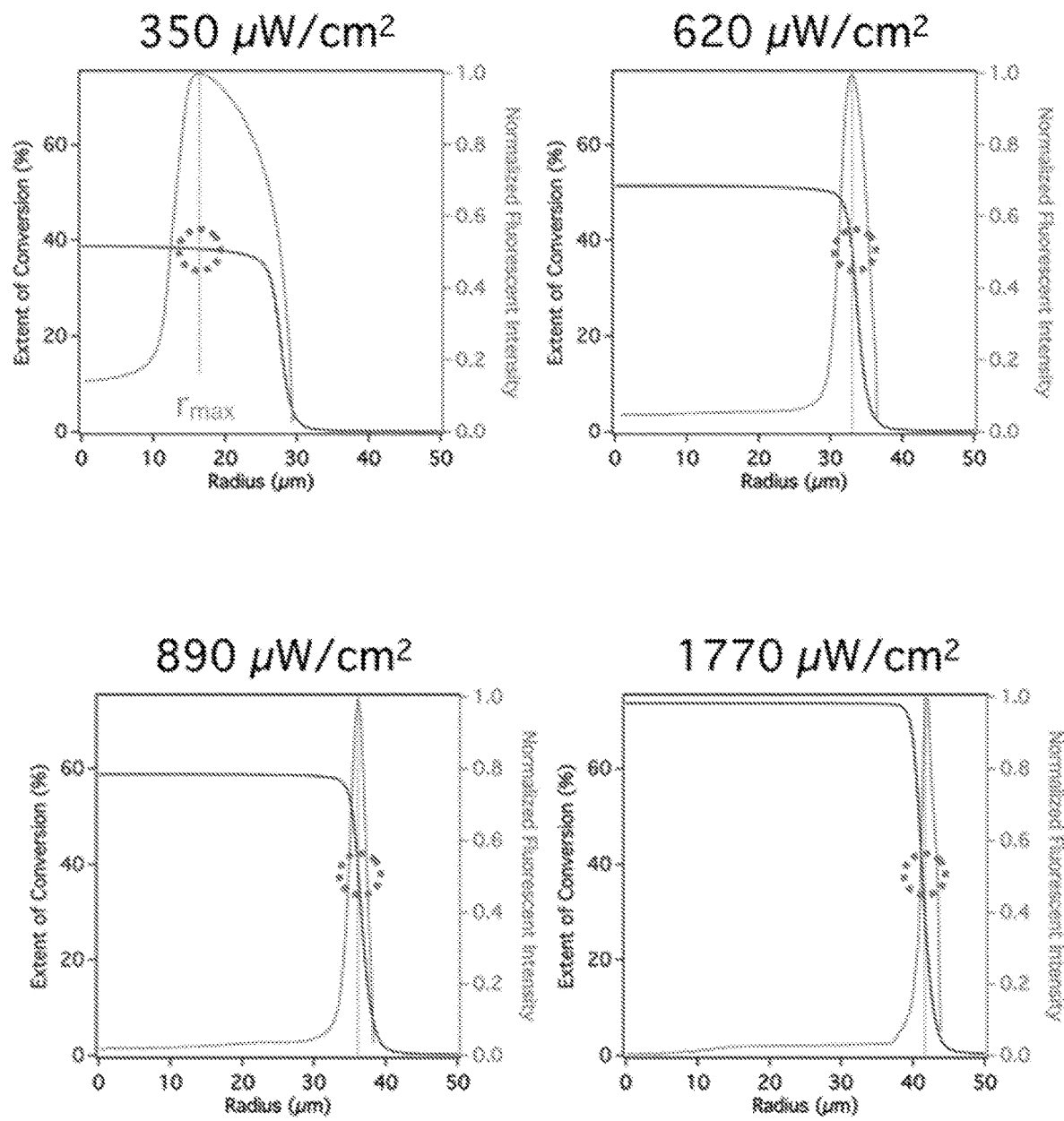
FIG. 41. Experimental fluorescent intensity (green) and reaction-diffusion model prediction of extent of conversion (blue) illustrate that the penetration of fluorescently tagged Neutravidin (NA) into the hydrogel particle is the consequence of constrained network architecture at increasing conversion. Above a threshold extent of conversion, the hydrogel mesh can no longer accommodate the diffusion of Neutravidin. 38% represents this threshold conversion value, while 2% is the extent required to achieve gelation.

Radially-averaged NA-Rh fluorescent intensity profiles corresponding to each UV exposure intensity used in FIG. 40 are summarized in FIG. 41. Two distinct regions can be defined in the hydrogel network using the radial position of the maximum florescence intensity of this profile, $r_{max}$ (FIG. 41, indicated by a vertical dotted line). When $r > r_{max}$, the fluorescent intensity corresponds to the availability of biotin copolymerized into the hydrogel network, and therefore can be used as a descriptor of the local crosslinking density. Since oxygen-inhibited photopolymerization within an emulsion droplet generates a radial conversion gradient, a biotin concentration gradient copolymerized with the crosslinked network decays sharply near the particle surface. For $r < r_{max}$, the fluorescent intensity is no longer a function of the copolymerized biotin concentration and decreases rapidly toward the more homogeneously crosslinked core where very little or no detectable fluorescence can be observed. The exclusion of NA-Rh from the particle core is a consequence of increased crosslinking density and therefore decreased mesh size, which restricts the diffusion of NA-Rh.

Figure 42:
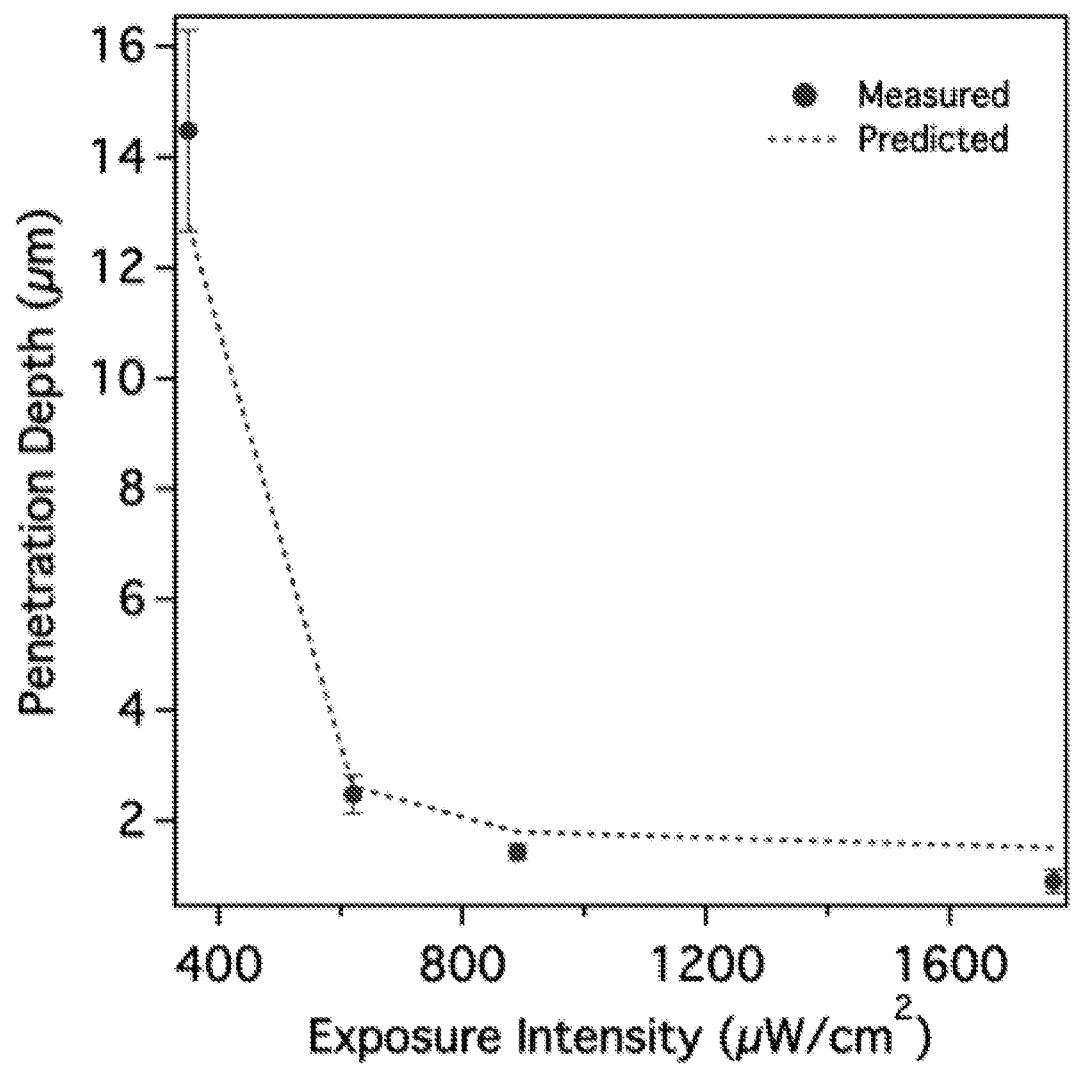
FIG. 42. Calculated NA penetration depth (dotted line), as determined by an extent of conversion threshold value of 38%, accurately predict empirical observations.
Figure 43:
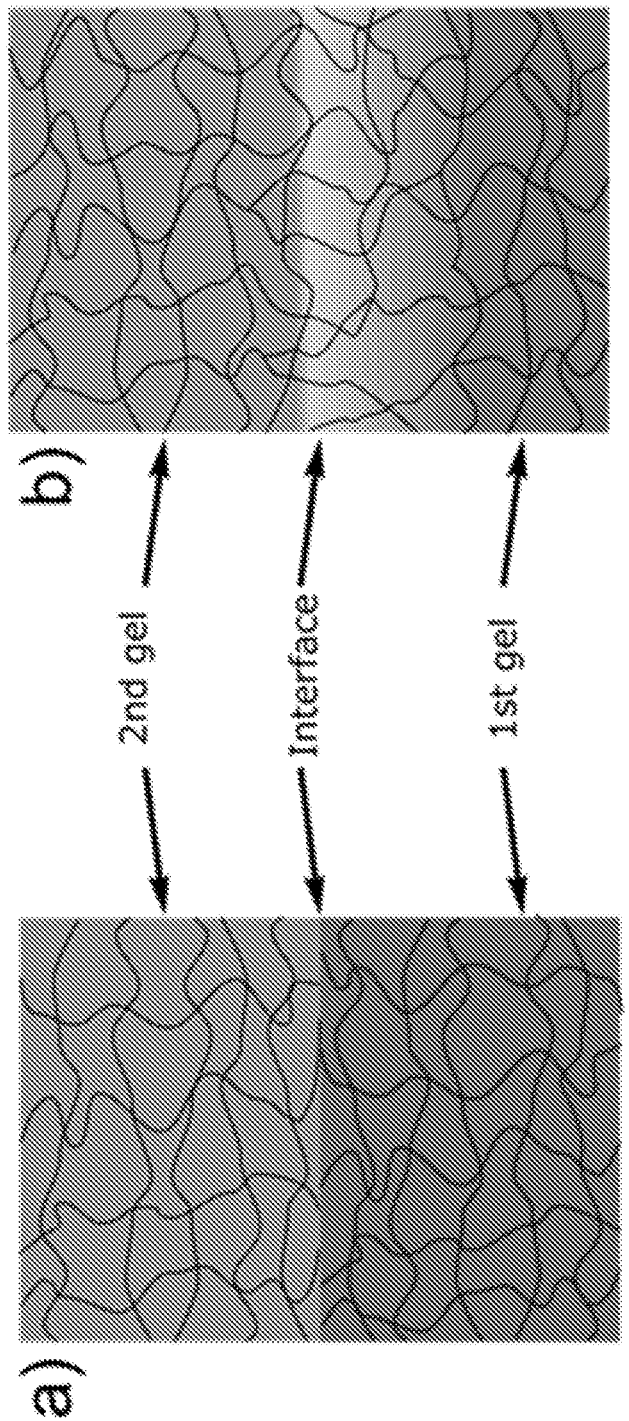
FIG. 43. illustrates the interfacial benefit provided by generating a crosslink gradient by utilizing oxygen inhibition during crosslinking.

To elucidate the relationship between oxygen inhibited photopolymerization kinetics and network architecture, a transient reaction-diffusion model was developed to fully describe hydrogel formation within a single droplet. A full description of this model can be found in the Supplementary Information. The model enables predictions of radial extent of conversion, the amount of macromer locally incorporated into the hydrogel network, which is directly related to the degree of crosslinking for bifunctional macromer units. The extent of macromer conversion, and thus crosslinking density, consequently dictate the hydrogel's network properties. It has been previously shown that an increase in the extent of conversion results in diminished permeability and diffusivity of solutes in PEGDA hydrogels.[36] FIG. 41 summarizes the observed correlation between model prediction of extent of conversion and experimental intensity results. Both data sets are functions of the droplet/particle radius. Previous reports suggest that gelation can be observed above a minimum threshold conversion of 2%.[37] Previously, we validated the accuracy of the reaction-diffusion model in predicting particle size from a particular droplet and given processing parameters.[32] As shown in FIG. 41, the particle size corresponds to the predicted 2% extent of conversion value. It is instructive that for the four different exposure intensity plots all four maxima lines intersected the respective predicted extent of conversion curves at the same value of 38%. The consistent matching of the NA penetration cutoff to a predicted 38% extent of conversion confirms that the hydrogel network surpasses a threshold crosslinking density at which NA-Rh diffusion is restricted. This is further corroborated by FIG. 42, which summarizes model predicted radial positions at which the extent of conversion was 38% (dotted line). These predictions accurately describe empirical observations for the observed NA penetration depth.

Developing an understanding of the coupled oxygen and macromer conversion gradients is important in the design of hydrogels for applications other than biosensing, such as drug delivery, in which water content, gel swelling, hydrolytic degradation rate, modulus, stiffness, and hydrophobicity are all affected by the crosslinking density.[38] Additionally, fine-tuned control of oxygen-inhibited photopolymerization presents a unique opportunity to optimize the availability of functional groups within and at the surface of hydrogel particles. Beyond a threshold conversion, copolymerized functional groups will strictly be accessible at the interface, since the hydrogel network mesh will be too highly crosslinked to allow molecular diffusion into the network. Since the threshold conversion scales inversely with solute size, carefully decreasing the conversion will enable diffusion into the network with well-controlled penetration lengths. For biosensing applications, dense networks that are highly crosslinked at the particle surface suppress sensitivity by presenting fewer accessible functional groups. In contrast, lower UV intensity produced open network architectures with well-defined gradients, which are useful for enhancing bioassay detection sensitivity of biomolecules with different sizes.[22]

Other processing variables, such as exposure time, monomer concentration, and monomer chain length, will also impact the gradient formation process and final network architecture of hydrogel microparticles in a predictable manner. Well-known models are able to predict solute diffusion based solely on solution stoichiometry but disregard extent of conversion effects.[39] Likewise, PEGDA hydrogel network architecture and its dependent properties are typically reported in terms of monomer concentration and molecular weight, disregarding the effects of exposure conditions.[40,41] A comprehensive model that incorporates these effects will be instructive in designing particles with specific network properties for a diverse number of applications, including tuning particle degradation rates, release profiles of encapsulated components, and interaction with microenvironments by modulating particle elasticity. The careful control of hydrogel crosslinking density gradients can also be exploited to generate unique mechanical properties for tissue engineering. While results here were collected using particles with a size range of 60-100 µm, they may be extrapolated to larger or smaller particles produced using oxygen-inhibited photopolymerization.

CONCLUSION

Described herein is a hydrogel microparticle fabrication platform that enables the generation of radial crosslinking density gradients by exploiting oxygen-inhibited photopolymerization in a microfluidic device. This platform overcomes the limitations of previously reported techniques, such as SFL, by facilitating the continuous, high-throughput generation of custom hydrogel particles without the need for porogens or graded material precursors.[21-23] The application of these particles as macromolecular biosensors by incorporating biofunctional molecules was demonstrated using a model biotin-avidin assay, which revealed network architecture dependence on local gelation kinetics and operating parameters. The generation of radial crosslinking density gradients was empirically observed as a diffusive limitation of NA-Rh into the particle past a critical penetration depth, which was dependent on UV exposure intensity. Experimental observations were corroborated with a reaction-diffusion model that predicted a constant threshold conversion of 38%, which matched the penetration depth for different exposure intensities. The accurate predictive capabilities provided by this reaction-diffusion model can be applied to easily design hydrogel particles with custom network architectures based on photopolymerization conditions. While this work focused on the detection of mobile species following their diffusion into the particle, these particles can also be utilized in drug delivery and tissue engineering applications, where the careful modulation of particle degradation and molecular release is critical.

REFERENCES (1) Liu, A. L.; Garcia, A. J. Methods for Generating Hydrogel Particles for Protein Delivery. *Annals of Biomedical Engineering* 2016, 44 (6), 1946-1958.

(2) Hwang, D. K.; Oakey, J.; Toner, M.; Arthur, J. A.; Anseth, K. S.; Lee, S.; Zeiger, A.; Van Vliet, K. J.; Doyle, P. S. Stop-Flow Lithography for the Production of Shape-Evolving Degradable Microgel Particles. *J. Am. Chem. Soc.* 2009, 131 (12), 4499-4504.

(3) DeForest, C. A.; Polizzotti, B. D.; Anseth, K. S. Sequential Click Reactions for Synthesizing and Patterning Three-Dimensional Cell Microenvironments. *Nature Materials* 2009, 8 (8), 659-664.

(4) Kloxin, A. M.; Tibbitt, M. W.; Anseth, K. S. Synthesis of Photodegradable Hydrogels as Dynamically Tunable Cell Culture Platforms. *Nature Protocols* 2010, 5 (12), 1867-1887.

(5) Zhu, J. Bioactive Modification of Poly(Ethylene Glycol) Hydrogels for Tissue Engineering. Biomaterials 2010, 31 (17), 4639-4656.

(6) Ahmad, M.; Rai, S. M.; Mahmood, A. Hydrogel Microparticles as an Emerging Tool in Pharmaceutical Field: a Review. Adv. Polym. Technol. 2015, 35 (2), 121-128.

(7) Burdick, J. A.; Anseth, K. S. Photoencapsulation of Osteoblasts in Injectable RGD-Modified PEG Hydrogels for Bone Tissue Engineering. Biomaterials 2002, No. 23, 4315-4323.

(8) Buenger, D.; Topuz, F.; Groll, J. Hydrogels in Sensing Applications. *Progress in Polymer Science* 2012, 37 (12), 1678-1719.

(9) Lee, A. G.; Arena, C. P.; Beebe, D. J.; Palecek, S. P. Development of Macroporous Poly(Ethylene Glycol) Hydrogel Arrays Within Microfluidic Channels. *Biomacromolecules* 2010, 11 (12), 3316-3324.

(10) Sakhalkar, H. S. Enhanced Adhesion of Ligand-Conjugated Biodegradable Particles to Colitic Venules. *The FASEB Journal* 2005, 1-19.

(11) Burdick, J. A.; Khademhosseini, A.; Langer, R. Fabrication of Gradient Hydrogels Using a Microfluidics/Photopolymerization Process. *Langmuir* 2004, 20 (13), 5153-5156.

(12) Yadavalli, V. K.; Koh, W.-G.; Lazur, G. J.; Pishko, M. V. Microfabricated Protein-Containing Poly(Ethylene Glycol) Hydrogel Arrays for Biosensing. *Sensors and Actuators B: Chemical* 2004, 97 (2-3), 290-297.

(13) Rehman, F. N.; Audeh, M.; Abrams, E. S.; Hammond, P. W.; Kenney, M.; Boles, T. C. Immobilization of Acrylamide-Modified Oligonucleotides by Co-Polymerization. *Nucleic Acids Res* 1999, 27 (2), 649-655.

(14) Kenney, M.; Ray, S.; Boles, T. C. Mutation Typing Using Electrophoresis and Gel-Immobilized Acrydite. *BioTechniques* 1998, 25 (3), 516-521.

(15) Lee, Y.; Choi, D.; Koh, W.-G.; Kim, B. Poly(Ethylene Glycol) Hydrogel Microparticles Containing Enzyme-Fluorophore Conjugates for the Detection of Organophosphorus Compounds. *Sensors and Actuators B: Chemical* 2009, 137 (1), 209-214.

(16) Lewis, C. L.; Choi, C.-H.; Lin, Y.; Lee, C.-S.; Yi, H. Fabrication of Uniform DNA-Conjugated Hydrogel Microparticles via Replica Molding for Facile Nucleic Acid Hybridization Assays. *Anal. Chem.* 2010, 82 (13), 5851-5858.

(17) Le Goff, G. C.; Srinivas, R. L.; Hill, W. A.; Doyle, P. S. Hydrogel Microparticles for Biosensing. *European Polymer Journal* 2015, 72 (C), 386-412.

(18) Pregibon, D.; Toner, M.; Doyle, P. Multifunctional Encoded Particles for High-Throughput Biomolecule Analysis. *Science* 2007, 315, 1393-1396.

(19) Helgeson, M. E.; Chapin, S. C.; Doyle, P. S. Hydrogel Microparticles From Lithographic Processes: Novel Materials for Fundamental and Applied Colloid Science. *Current Opinion in Colloid & Interface Science* 2011, 16 (2), 106-117.

(20) Appleyard, D. C.; Chapin, S. C.; Srinivas, R. L.; Doyle, P. S. Bar-Coded Hydrogel Microparticles for Protein Detection: Synthesis, Assay and Scanning. *Nature Protocols* 2011, 6 (11), 1761-1774.

(21) Bong, K. W.; Chapin, S. C.; Doyle, P. S. Magnetic Barcoded Hydrogel Microparticles for Multiplexed Detection. *Langmuir* 2010, 26 (11), 8008-8014.

(22) Choi, N. W.; Kim, J.; Chapin, S. C.; Duong, T.; Donohue, E.; Pandey, P.; Broom, W.; Hill, W. A.; Doyle, P. S. Multiplexed Detection of mRNA Using Porosity-Tuned Hydrogel Microparticles. Anal. Chem. 2012, 84 (21), 9370-9378.

(23) Luchini, A.; Geho, D. H.; Bishop, B.; Tran, D.; Xia, C.; Dufour, R. L.; Jones, C. D.; Espina, V.; Patanarut, A.; Zhou, W.; Ross, M. M.; Tessitore, A.; Petricoin, E. F.; Liotta, L. A. Smart Hydrogel Particles: Biomarker Harvesting: One-Step Affinity Purification, Size Exclusion, and Protection Against Degradation. *Nano Lett.* 2008, 8 (1), 350-361.

(24) Mahadik, B. P.; Wheeler, T. D.; Sketch, L. J.; Kenis, P. J. A.; Harley, B. A. C. Microfluidic Generation of Gradient Hydrogels to Modulate Hematopoietic Stem Cell Culture Environment. *Adv. Healthcare Mater.* 2013, 3 (3), 449-458.

(25) Teh, S.-Y.; Lin, R.; Hung, L.-H.; Lee, A. P. Droplet Microfluidics. *Lab Chip* 2008, 8 (2), 198-23.

(26) Kim, J. H.; Jeon, T. Y.; Choi, T. M.; Shim, T. S.; Kim, S.-H.; Yang, S.-M. Droplet Microfluidics for Producing Functional Microparticles. *Langmuir* 2014, 30 (6), 1473-1488.

(27) Dang, T.-D.; Kim, Y. H.; Kim, H. G.; Kim, G. M. Preparation of Monodisperse PEG Hydrogel Microparticles Using a Microfluidic Flow-Focusing Device. *Journal of Industrial and Engineering Chemistry* 2012, 18 (4), 1308-1313.

(28) Krutkramelis, K.; Xia, B.; Oakey, J. Monodisperse Polyethylene Glycol Diacrylate Hydrogel Microsphere Formation by Oxygen-Controlled Photopolymerization in a Microfluidic Device. *Lab Chip* 2016, 16 (8), 1457-1465.

(29) Decker, C.; Jenkins, A. D. Kinetic Approach of O2 Inhibition in Ultraviolet- and Laser-Induced Polymerizations. *Macromolecules* 1985, 1241-1244.

(30) Ligon, S. C.; Husár, B.; Wutzel, H.; Holman, R.; Liska, R. Strategies to Reduce Oxygen Inhibition in Photoinduced Polymerization. *Chem. Rev.* 2014, 114 (1), 557-589.

(31) Xia, B.; Jiang, Z.; Debroy, D.; Li, D.; Oakey, J. Cytocompatible Cell Encapsulation via Hydrogel Photopolymerization in Microfluidic Emulsion Droplets. *Biomicrofluidics* 2017, 11 (4), 044102-044111.

(32) Debroy, D.; Oakey, J.; Li, D. Interfacially-Mediated Oxygen Inhibition for Precise and Continuous Poly(Ethylene Glycol) Diacrylate (PEGDA) Particle Fabrication. *Journal of Colloid And Interface Science* 2018, 510, 334-344.

(33) Xia, Y.; Whitesides, G. M. Soft Lithography. *Annu. Rev. Mater. Sci.* 1998, 153-185.

(34) Melville, D.; Genghof, D.; Lee, J. Biological Properties of Biotin D- and L- Sulfoxides. *J. Biol. Chem.* 1954, No. 208, 503-512.

(35) Beamish, J. A.; Zhu, J.; Kottke-Marchant, K.; Marchant, R. E. The Effects of Monoacrylated Poly(Ethylene Glycol) on the Properties of Poly(Ethylene Glycol) Diacrylate Hydrogels Used for Tissue Engineering. *J. Biomed. Mater. Res.* 2009, 9999A, NA-NA.

(36) Anseth, K. S.; Metters, A. T.; Bryant, S. J.; Martens, P. J.; Elisseeff, J. H.; Bowman, C. N. In Situ Forming Degradable Networks and Their Application in Tissue Engineering and Drug Delivery. *Journal of Controlled Release* 2002, 78, 199-209.

(37) Andrzejewska, E. Photopolymerization Kinetics of Multifunctional Monomers. *Progress in Polymer Science* 2001, 26 (4), 605-665.

(38) Lin, C.-C.; Anseth, K. S. PEG Hydrogels for the Controlled Release of Biomolecules in Regenerative Medicine. *Pharm Res* 2008, 26 (3), 631-643.

(39) Lustig, S.; Peppas, N. A. Solute Diffusion in Swollen Membranes. IX. Scaling Laws for Solute Diffusion in Gels. *Journal of Applied Polymer Science* 1988, 735-747.

(40) Hagel, V.; Haraszti, T.; Boehm, H. Diffusion and Interaction in PEG-DA Hydrogels. *Biointerphases* 2013, 8 (36), 1-9.

(41) Cruise, G.; Scharp, D.; Hubbell, J. Characterization of Permeability and Network Structure of Interfacially Photopolymerized Poly(Ethylene Glycol) Diacrylate Hydrogels. Biomaterials 1998, No. 19, 1287-1294.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of generating a plurality of microparticles comprising:
 providing a continuous phase comprising a non-aqueous liquid and a dispersed phase comprising an aqueous solution including a functionalized monomer or a macromer and a photoinitiator;
 forming a composition comprising microdroplets of said aqueous solution dispersed in said non-aqueous liquid via a surfactant;
 diffusing oxygen through said non-aqueous liquid into said microdroplets;
 partially polymerizing a first microdroplet, thereby generating a first microparticle covered in an unpolymerized layer of aqueous solution, the first microparticle being smaller than the first microdroplet; and
 removing the unpolymerized layer of aqueous solution to expose a surfactant-free functionalized surface;
 wherein the functionalized monomer or macromer and the functionalized surface comprise functional groups configured for selective molecular binding.

2. The method of claim 1, wherein the step of diffusing oxygen into said microdroplets generates an oxygen concentration gradient in the first microdroplet.

3. The method of claim 2, wherein said oxygen concentration gradient results in a crosslinking gradient in the first microparticle.

4. The method of claim 3, comprising controlling the crosslinking gradient via oxygen concentration during the partially polymerizing step such that molecules larger than a predetermined size are prevented from diffusing into the microparticle.

5. The method of claim 1, wherein said step of partially polymerizing the first microdroplet comprises inhibiting polymerization via oxygen.

6. The method of claim 1, wherein said step of partially polymerizing the first microdroplet comprises exposing the first microdroplet to UV light.

7. The method of claim 1, wherein the composition is formed in a microfluidic device, the method comprising flowing the microdroplets through one or more channels of the microfluidic device.

8. The method of claim 1, wherein said microdroplets have an average primary cross-sectional dimension of less than or equal to 100 µm and wherein the microparticle has a primary cross-sectional dimension of less than or equal to 20 µm.

9. The method of claim 1 comprising treating the functionalized surface of said microparticle with a biological material.

10. The method of claim 1, wherein said aqueous phase further comprises a biological material.

11. A microparticle generated using the method of claim 1.

12. The method of claim 1, wherein the aqueous solution includes the functionalized monomer or a macromer and a crosslinking hydrogel backbone monomer or macromer.

13. The method of claim 12, wherein the partially polymerizing step comprises forming a crosslinked copolymer with functional groups of the crosslinked copolymer exposed to an exterior of the microparticle.

14. The method of claim 1, wherein the functionalized surface of the microparticle is configured to exhibit at least one of: selective binding of particular species, biological functions, pharmacological functions and combinations thereof.

15. The method of claim 1, wherein the partially polymerizing step comprises controlling the extent of conversion to below a threshold value in order to allow a target molecule to diffuse into a core of the microparticle.

16. The method of claim 15, wherein the threshold value is selected based on a size of the target molecule.

17. The method of claim 16 wherein the threshold value is less than 50%.

18. The method of claim 16 wherein the threshold value is 38%.

19. The method of claim 1, wherein the functional groups are configured for the detection of bioactive macromolecules.

20. The method of claim 1, wherein the functional groups are configured for molecular recognition.

21. The method of claim 20, wherein the molecular recognition comprises ligand-protein binding.

22. The method of claim 1, wherein the functional groups comprise ligands.

* * * * *